US011899021B2

(12) United States Patent
Dart et al.

(10) Patent No.: US 11,899,021 B2
(45) Date of Patent: *Feb. 13, 2024

(54) LUCIFERASE-BASED THERMAL SHIFT ASSAYS

(71) Applicant: Promega Corporation, Madison, WI (US)

(72) Inventors: Melanie Dart, Madison, WI (US); Lance P. Encell, Fitchburg, WI (US); Thomas Kirkland, Atascadero, CA (US); Thomas Machleidt, Madison, WI (US); Matthew Robers, Madison, WI (US); Brock F. Binkowski, Sauk City, WI (US); Keith Wood, Mt. Horeb, WI (US); Ce Shi, San Luis Obispo, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/150,018

(22) Filed: Jan. 4, 2023

(65) Prior Publication Data

US 2023/0341410 A1     Oct. 26, 2023

Related U.S. Application Data

(60) Continuation of application No. 17/105,024, filed on Nov. 25, 2020, now Pat. No. 11,567,083, which is a continuation of application No. 16/787,950, filed on Feb. 11, 2020, now Pat. No. 10,928,400, which is a division of application No. 15/017,271, filed on Feb. 5, 2016, now Pat. No. 10,571,471.

(60) Provisional application No. 62/112,518, filed on Feb. 5, 2015.

(51) Int. Cl.

| | |
|---|---|
| *C12Q 1/66* | (2006.01) |
| *C12Q 1/68* | (2018.01) |
| *G01N 21/64* | (2006.01) |
| *G01N 33/53* | (2006.01) |
| *G01N 33/58* | (2006.01) |
| *G01N 33/68* | (2006.01) |
| *G01N 33/569* | (2006.01) |

(52) U.S. Cl.
CPC .. *G01N 33/6845* (2013.01); *C12Y 113/12007* (2013.01); *G01N 21/6428* (2013.01); *G01N 33/56916* (2013.01); *G01N 33/581* (2013.01); *G01N 33/582* (2013.01); *G01N 2021/6432* (2013.01); *G01N 2021/6439* (2013.01); *G01N 2333/90241* (2013.01); *G01N 2500/04* (2013.01); *G01N 2500/10* (2013.01)

(58) Field of Classification Search
CPC ........ G01N 33/53; G01N 33/58; G01N 21/64; G01N 2021/6439; G01N 2500/10; C12N 2529/10; C12Q 1/66; C12Q 1/68
See application file for complete search history.

(56) References Cited

U.S. PATENT DOCUMENTS

| | | |
|---|---|---|
| 5,585,277 A | 12/1996 | Bowie et al. |
| 6,245,512 B1 | 6/2001 | Williams et al. |
| 8,557,970 B2 | 10/2013 | Encell et al. |
| 8,669,103 B2 | 3/2014 | Binkowski et al. |
| 9,523,693 B2 | 12/2016 | Nordlund et al. |
| 9,797,889 B2* | 10/2017 | Dixon .................. C07K 7/08 |
| 10,571,471 B2 | 2/2020 | Dart et al. |
| 2002/0068298 A1 | 6/2002 | Tomich et al. |
| 2006/0211007 A1 | 9/2006 | Cornish et al. |
| 2007/0086949 A1 | 4/2007 | Prasad et al. |
| 2010/0281552 A1 | 11/2010 | Encell et al. |
| 2011/0130305 A1 | 6/2011 | Patton et al. |
| 2014/0057368 A1 | 2/2014 | Nordlund |
| 2014/0194307 A1 | 7/2014 | Hitko et al. |
| 2014/0348747 A1 | 11/2014 | Dixon et al. |
| 2014/0363375 A1 | 12/2014 | Dixon et al. |
| 2020/0174012 A1 | 6/2020 | Dart et al. |

FOREIGN PATENT DOCUMENTS

| | | |
|---|---|---|
| WO | WO 1997/020952 | 6/1997 |
| WO | WO 2006/079334 | 8/2006 |
| WO | WO 2014/151736 | 9/2014 |
| WO | WO 2016/127100 | 8/2016 |

OTHER PUBLICATIONS

Dart et al., Homogeneous Assay for Target Engagement Utilizing Bioluminescent Thermal Shift. ACS Med Chem Lett. Apr. 16, 2018;9(6):546-551.

Diwu et al., Fluorescent Molecular Probes II. The Synthesis, Spectral Properties and Use of Fluorescent Solvatochromic Dapoxyl Dyes. Photochemistry and Photobiology. 1997;66(4): 424-431.

Hawe et al., Extrinsic fluorescent dyes as tools for protein characterization. Pharm Res. Jul. 2008;25(7):1487-99.

Jafari et al., The cellular thermal shift assay for evaluating drug target interactions in cells. Nat Protoc. Sep. 2014;9(9):2100-22.

Koshland, Application of a Theory of Enzyme Specificity to Protein Synthesis. Proc Natl Acad Sci U S A. Feb. 1958;44(2):98-104.

Kovalsa et al., Dyes and Pigments. Dyes and Pigments. 2005;67(1):47-54.

Linderstrom-Lang et al., Protein Structure and Enzyme Activity, in The Enzymes., 1959, Chapter 10, pp. 443-510.

Molina et al. Monitoring drug target engagement in cells and tissues using the cellular thermal shift assay. Science. Jul. 5, 2013;341(6141):84-7.

Moreau et al., Quantitative determination of protein stability and ligand binding using a green fluorescent reporter system. Mol Biosyst. Jul. 2010;6(7):1285-92.

(Continued)

*Primary Examiner* — Maryam Monshipouri
(74) *Attorney, Agent, or Firm* — David W. Staple

(57) ABSTRACT

Provided herein are systems and methods for characterizing target/ligand engagement. In particular, luciferase-labeled polypeptide targets are used to detect or quantify target/ligand engagement (e.g., within a cell or cell lysate).

11 Claims, 54 Drawing Sheets

Specification includes a Sequence Listing.

(56) References Cited

OTHER PUBLICATIONS

Semisotnov et al., Study of the "molten globule" intermediate state in protein folding by a hydrophobic fluorescent probe. Biopolymers. Jan. 1991;31(1):119-28.
Volkova et al., Cyanine dye-protein interactions: looking for fluorescent probes for amyloid structures. J Biochem Biophys Methods. Aug. 1, 2007;70(5):727-33.
Volkova et al., Specific fluorescent detection of fibrillar alpha-synuclein using mono- and trimethine cyanine dyes. Bioorg Med Chem. Feb. 1, 2008;16(3):1452-9.
International Search Report and Written Opinion for PCT/US2016/016846, dated May 3, 2016, 23 pages.
Extended European Search Report for EP 16747366, dated May 3, 2018, 8 pages.

* cited by examiner

FIG. 3A
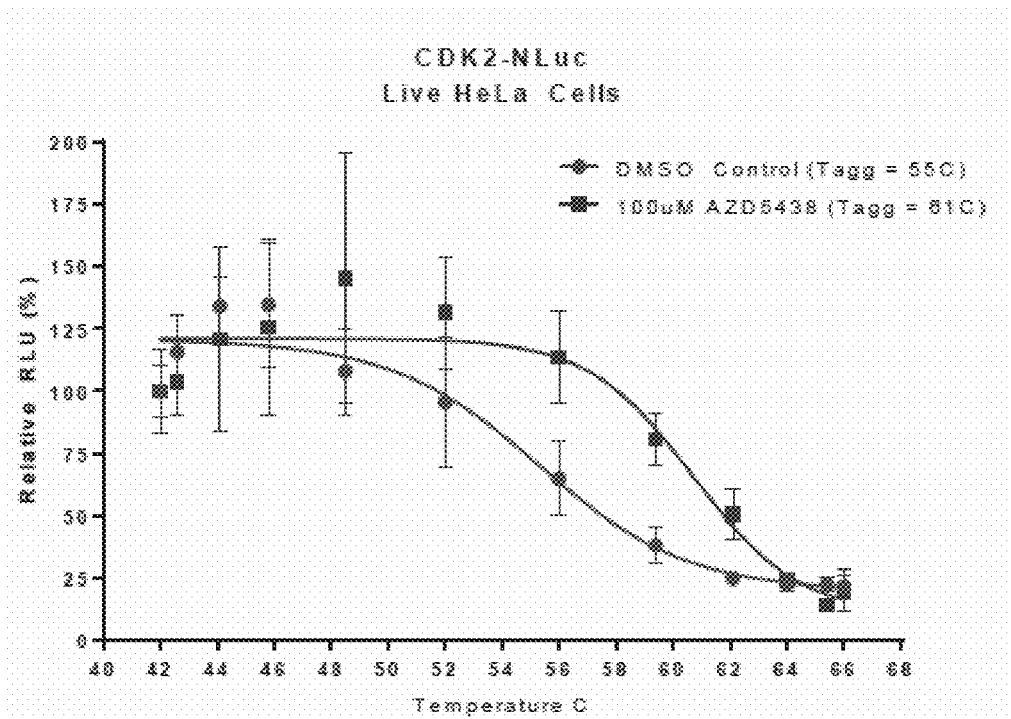
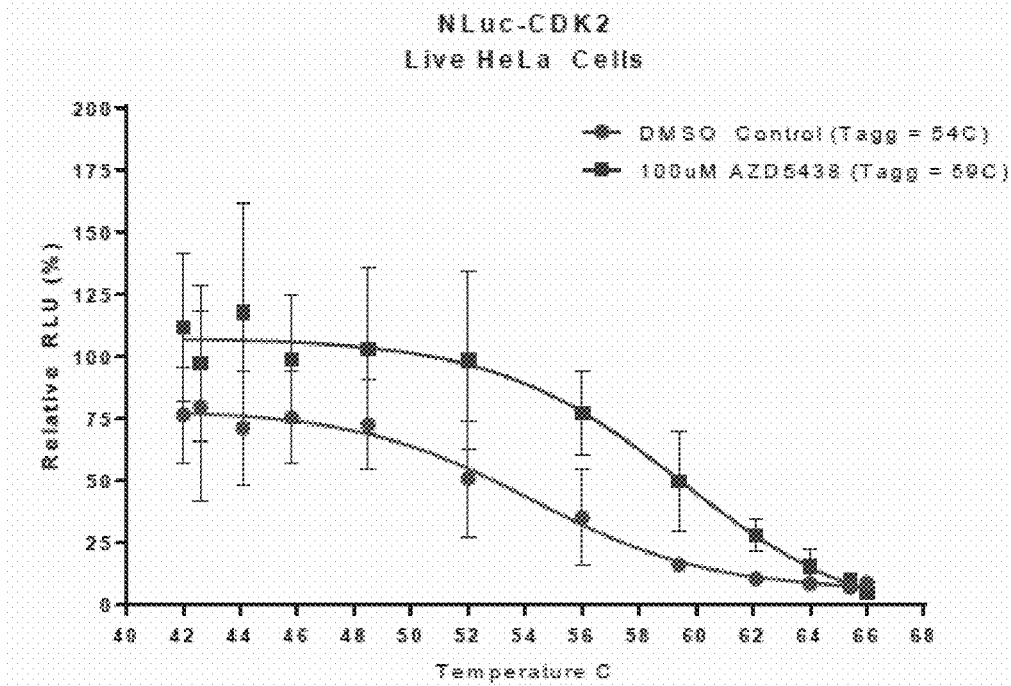
FIG. 3B

FIG. 3C
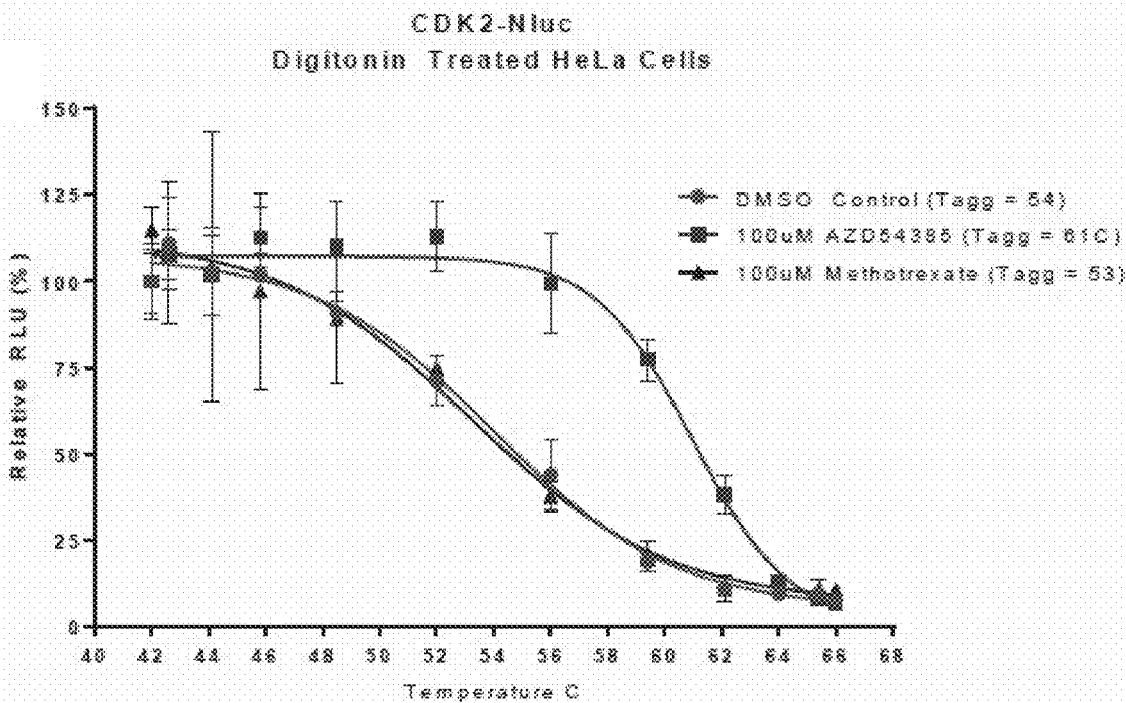
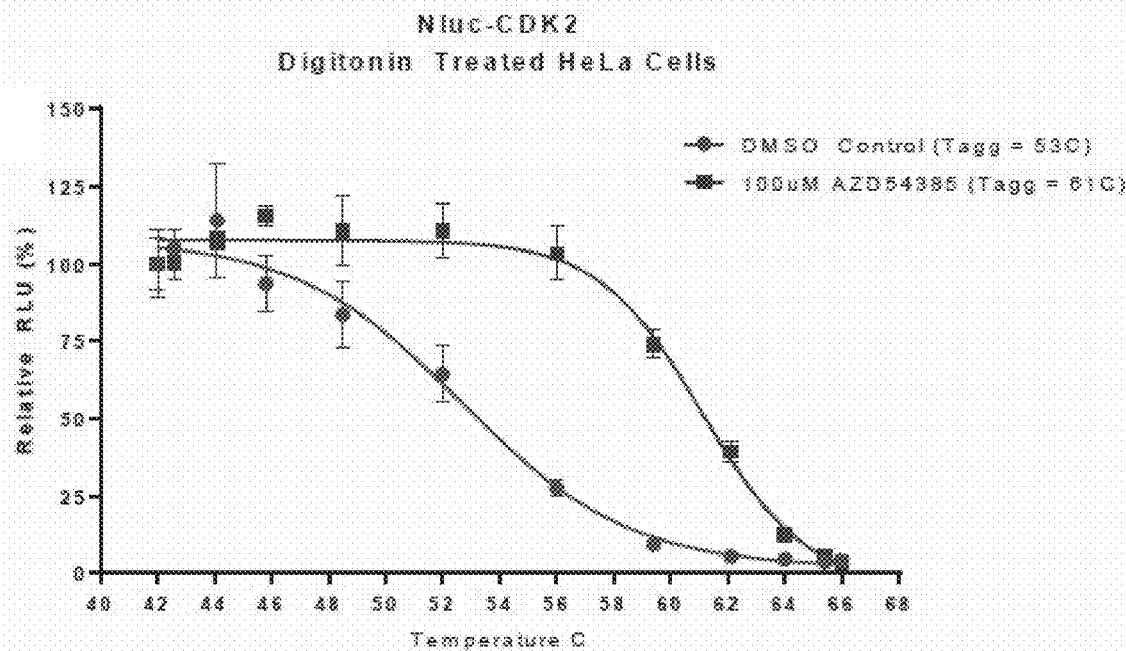
FIG. 3D

FIG. 5A
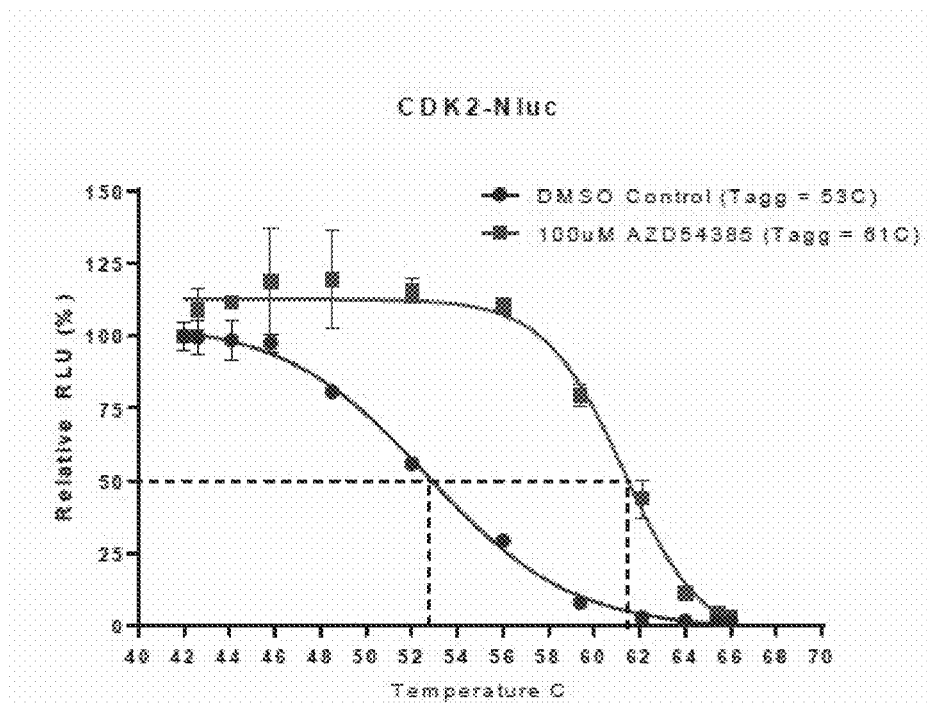
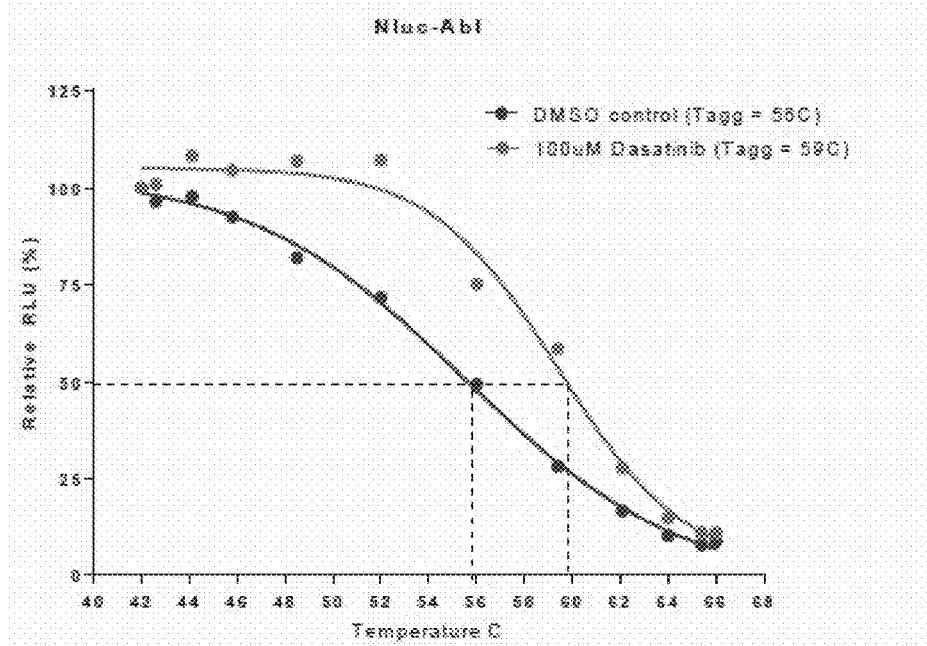
FIG. 5B

FIG. 5C
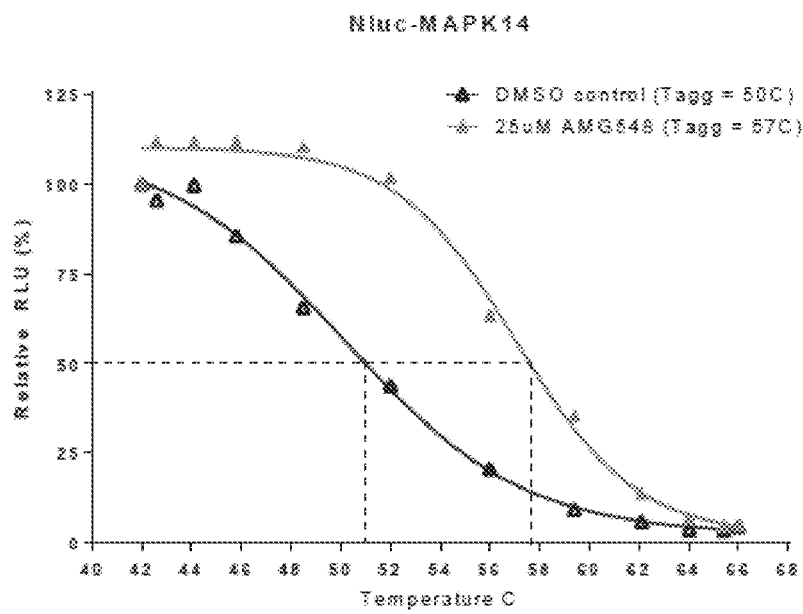
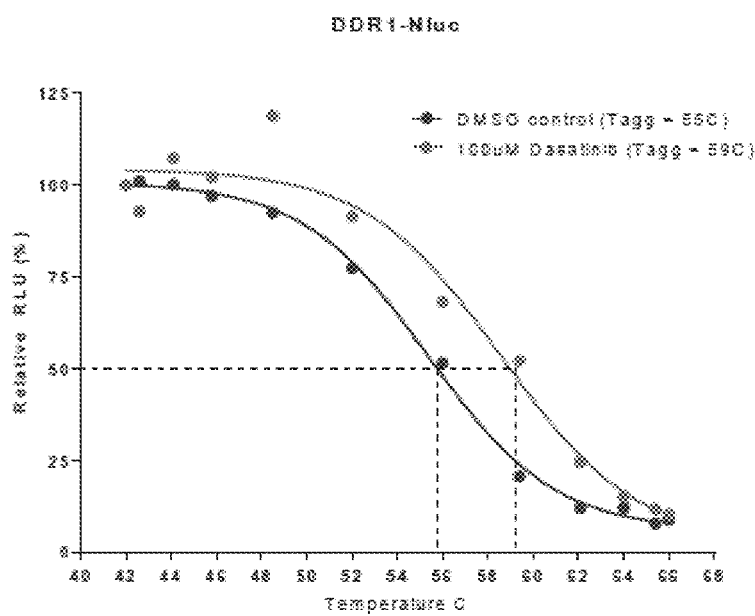
FIG. 5D

FIG. 5E
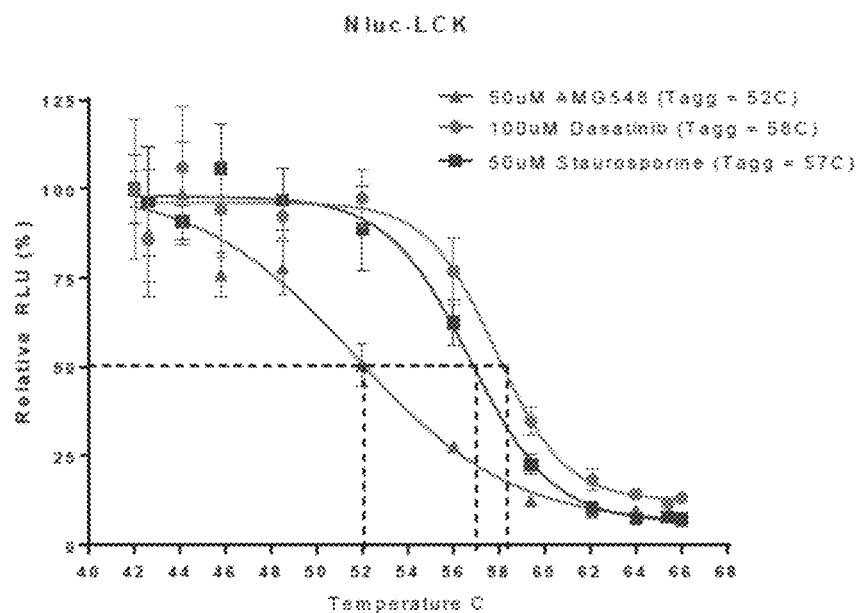
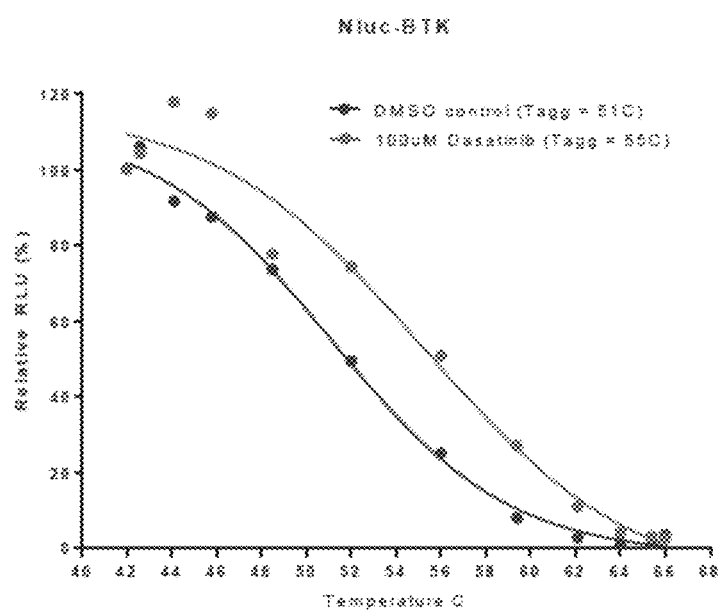
FIG. 5F

FIG. 14A
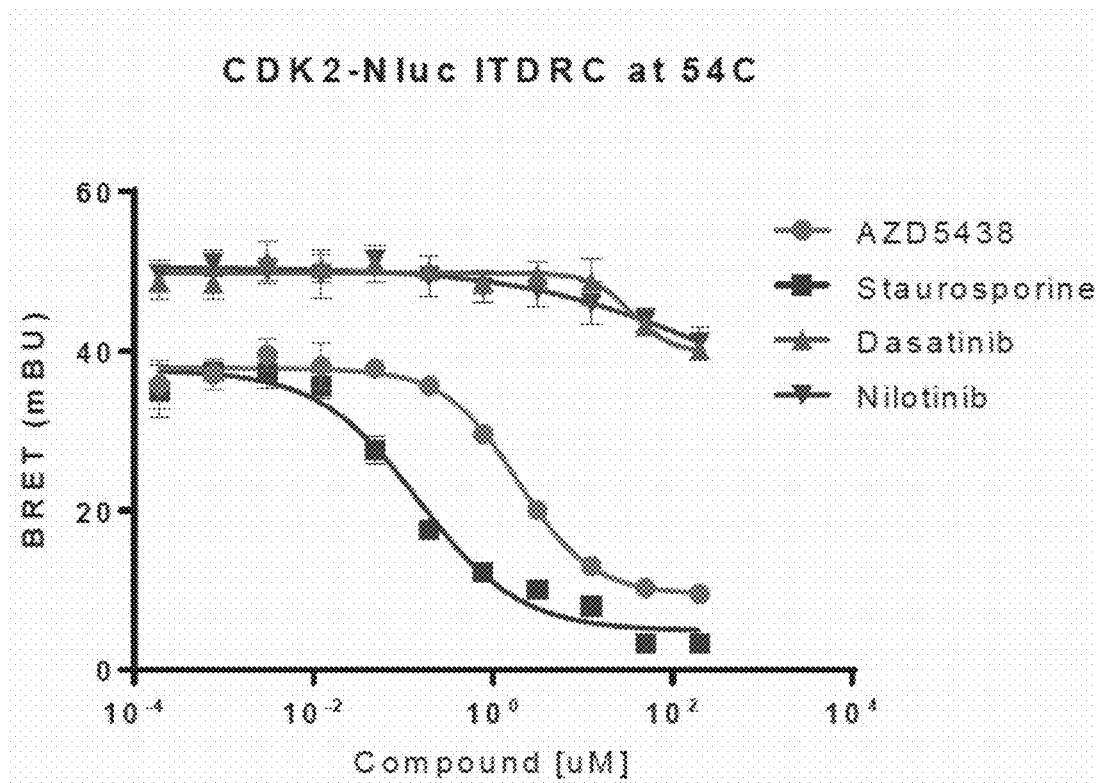
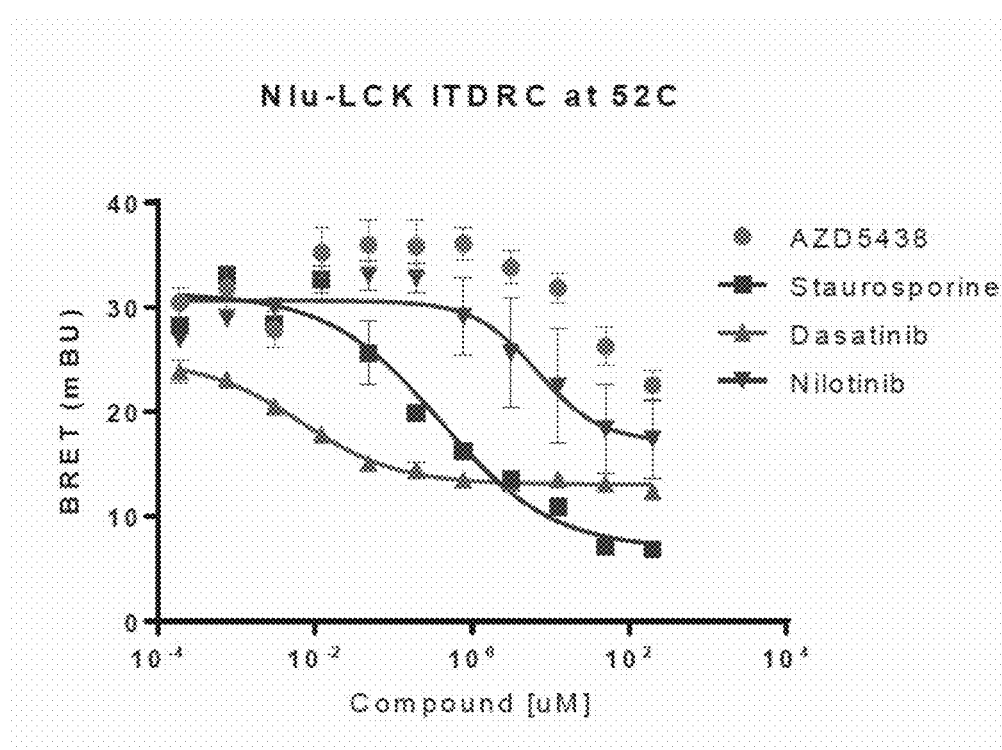
FIG. 14B

FIG. 15A
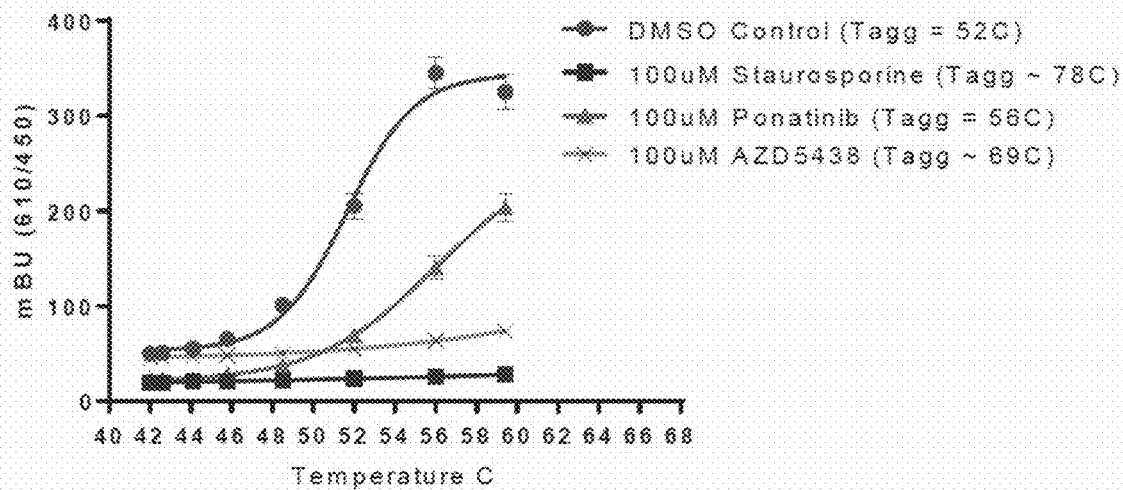
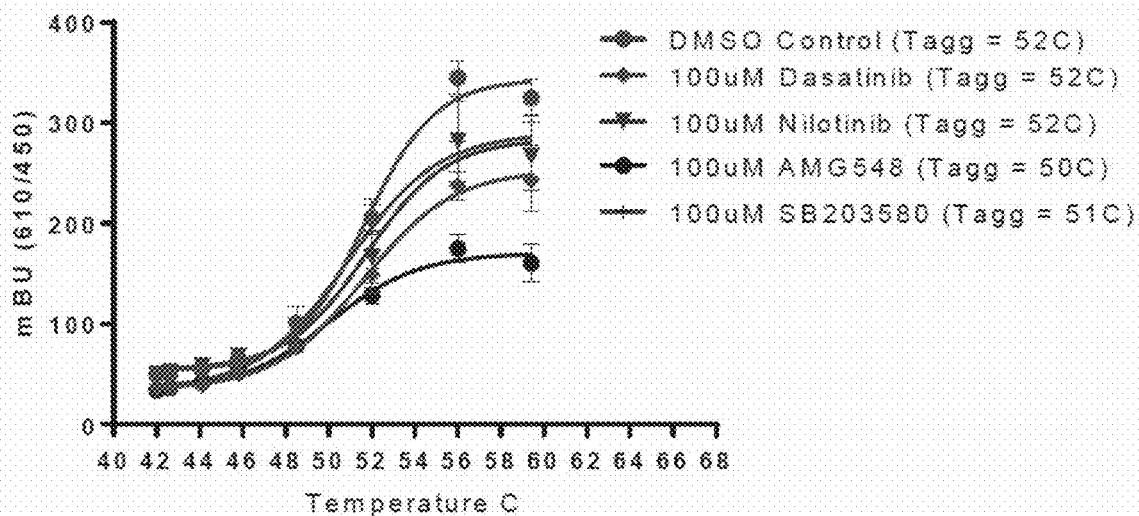

FIG. 17B
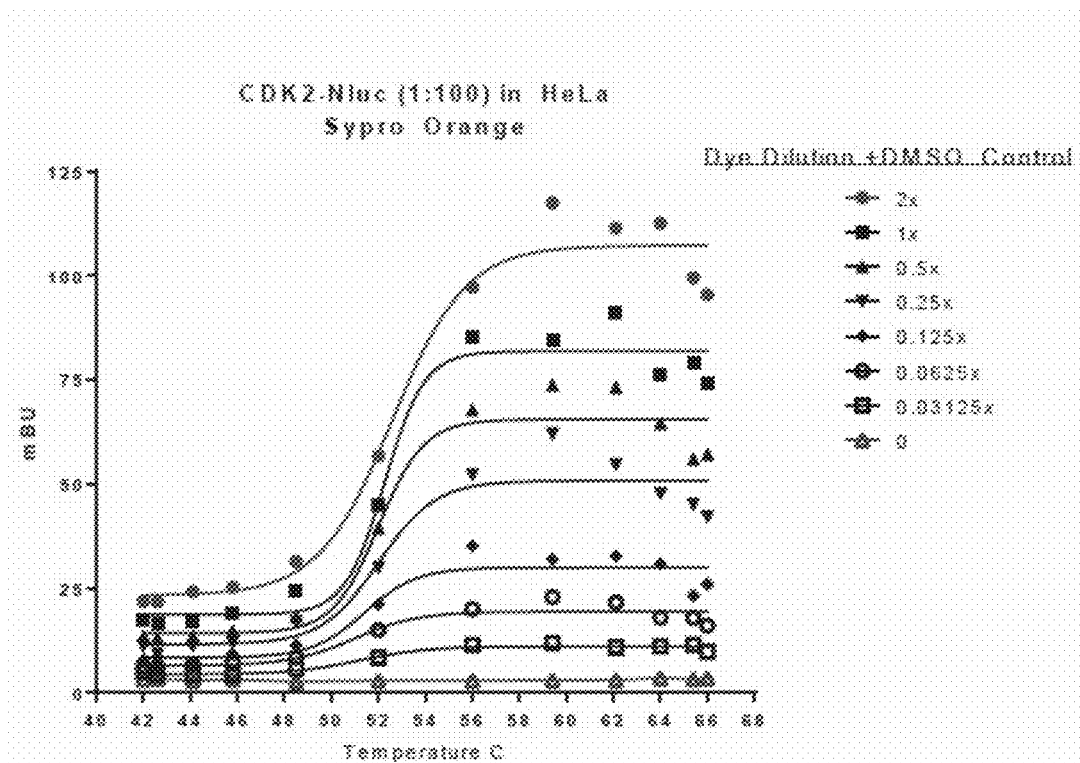
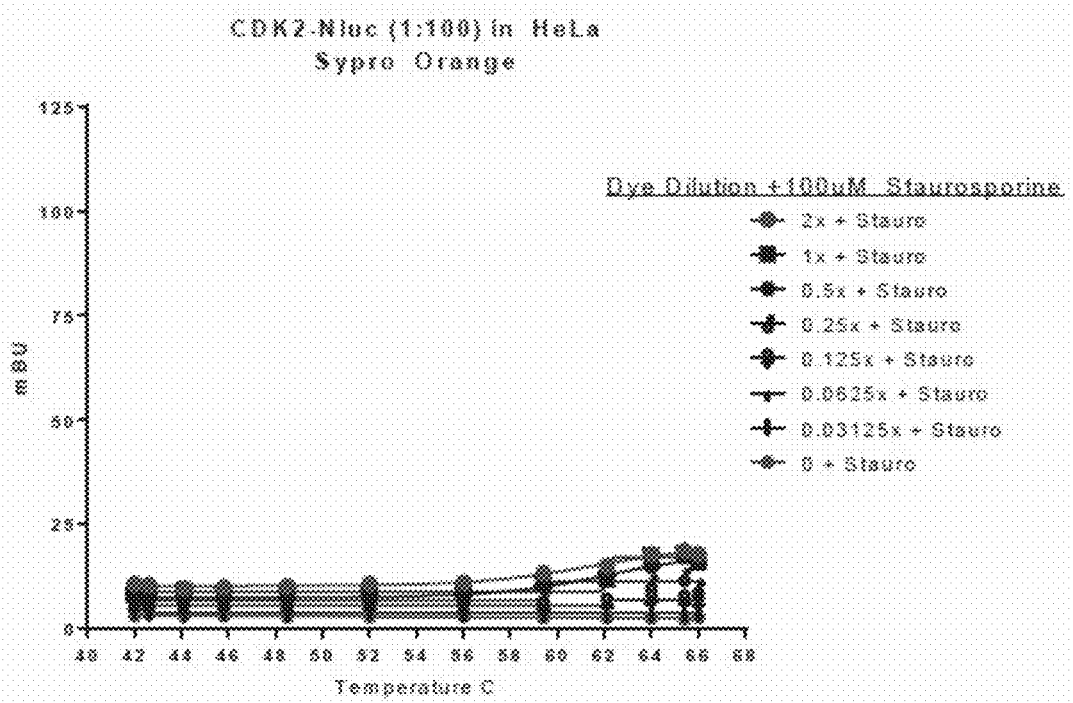

Acceptor Dye Added After Heating Step

Acceptor Dye Added Before Heating Step

FIG. 20A
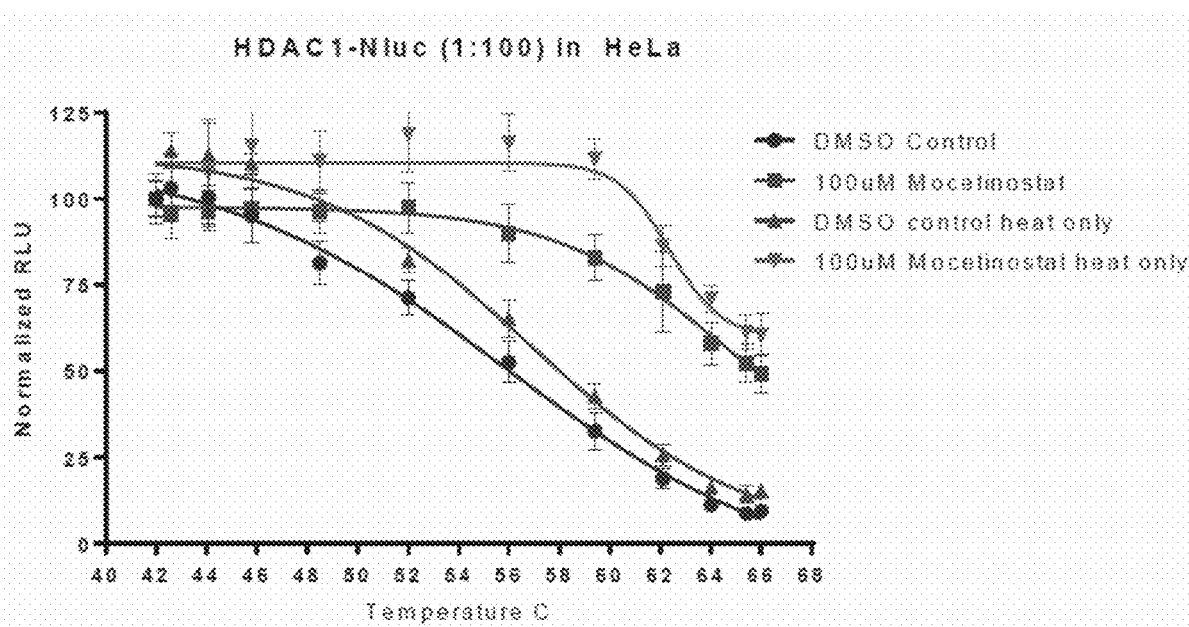
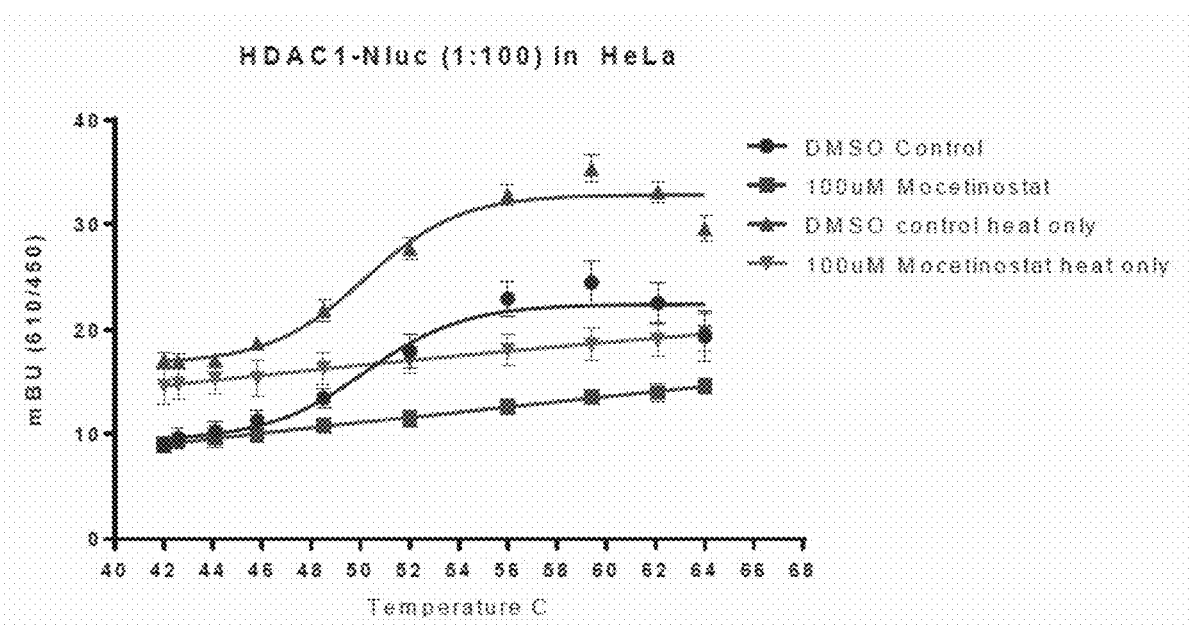
FIG. 20B

FIG. 21
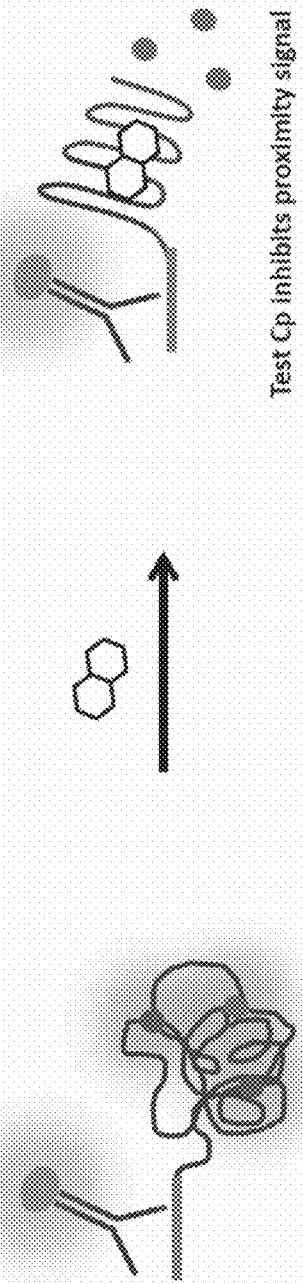
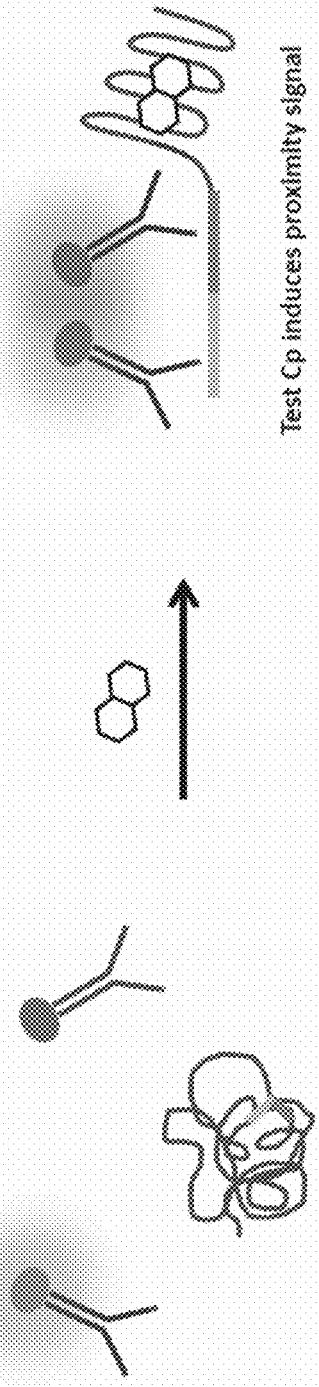

FIG. 22

Table 1: Order of Addition Examples by FIG.

| FIG. # | Digitonin | Test Ligand* | Time w/ligand (hrs) | Heat Step | Cool Step | Addition Dye | Substrate | Transfer to TC plate |
|---|---|---|---|---|---|---|---|---|
| 1 | NA | NA | NA | 1 | 2 | NA | 4 | 3 |
| 2 | 1 | NA | NA | 2 | 3 | NA | 5 | 4 |
| 3 | 2 | 1 | 1hr digi/3hr live | 3 | 4 | NA | 6 | 5 |
| 4 | NA | 1 | 2hrs | 2 | 3 | NA | 5 | 4 |
| 5 | 1 | 2 | 1HR | 3 | 4 | NA | 5 | 6 |
| 6 | 2 | 1 | 1/2HR | 3 | 4 | 5 | 6 | 7 |
| 7 | 2 | 1 | 1/2HR | 5 | 6 | 3 | 4 | 7 |
| 8 | 1 | 2 | 1-2hrs | 3 | 4 | NA | 6 | 5 |
| 9 | 1 | 2 | 1-2hrs | 3 | 4 | NA | 6 | 5 |
| 10 | 1 | 2 | 1-2hrs | 3 | 4 | NA | 6 | 5 |
| 11 | 1 | 2 | 1-2hrs | 3 | 4 | NA | 6 | 5 |
| 12 | 1 | 2 | 1hr | 3 | 4 | 5 | 6 | 7 |
| 13 | 2 | 1 | 1/2hr | 3 | 4 | 5 | 6 | 7 |
| 14 | 2 | 1 | 1/2hr | 3 | 4 | 2 | 2 | 5 |
| 15 | 2 | 1 | 1/2hr | 3 | 4 | 2 | 2 | 5 |
| 16 | 2 | 1 | 1/2hr | 3 | 4 | 2 | 2 | 5 |
| 17 | 1 | 2 | 2hrs | 3 or 4 | 4 or 5 | 6 or 3 | 7 | 5 or 6 |
| 18 | 2 | 1 | 1/2hr | 3 | Y/N 4 | 2 | 2 | 5 |
| 19 | 2 | 1 | 1/2hr | 3 | Y/N 4 | 2 | 2 | 5 |
| 20 | NA | 1 | 2 hrs then wash | 3 | 4 | NA | 6 | 5 |

\* If test ligand added first, then digitonin not added until immediately before the next step in sequence FIG. 24
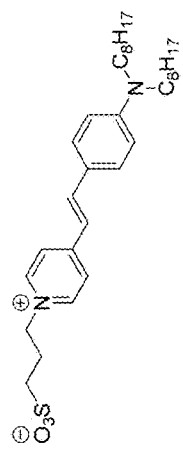
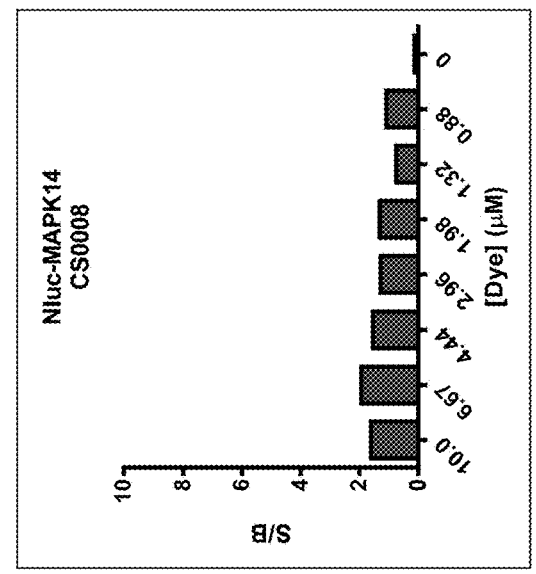
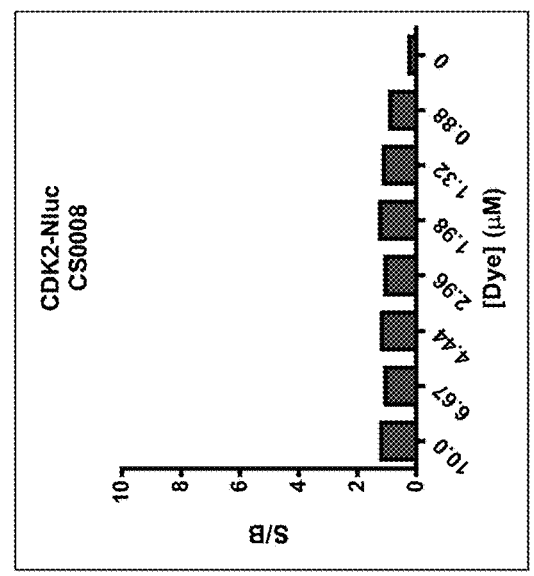
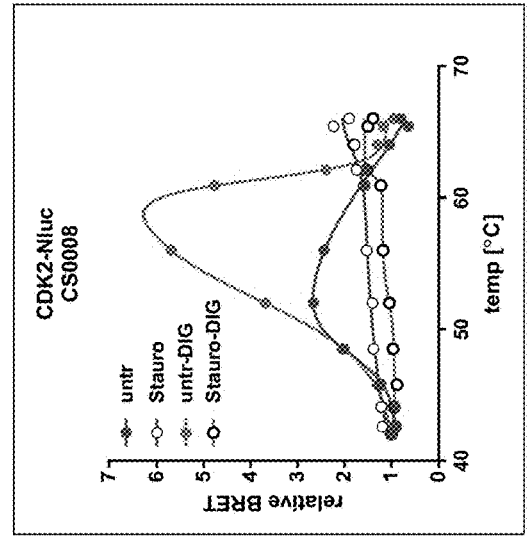

FIG. 25
CS0028
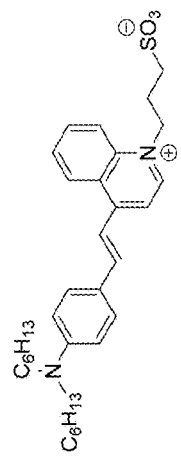
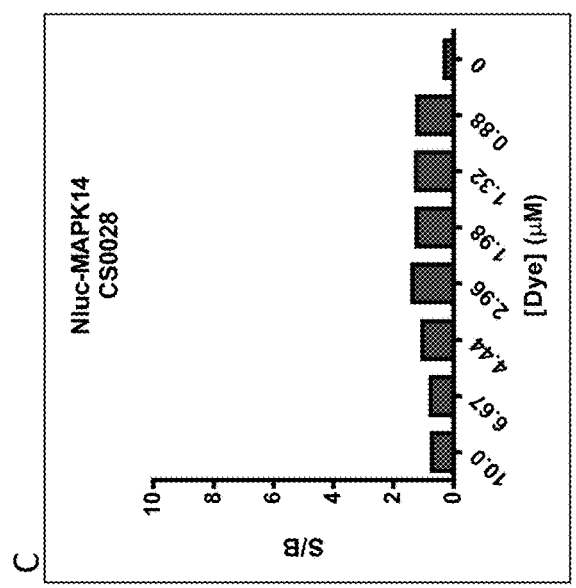
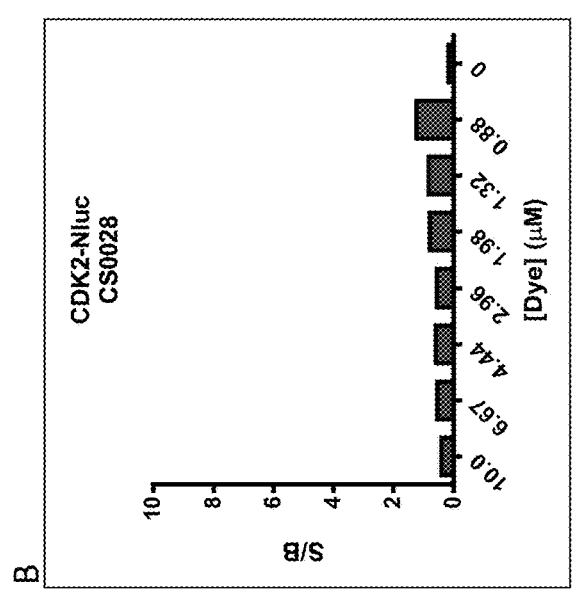
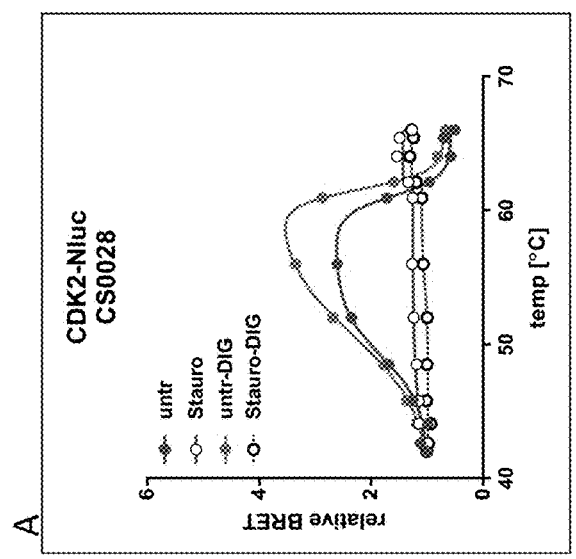

FIG. 26
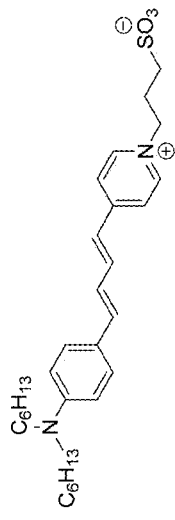
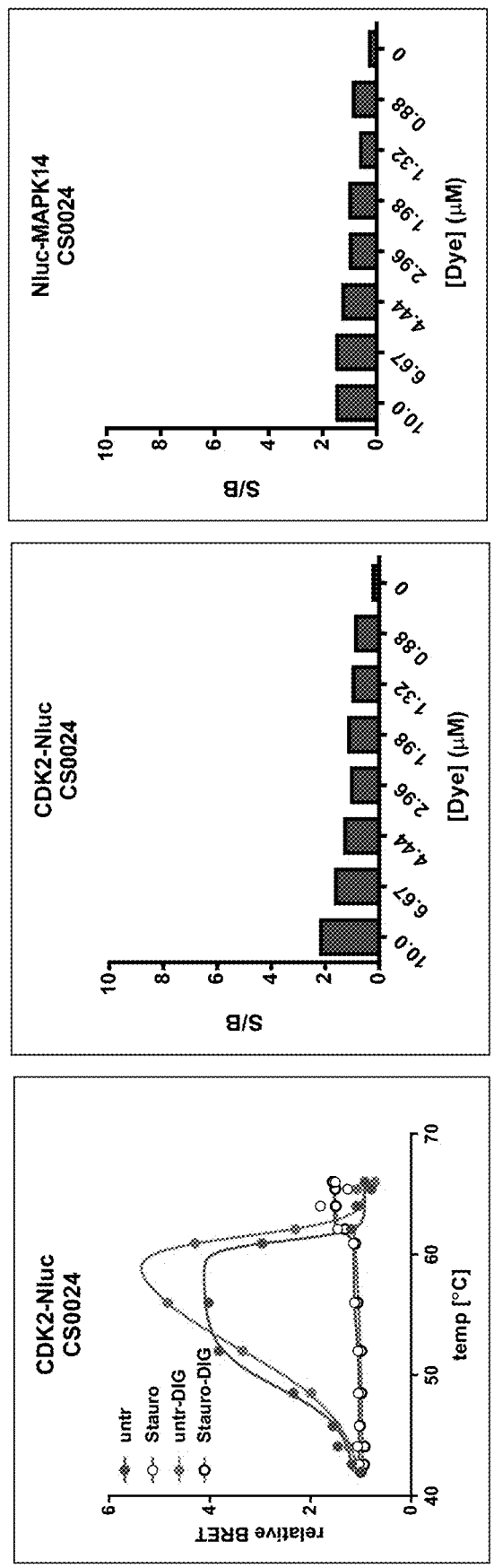

FIG. 27
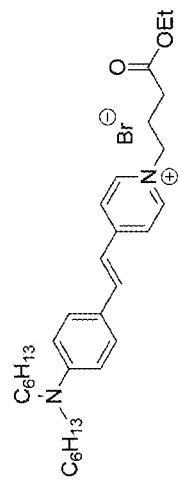
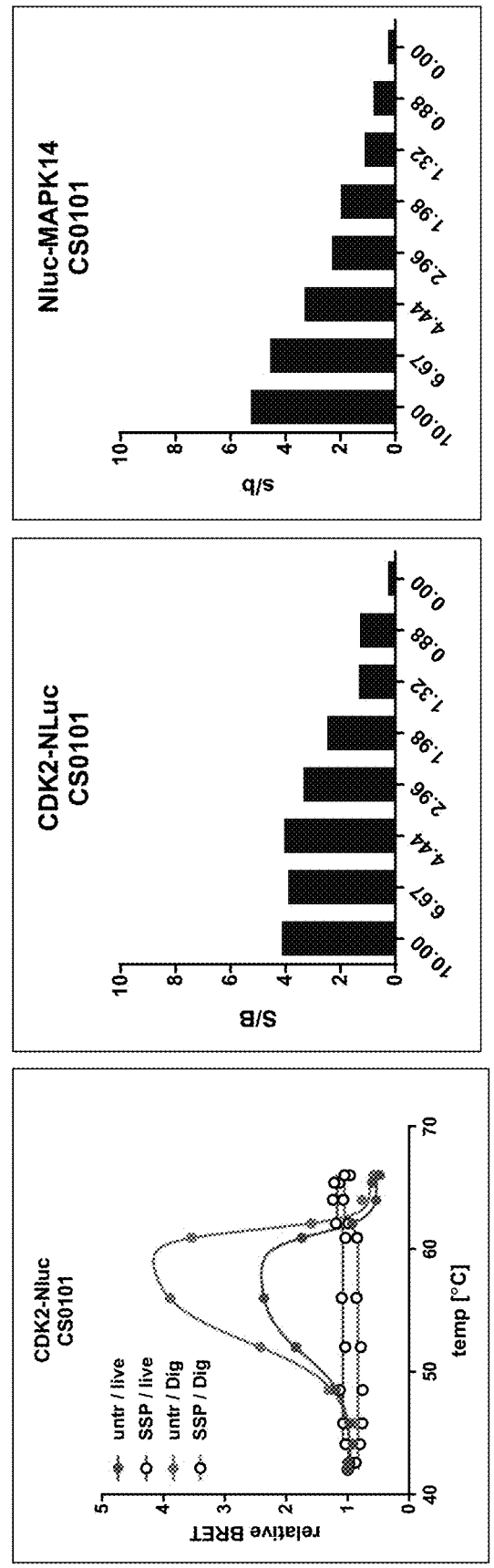

FIG. 28
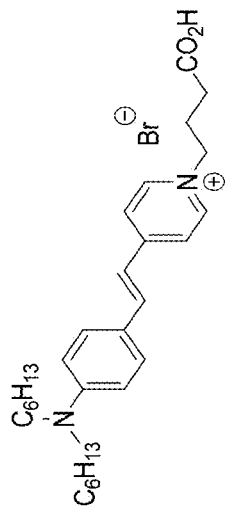
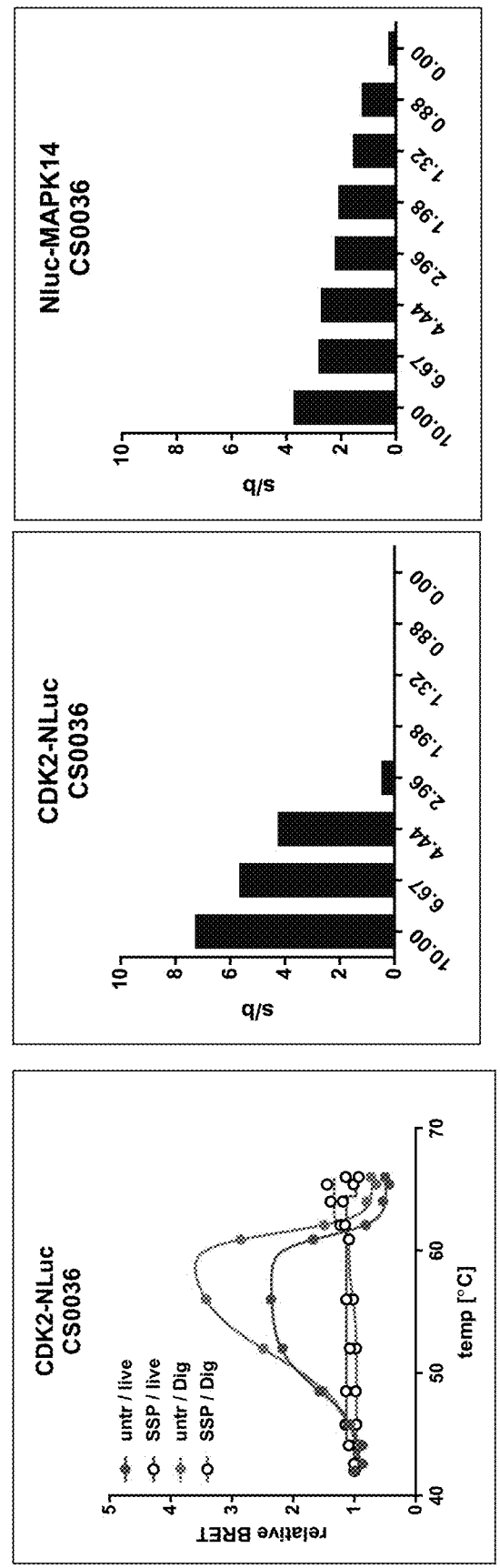

FIG. 29
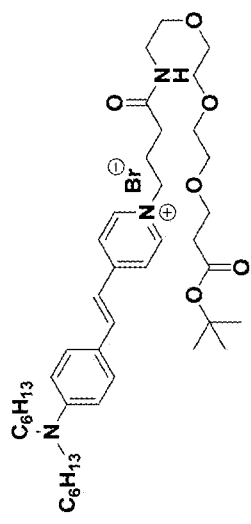
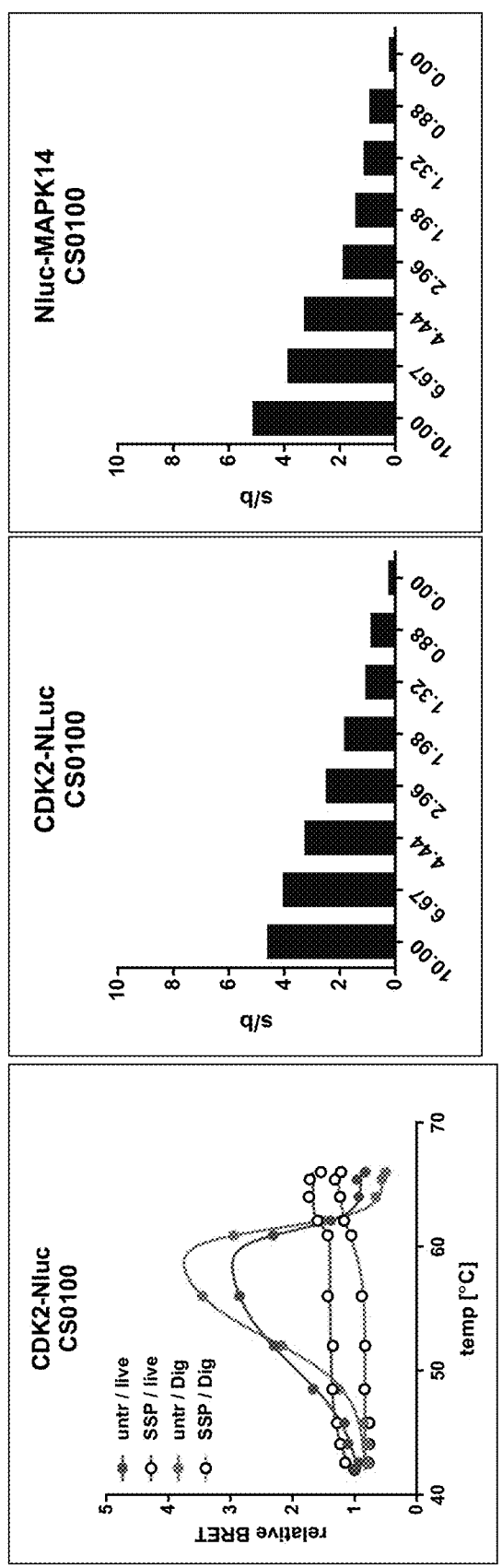

FIG. 30
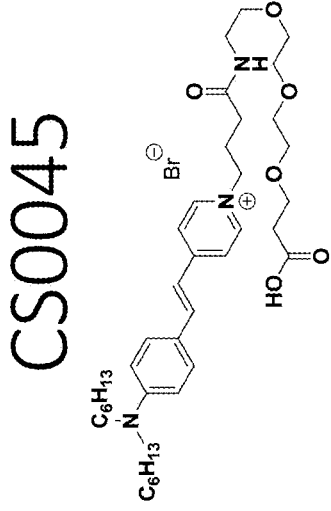
CS0045
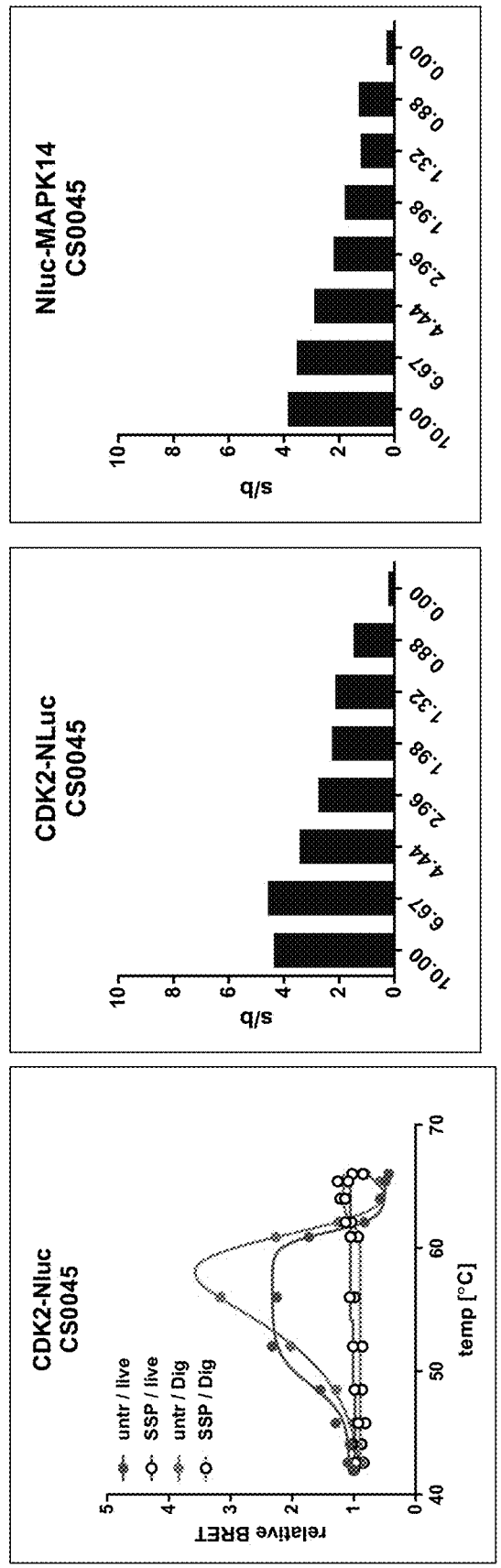

FIG. 31
CS0048
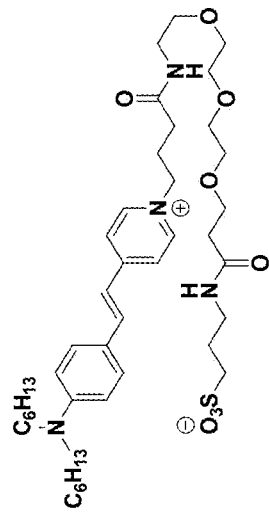
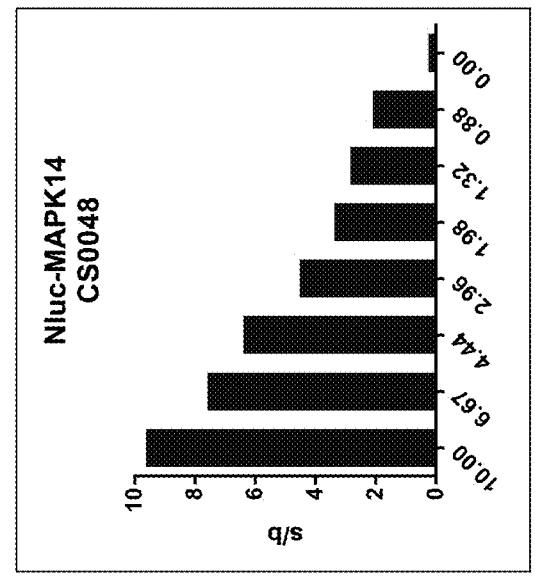
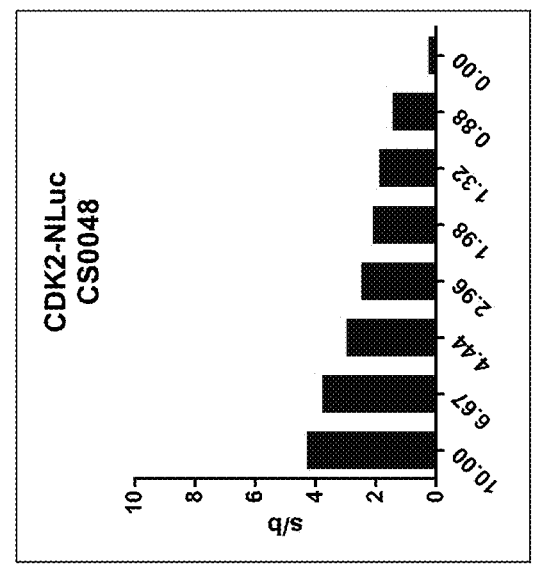
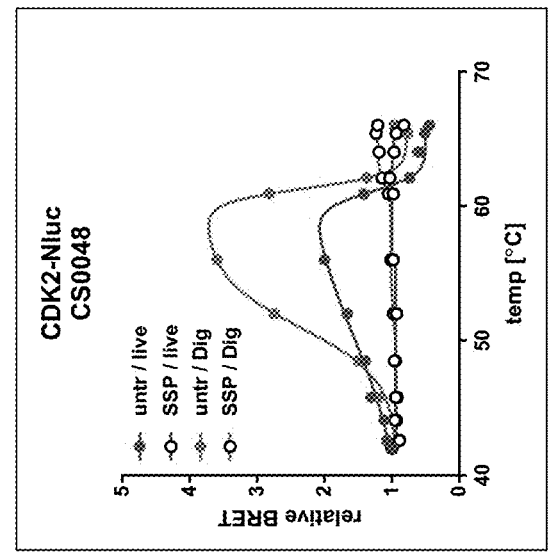

FIG. 32
CS0073
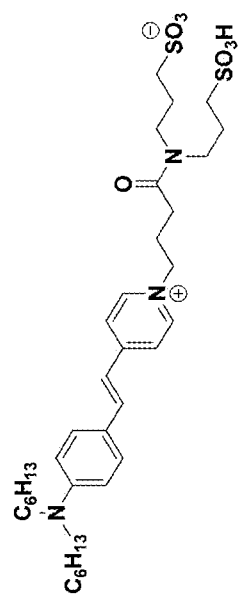
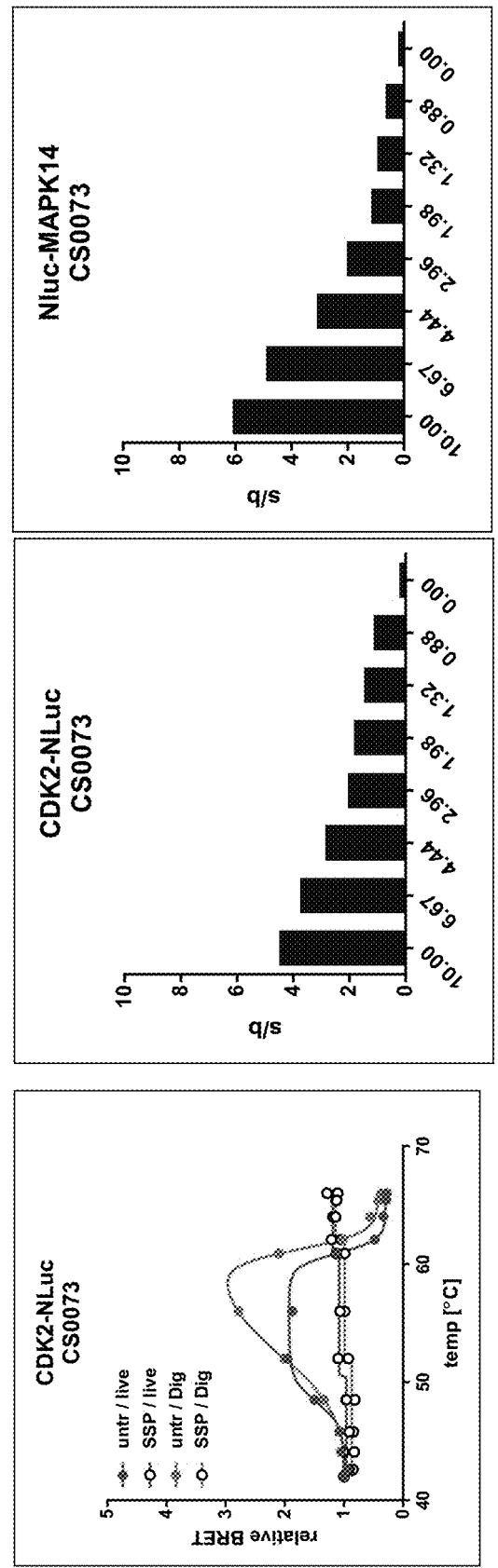

FIG. 33
CS0096
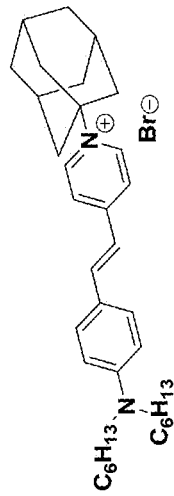
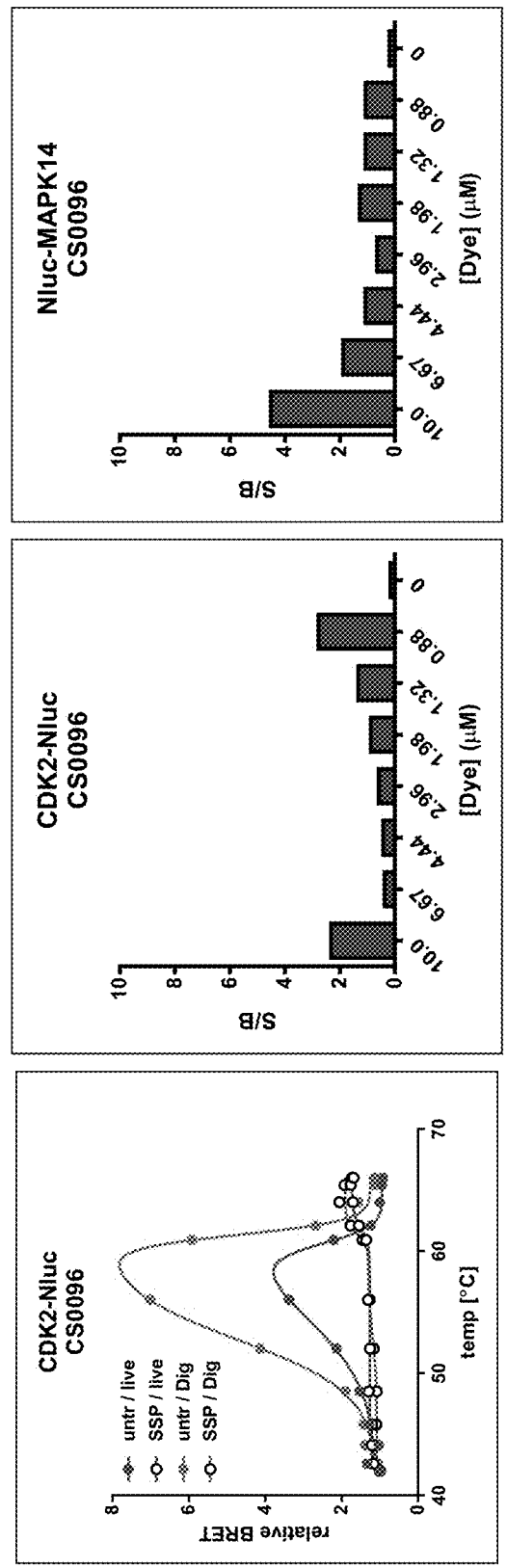

FIG. 34
CS0112
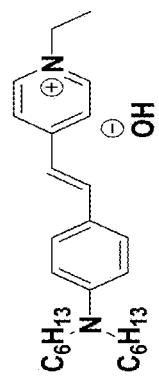
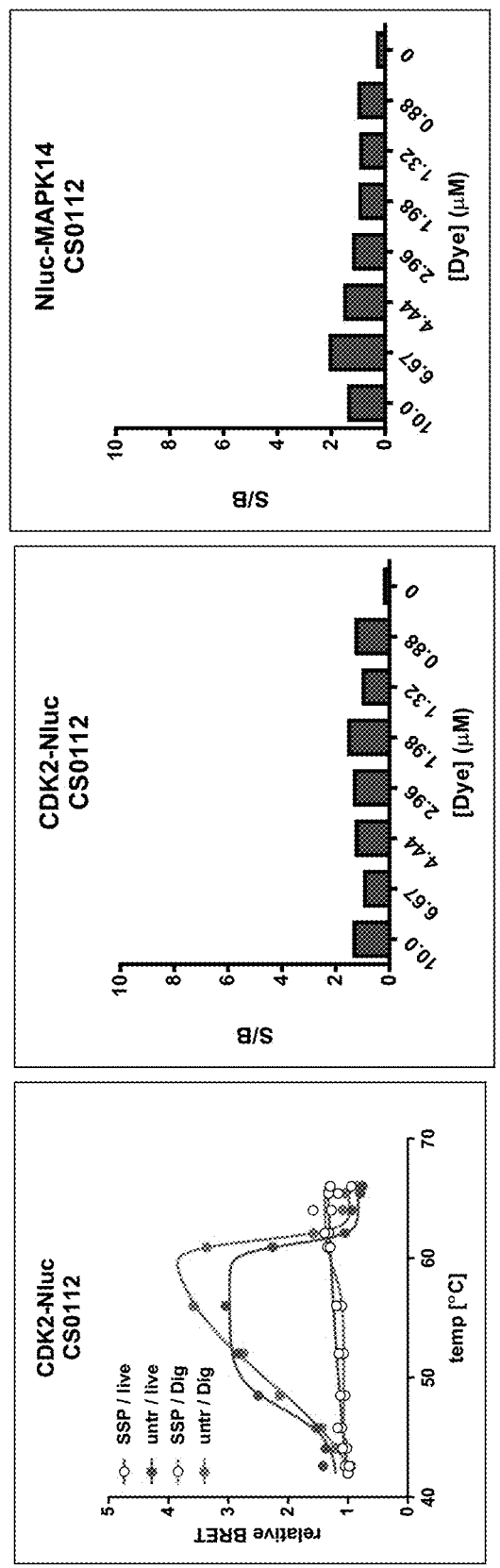

FIG. 36
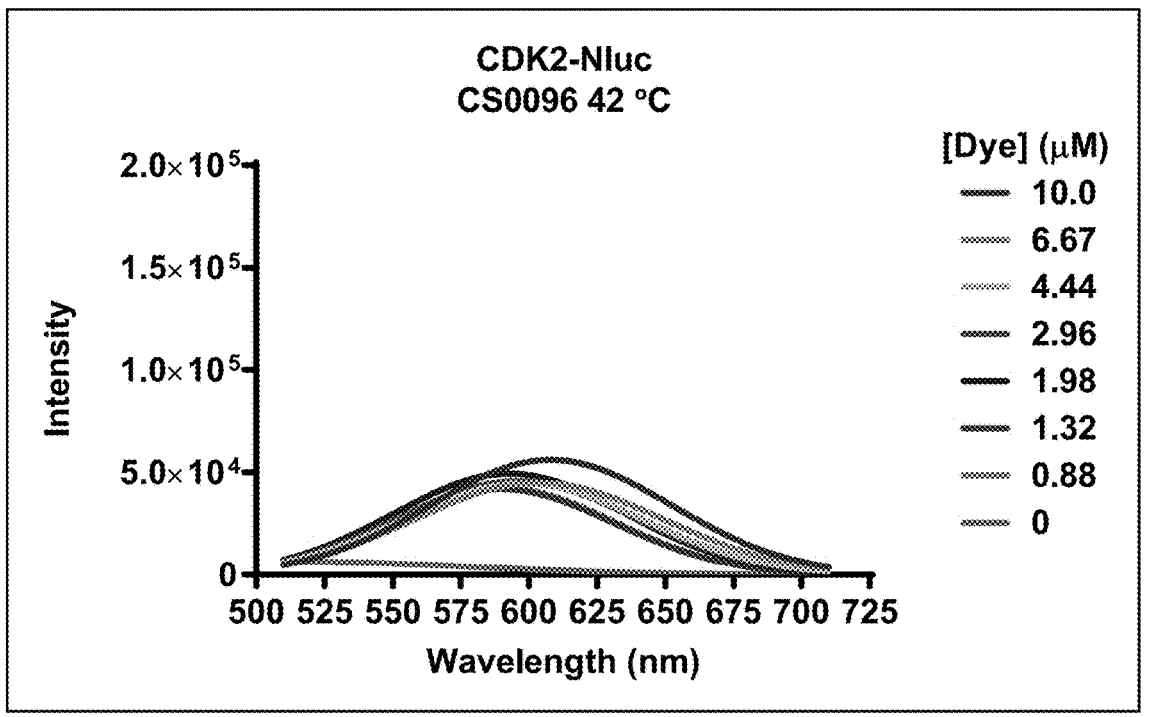
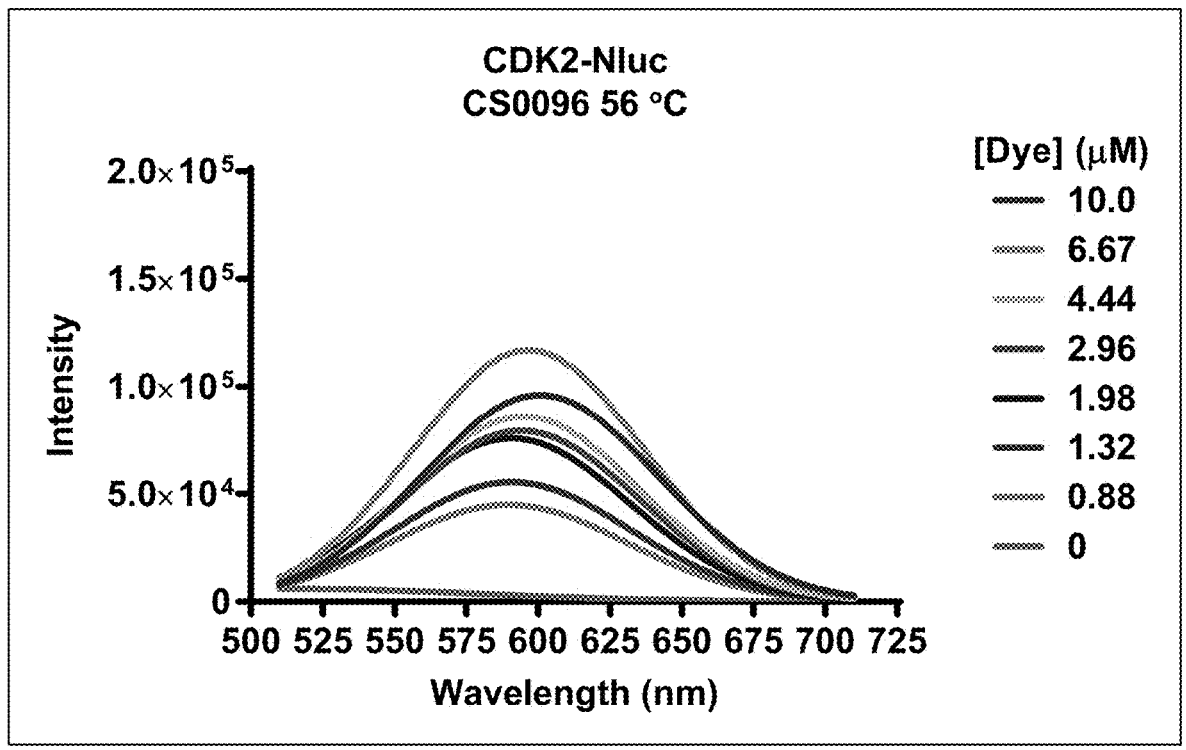

SEQUENCE LISTING

```
Sequence total quantity: 7
SEQ ID NO: 1              moltype = AA  length = 170
FEATURE                   Location/Qualifiers
source                    1..170
                          mol_type = protein
                          organism = Oplophorus gracilirostris
SEQUENCE: 1
MFTLADFVGD WQQTAGYNQD QVLEQGGLSS LFQALGVSVT PIQKVVLSGE NGLKADIHVI   60
IPYEGLSGFQ MGLIEMIFKV VYPVDDHHFK IILHYGTLVI DGVTPNMIDY FGRPYPGIAV  120
FDGKQITVTG TLWNGNKIYD ERLINPDGSL LFRVTINGVT GWRLCENILA             170

SEQ ID NO: 2              moltype = AA  length = 171
FEATURE                   Location/Qualifiers
source                    1..171
                          mol_type = protein
                          organism = synthetic construct
SEQUENCE: 2
MVFTLEDFVG DWRQTAGYNL DQVLEQGGVS SLFQNLGVSV TPIQRIVLSG ENGLKIDIHV   60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGT GWRLCERIL A            171

SEQ ID NO: 3              moltype = AA  length = 13
FEATURE                   Location/Qualifiers
source                    1..13
                          mol_type = protein
                          organism = synthetic construct
SEQUENCE: 3
GVTGWRLCER ILA                                                      13

SEQ ID NO: 4              moltype = AA  length = 158
FEATURE                   Location/Qualifiers
source                    1..158
                          mol_type = protein
                          organism = synthetic construct
SEQUENCE: 4
MVFTLADFVG DWQQTAGYNQ DQVLEQGGLS SLFQALGVSV TPIQKVVLSG ENGLKADIHV   60
IIPYEGLSGF QMGLIEMIFK VVYPVDDHHF KIILHYGTLV IDGVTPNMID YFGRPYPGIA  120
VFDGKQITVT GTLWNGNKIY DERLINPDGS LLFRVTIN                          158

SEQ ID NO: 5              moltype = AA  length = 11
FEATURE                   Location/Qualifiers
source                    1..11
                          mol_type = protein
                          organism = synthetic construct
SEQUENCE: 5
VSGWRLFKKI S                                                        11

SEQ ID NO: 6              moltype = AA  length = 159
FEATURE                   Location/Qualifiers
source                    1..159
                          mol_type = protein
                          organism = synthetic construct
SEQUENCE: 6
MVFTLEDFVG DWEQTAAYNL DQVLEQGGVS SLLQNLAVSV TPIQRIVRSG ENALKIDIHV   60
IIPYEGLSAD QMAQIEEVFK VVYPVDDHHF KVILPYGTLV IDGVTPNMLN YFGRPYEGIA  120
VFDGKKITVT GTLWNGNKII DERLITPDGS MLFRVTINS                         159

SEQ ID NO: 7              moltype = AA  length = 158
FEATURE                   Location/Qualifiers
source                    1..158
                          mol_type = protein
                          organism = synthetic construct
SEQUENCE: 7
MVFTLEDFVG DWRQTAGYNL DQVLEQGGVS SLFQNLGVSV TPIQRIVLSG ENALKIDIHV   60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTIN                          158
```

LUCIFERASE-BASED THERMAL SHIFT ASSAYS

CROSS-REFERENCE TO RELATED APPLICATIONS

The present application is a continuation of U.S. patent application Ser. No. 17/105,024, filed on Nov. 25, 2020, now allowed, which is a continuation of U.S. patent application Ser. No. 16/787,950, filed Feb. 11, 2020, now U.S. Pat. No. 10,928,400, which is a divisional of U.S. patent application Ser. No. 15/017,271, filed Feb. 5, 2016, now U.S. Pat. No. 10,571,741, which claims the priority benefit of U.S. Provisional Patent Application 62/112,518, filed Feb. 5, 2015, each of which is incorporated by reference in its entirety.

SEQUENCE LISTING

The text of the computer readable sequence listing filed herewith, titled "34095-305 SEQUENCE LISTING", created Jan. 4, 2023, having a file size of 7,869 bytes, is hereby incorporated by reference in its entirety.

FIELD

Provided herein are systems and methods for characterizing target/ligand engagement. In particular, luciferase-labeled polypeptide targets are used to detect or quantify target/ligand engagement (e.g., within a cell or cell lysate).

BACKGROUND

Multiple challenges face drug development today including high costs and long development cycles for new therapeutics. Methods that promote accelerated drug development are urgently needed. The efficacy of therapeutics is dependent on a drug binding to its target. Due to its simplicity, a protein thermal shift assay (TSA) is a commonly used method for screening libraries and validating hits in drug discovery programs. The most common method of TSA in use today can only be performed using purified protein, which has several disadvantages. Recently, the cellular thermal shift assay (CETSA) was developed to detect endogenous target protein within cells or cell lysates, thereby alleviating the need to create purified proteins and allowing for target engagement analysis in complex environments that are more biologically relevant. However, the CETSA is a multi-step assay in which the analysis of target engagement relies upon western blot or AlphaScreen (Perkin Elmer) technologies, both of which have several disadvantages, e.g., cost, insensitive, multi-stepped protocols, requires cell lysis and spin steps, low throughput (e.g., Western blot), dependent upon antibody recognition of native protein state, cell line optimization, requires a large amount of cells, etc. What is needed is a simple, homogeneous, rapid, and inexpensive TSA, whereby target engagement can be characterized in complex environments, such as cells and cell lysate.

SUMMARY

Provided herein are systems and methods for characterizing target/ligand engagement. In particular, luciferase-labeled polypeptide targets are used to detect or quantify target/ligand engagement (e.g., within a cell, e.g., in an intact live cell, or cell lysate).

In some embodiments, provided herein are systems comprising: (a) a fusion of a target protein and a bioluminescent reporter; and (b) a fluorescent dye; wherein the bioluminescent reporter and the fluorescent dye comprise a bioluminescence resonance energy transfer BRET pair (e.g., the bioluminescent reporter is the BRET donor and the fluorescent dye is the BRET acceptor); and wherein the fluorescent dye interacts with exposed hydrophobic regions of the target protein upon unfolding, denaturation, and/or aggregation of the target protein. In some embodiments, the fluorescent dye does not interact with the natively folded (or otherwise stably folded) target protein. In some embodiments, the fluorescent dye binds to the unfolded or partially unfolded target protein significantly more than to the folded target protein (e.g., 2-fold increase, 3-fold increase, 4-fold increase, 5-fold increase, 6-fold increase, 7-fold increase, 8-fold increase, 9-fold increase, 10-fold increase, 20-fold increase, 50-fold increase, 100-fold increase, 1000-fold increase, or more, or ranges therein). In some embodiments, systems further comprise a ligand or test ligand for the target protein. In some embodiments, systems further comprise a substrate for the bioluminescent reporter.

In some embodiments, provided herein are systems comprising: (a) a fusion of a target protein and a bioluminescent reporter, wherein the bioluminescent reporter protein has an emission spectra that encompasses a wavelength X; and (b) a fluorescent dye that: (1) binds nonspecifically to aggregated proteins and/or hydrophobic peptide segments, and (2) has an excitation spectra that encompasses the wavelength X. In some embodiments, the emission spectra of the bioluminescent reporter protein and the excitation spectra of the fluorescent dye overlap such that the bioluminescent reporter excites the fluorescent dye by BRET. In some embodiments, the bioluminescent reporter and the fluorescent dye comprise a BRET pair. In some embodiments, the bioluminescent reporter is a BRET donor, and the fluorescent dye is a BRET acceptor. In some embodiments, the system is a cell, e.g., a live, intact cell, cell lysate (e.g., cells lysed by chemical methods (e.g., lytic NANOGLO reagent, cells lysed by sonication, etc.), or reaction mixture. In some embodiments, the bioluminescent reporter is a luciferase. In some embodiments, the luciferase is a variant *Oplophorus gracilirostris* luciferase (OgLuc) (e.g., >60%, 70%, 80%, 90%, or 95% identity with SEQ ID NO: 1, SEQ ID NO: 2, etc.). In some embodiments, the bioluminescent reporter is a peptide or polypeptide tag that forms a bioluminescent complex upon interaction with a complement polypeptide or peptide (See, e.g., U.S. Pub. No. 2014/0363375; herein incorporated by reference in its entirety). In some embodiments, the system further comprises complement polypeptide or peptide that forms a bioluminescent reporter with the target portion of the fusion. In some embodiments, provided herein are compositions and methods for the assembly of a bioluminescent complex from two or more non-luminescent (e.g., substantially non-luminescent) peptide and/or polypeptide units. In particular, bioluminescent activity is conferred upon a non-luminescent polypeptide via structural complementation with another, complementary non-luminescent peptide. As used herein the term "complementary" refers to the characteristic of two or more structural elements (e.g., peptide, polypeptide, nucleic acid, small molecule, etc.) of being able to hybridize, dimerize, or otherwise form a complex with each other. For example, a "complementary peptide and polypeptide" are capable of coming together to form a complex. In some embodiments, the fluorescent dye is an environmentally-sensitive dye. In some embodiments, the fluorescent dye is hydrophobic. In some embodiments, the fluorescence of the fluorescent dye is quenched by water (e.g., fluorescence is suppressed when the dye is free in aqueous solution and enhanced when the dye is in a hydrophobic environment). In some embodiments, the fluorescent dye is fluorogenic. In some embodiments, binding between the fluorescent dye and the reporter protein is altered by changes in target protein structure (e.g., unfolding). In some embodiments, the fluorescence of the fluorescent dye is quenched or suppressed when free in aqueous solution and enhanced when the dye bound to a hydrophobic composition. In some embodiments, the fluorescent dye is SYPRO Orange, SYPRO Red, Nile Red, ANS, Bis-ANS, SYPRO Ruby, SYPRO Tangerine, and/or Dapoxyl Sulfonic Acid Sodium Salt, PROTEIN THERMAL SHIFT Dye (Life Technologies), PROTEOSTAT Dye (Enzo), or combinations thereof. In some embodiments, the system further comprises a ligand of the target or a test ligand.

In some embodiments, methods are provided for detecting the interaction of a ligand and target protein based upon the stabilization of the target protein upon formation of a target/ligand complex comprising: (a) incubating a fusion of the target protein and a bioluminescent reporter with a substrate for the bioluminescent reporter and a fluorescent dye that binds to hydrophobic peptide sequences when they are exposed by protein unfolding; and (b) detecting BRET from the bioluminescent reporter to the fluorescent dye in the presence and absence of the ligand or test ligand. In some embodiments, signal is detected over a range of denaturing conditions (e.g., two or more conditions (e.g., ranging from non-denaturing to highly-denaturing)). In some embodiments, due to the proximity limitation of BRET (e.g., donor to acceptor distance of about 1-10 nm), emission from the fluorescent dye as a consequence of BRET from the bioluminescent reporter is only detected when the fluorescent dye is bound to the target protein. In some embodiments, binding of the ligand or test ligand to the target protein stabilizes the protein and increases the degree of the denaturing conditions (e.g., temperature, concentration of denaturant, increased pressure, etc.) required to unfold the target protein, allow binding of the fluorescent or fluorogenic dye to the exposed hydrophobic portions of the target protein, producing a detectable signal resulting from BRET from the bioluminescent reporter to the target-bound fluorescent dye. In some embodiments, the fusion, fluorescent dye, substrate, and ligand (when present) are combined in any suitable order of addition.

In some embodiments, provided herein are methods to detect a target/ligand interaction, comprising the steps of: (a) incubating a fusion of a target protein and a reporter polypeptide: (i) in the presence of a ligand to produce a test sample and (ii) in the absence of a ligand to produce a control sample; (b) treating said test and control samples under conditions that cause the target protein to unfold (e.g., to an appropriate extent); (c) measuring signal from the reporter polypeptide in said test and control samples; and (d) comparing the measurement made in step (c) between the test and control samples, wherein alteration of the signal from said reporter polypeptide in the test sample compared to the control sample indicates the presence of a target/ligand interaction. In some embodiments, the fusion is within a cell, e.g., a live, intact cell, cell lysate, or reaction mixture. In some embodiments, the fusion is expressed within the cell, e.g., a live intact cell, cell lysate, or reaction mixture. In some embodiments, the ligand is added exogenously to the cell, e.g., a live intact cell, cell lysate, or reaction mixture. In some embodiments, the reporter polypeptide is a luciferase. In some embodiments, the luciferase is a variant *Oplophorus gracilirostris* luciferase (OgLuc) (e.g., >60%, 70%, 80%, 90%, or 95% identity with SEQ ID NO: 1, SEQ ID NO: 2, etc.). In some embodiments, the bioluminescent reporter is a peptide or polypeptide tag that forms a bioluminescent complex upon interaction with a complement polypeptide or peptide (See, e.g., U.S. Pub. No. 2014/0348747; herein incorporated by reference in its entirety). In some embodiments, the complement polypeptide or peptide is added exogenously to the test and control samples prior to step (c). In some embodiments, the complement polypeptide or peptide is expressed within the cell, cell lysate, or reaction mixture. In some embodiments, the conditions that cause the target protein to unfold to an appropriate extent comprise elevated temperature, increased pressure, and/or a denaturant. In some embodiments, elevated temperature comprises one or more temperatures above physiologic temperature for the protein in question. In some embodiments, elevated temperature comprises one or more temperatures near (e.g., +/−1, 2, 3, 4, 5, 10, 15, 20° C.) the approximate melting temperature of the target protein. In some embodiments, a plurality of test samples is produced using a plurality of test ligands.

In some embodiments, provided herein are methods to detect a target/ligand interaction, comprising the steps of: (a) incubating a fusion of a target protein and a bioluminescent reporter: (i) in the presence of a ligand to produce a test sample, and (ii) in the absence of a ligand, to produce a control sample; (b) contacting the test and control samples with an environmentally-sensitive hydrophobic dye, wherein the emission spectra of the bioluminescent reporter and the excitation spectra of the environmentally-sensitive hydrophobic dye overlap; (c) treating said test and control samples under conditions that cause the target protein to unfold to an appropriate extent; (d) measuring signal from the environmentally-sensitive hydrophobic dye in said test and control samples (e.g., emission resulting from energy transfer from the active bioluminescent reporter after addition of substrate); and (e) comparing the measurement made in step (d) between the test and control samples, wherein alteration of the signal from said environmentally-sensitive hydrophobic dye in the test sample compared to the control sample indicates the presence of a target/ligand interaction. In some embodiments, steps (a), (b), and (c) are performed in any suitable order (e.g., a-b-c, a-c-b, b-a-c, b-c-a, c-a-b, or c-b-a). In some embodiments, the fusion is within a cell, e.g., a live intact cell, cell lysate, or reaction mixture. In some embodiments, the fusion is expressed within the cell, e.g., a live intact cell, cell lysate, or reaction mixture. In some embodiments, the ligand is added exogenously to the cell, e.g., a live intact cell, cell lysate, or reaction mixture. In some embodiments, the environmentally-sensitive hydrophobic dye is added exogenously to the cell, e.g., a live intact cell, cell lysate, or reaction mixture. In some embodiments, the bioluminescent reporter is a luciferase. In some embodiments, the luciferase is a variant *Oplophorus gracilirostris* luciferase (OgLuc) (e.g., >60%, 70%, 80%, 90%, or 95% identity with SEQ ID NO: 1, SEQ ID NO: 2, etc.). In some embodiments, the bioluminescent reporter is a peptide or polypeptide tag that forms a bioluminescent complex upon interaction with a complement polypeptide or peptide. In some embodiments, the complement polypeptide or peptide is added exogenously to the test and control samples prior to step (d). In some embodiments, the complement polypeptide or peptide is expressed within the cell, e.g., a live intact cell, cell lysate, or reaction mixture. In some embodiments, the conditions that cause the target protein to unfold to an appropriate extent comprise elevated temperature, increased pressure, and/or a denaturant. In some embodiments, elevated temperature comprises one or more temperatures above physiologic temperature. In some embodiments, elevated temperature comprises one or more temperatures near the approximate melting temperature of the target protein. In some embodiments, the environmentally-sensitive hydrophobic dye binds nonspecifically to hydrophobic surfaces. In some embodiments, the environmentally-sensitive hydrophobic dye binds preferentially to the folded, unfolded, or molten globule states of the protein. In some embodiments, the fluorescence of the environmentally-sensitive hydrophobic dye is quenched by water. In some embodiments, the environmentally-sensitive hydrophobic dye is Sypro Orange, SYPRO Red, Nile Red, ANS, Bis-ANS, SYPRO Ruby, SYPRO Tangerine, and/or Dapoxyl Sulfonic Acid Sodium Salt, Protein Thermal Shift™ Dye (Life Technologies), PROTEOSTAT Dye (Enzo), or combinations thereof. Other suitable dyes for use in embodiments described herein include, but are not limited to: styryl dyes, asymmetric cyanines, oxazole dyes (Dapoxyls), azo dyes, and other dyes such as Thioflavin T and (Dicyanovinyl)julolidine (DCVJ). Suitable dyes for use in embodiments described herein are also described in, for example: Kovalska et al. Dyes and Pigments 67 (2005) 47-54; Volkova et al. Bioorganic & Medicinal Chemistry 16 (2008) 1452-1459; Volkova et al. J. Biochem. Biophys. Methods 70 (2007) 727-733; Hawe et al. Pharmaceutical Research, Vol. 25, No. 7, July 2008; U.S. Pub. No. 2011/0130305; PCT Pub. WO 2006/079334; Diwu et al. Photochemistry and Photobiology, 1997, 66(4): 424-431; herein incorporated by reference in their entireties.

In some embodiments, methods of screening a group of test ligands for interaction with a target protein are provided. In some embodiments, a fusion of the target protein and a bioluminescent reporter is combined with a fluorescent dye that binds to exposed hydrophobic portions of proteins (e.g., upon exposure of the hydrophobic portions due to protein denaturation) and a substrate for the bioluminescent reporter, in the presence and absence of one or more of the test ligands. In some embodiments, multiple assays, each comprising a different test ligand of set of test ligands are performed in parallel (e.g., in a high throughput method). Fluorescence emission from the fluorescent dye as a result of BRET from the bioluminescent reporter is detected. Decrease of BRET-induced fluorescence in the presence of the one or more test ligands, and/or an increase in the temperature or amount of denaturant required to generate a BRET-induced fluorescent signal, indicates interaction of one or more of the test ligands with the target protein.

In some embodiments, provided herein are methods of screening a group of test ligands for binding to a target protein comprising: (a) creating a plurality of test samples each comprising at least one test ligand and a fusion of a target protein and a bioluminescent reporter; (b) creating at least one control sample comprising a fusion of a target protein and a bioluminescent reporter in the absence of a test ligand; (c) contacting the test and control samples with an environmentally-sensitive hydrophobic dye, wherein the emission spectra of the bioluminescent reporter and the excitation spectra of the environmentally-sensitive hydrophobic dye overlap; (d) treating the test and control samples under conditions that cause the target protein to unfold to an appropriate extent; (e) exposing the test and control samples to the substrate of the bioluminescent reporter; (f) measuring signal from the environmentally-sensitive hydrophobic dye in said test and control samples; and (g) comparing the measurement made in step (f) between the test and control samples, wherein alteration of the signal from said environmentally-sensitive hydrophobic dye in one or more test samples compared to the control sample indicates the presence of a target/ligand interaction.

In some embodiments, provided herein are methods to detect a target/ligand interaction, comprising the steps of: (a) incubating a fusion of a target protein and a reporter polypeptide in the presence of a ligand to produce a test sample; (b) treating said test sample under conditions that cause the target protein to unfold to an appropriate extent; (c) measuring signal from the reporter polypeptide in said test sample; and (d) detecting target/ligand interaction based on the signal from said reporter polypeptide in the test sample.

In some embodiments, provided herein are methods to detect a target/ligand interaction, comprising the steps of: (a) incubating a fusion of a target protein and a bioluminescent reporter in the presence of a ligand to produce a test sample; (b) contacting the test sample with an environmentally-sensitive hydrophobic dye, wherein the emission spectra of the bioluminescent reporter and the excitation spectra of the environmentally-sensitive hydrophobic dye overlap; (c) treating the test sample under conditions that cause the target protein to unfold to an appropriate extent; (d) exposing the test sample to the substrate of the bioluminescent reporter; (e) measuring signal from the environmentally-sensitive hydrophobic dye in said test sample; and (f) detecting target/ligand interaction based on the signal from said environmentally-sensitive hydrophobic dye in the test sample.

Based on the successful use of a direct luciferase fusion or BRET to detect ligand-mediated thermal stabilization, other proximity-based reporter chemistries are understood to be useful. For example, in certain embodiments, an epitope tag is attached to the protein of interest. Following a thermal denaturation step, addition of a detection antibody labeled with a donor fluorophore (e.g., terbium, europium, etc.) is used in a FRET assay with a denaturation/aggregation-sensitive dye as a FRET acceptor. Ligand-mediated thermal stabilization results in a loss of FRET/TR-FRET signal. In other embodiments, a combination of labeled antibodies (e.g. donor-labeled anti-FLAG and acceptor labeled anti-V5) and a tandem epitope (e.g. FLAG-V5) tethered to the target protein are used as a detection system. When stabilized, the target is stabilized by binding of a ligand, the epitope is presented and both antibodies bind, generating a proximity-based signal (e.g. FRET, TR-FRET). Upon thermal denaturation, the epitopes are unavailable to the antibody pair, resulting in a loss of proximity-based signal. In some embodiments, various detection chemistries are applied (e.g. TR-FRET, proximity ligation, singlet oxygen transfer/alphascreen, etc.).

In some embodiments, methods are provided for the detection of target/ligand interactions within a cell. In some embodiments, methods allow detection of target/ligand interactions within live, intact cells. In some embodiments, all steps (e.g., target/reporter expression, reagent (e.g., ligand, substrate, dye, etc.) addition, target denaturation, signal detection, etc.) are performed to or within the live, intact cells. In some embodiments, the target/ligand interaction is initiated within the live, intact cells, but one or more steps of the assay (e.g., substrate addition, target denaturation, signal detection, etc.) are performed in a lysate of the cells (e.g., following lysis of the live, intact cells to produce a cell lysate). In some embodiments, all steps (e.g., target/reporter expression, reagent (e.g., ligand, substrate, dye, etc.) addition, target denaturation, signal detection, etc.) are performed to or within the cell lysate. The following paragraphs provide exemplary methods for performing such assays. The following embodiments are not limiting, and may be combined and/or modified with other embodiments described herein.

In some embodiments, provided herein are methods to detect a target/ligand interaction within a live, intact cell, comprising the steps of: (a) providing a live, intact cell expressing a fusion of a target protein and a bioluminescent reporter; (b) allowing time for the target protein to interact with the ligand within the live, intact cell; (c) contacting the live, intact cell with an environmentally-sensitive hydrophobic dye, wherein the emission spectra of the bioluminescent reporter and the excitation spectra of the environmentally-sensitive hydrophobic dye overlap; (d) treating the live, intact cell under conditions that cause the target protein to unfold to an appropriate extent; (e) exposing the live, intact cell to the substrate of the bioluminescent reporter; (f) measuring signal from the environmentally-sensitive hydrophobic dye and bioluminescent reporter in the live, intact cell; and (g) detecting target/ligand interaction based on the ratio from the signals from said environmentally-sensitive hydrophobic dye and bioluminescent reporter in the live, intact cell. In some embodiments, methods further comprise a step of adding the ligand to the live, intact cell. In some embodiments, the ligand is endogenous to the live, intact cell. In some embodiments, the signal from said environmentally-sensitive hydrophobic dye in the live, intact cell is compared to a control sample without the ligand.

In some embodiments, provided herein are methods to detect a target/ligand interaction within a cell, comprising the steps of: (a) providing a live, intact cell expressing a fusion of a target protein and a bioluminescent reporter; (b) allowing time for the target protein to interact with the ligand within the live, intact cell; (c) lysing the cell to produce a cell lysate; (d) contacting the cell lysate with an environmentally-sensitive hydrophobic dye, wherein the emission spectra of the bioluminescent reporter and the excitation spectra of the environmentally-sensitive hydrophobic dye overlap; (e) treating the cell lysate under conditions that cause the target protein to unfold to an appropriate extent; (f) exposing the cell lysate to the substrate of the bioluminescent reporter; (g) measuring signal from the environmentally-sensitive hydrophobic dye and bioluminescent reporter in the cell lysate; and (h) detecting target/ligand interaction based on the ratio from the signals from said environmentally-sensitive hydrophobic dye and bioluminescent reporter in the cell lysate. In some embodiments, methods further comprise a step of adding the ligand to the live, intact cell. In some embodiments, the ligand is endogenous to the live, intact cell. In some embodiments, the signal from said environmentally-sensitive hydrophobic dye in the cell lysate is compared to a control sample without the ligand.

In some embodiments, provided herein are methods to detect a target/ligand interaction within a cell, comprising the steps of: (a) providing a live, intact cell expressing a fusion of a target protein and a bioluminescent reporter; (b) allowing time for the target protein to interact with the ligand within the live, intact cell; (c) contacting the live, intact cell with an environmentally-sensitive hydrophobic dye, wherein the emission spectra of the bioluminescent reporter and the excitation spectra of the environmentally-sensitive hydrophobic dye overlap; (d) lysing the cell to produce a cell lysate; (e) treating the cell lysate under conditions that cause the target protein to unfold to an appropriate extent; (f) exposing the cell lysate to the substrate of the bioluminescent reporter; (g) measuring signal from the environmentally-sensitive hydrophobic dye and bioluminescent reporter in the cell lysate; and (h) detecting target/ligand interaction based on the ratio from the signals from said environmentally-sensitive hydrophobic dye and bioluminescent reporter in the cell lysate. In some embodiments, methods further comprise a step of adding the ligand to the live, intact cell. In some embodiments, the ligand is endogenous to the live, intact cell. In some embodiments, the signal from said environmentally-sensitive hydrophobic dye in the cell lysate is compared to a control sample without the ligand.

In some embodiments, provided herein are methods to detect a target/ligand interaction within a live, intact cell, comprising the steps of: (a) providing a live, intact cell expressing a fusion of a target protein and a bioluminescent reporter; (b) allowing time for the target protein to interact with the ligand within the live, intact cell; (c) contacting the live, intact cell with an environmentally-sensitive hydrophobic dye, wherein the emission spectra of the bioluminescent reporter and the excitation spectra of the environmentally-sensitive hydrophobic dye overlap; (d) exposing the live, intact cell to the substrate of the bioluminescent reporter; (e) measuring signal from the environmentally-sensitive hydrophobic dye and bioluminescent reporter in the live, intact cell under pre-denaturing conditions; (f) treating the live, intact cell under conditions that cause the target protein to unfold to an appropriate extent; (g) measuring signal from the environmentally-sensitive hydrophobic dye and bioluminescent reporter in the live, intact cell under post-denaturing conditions; and (h) detecting target/ligand interaction based on the difference or ratio in signals from said environmentally-sensitive hydrophobic dye and bioluminescent reporter under the pre-denaturing and post-denaturing conditions in the live, intact cell. In some embodiments, methods further comprise a step of adding the ligand to the live, intact cell prior to step (e). In some embodiments, the ligand is endogenous to the live, intact cell. In some embodiments, the difference or ratio of the signal is compared to a difference or ratio of signal in a control sample without the ligand.

In some embodiments, provided herein are methods to detect target/ligand interactions within live, intact cells using luminescence-based readout. For example, in some embodiments, provided herein are methods comprising the steps of: (a) providing a live, intact cell expressing a fusion of a target protein and a bioluminescent reporter; (b) allowing time for the target protein to interact with the ligand within the live, intact cell; (c) treating the live, intact cell under conditions that cause the target protein to unfold to an appropriate extent; (d) exposing the live, intact cell to the substrate of the bioluminescent reporter; (e) measuring signal from the bioluminescent reporter in the live, intact cell; and (f) detecting target/ligand interaction based on the signal from said bioluminescent reporter in the live, intact cell.

In some embodiments, provided herein are methods to detect target/ligand interactions in live cells using lytic endpoint luminescence-based readout. For example, in some embodiments, methods comprise the steps of: (a) providing a live, intact cell expressing a fusion of a target protein and a bioluminescent reporter; (b) allowing time for the target protein to interact with the ligand within the live, intact cell; (c) treating the live, intact cell under conditions that cause the target protein to unfold to an appropriate extent; (d) lysing the cell to produce a cell lysate; (e) exposing the cell lysate to the substrate of the bioluminescent reporter; (f) measuring signal from the bioluminescent reporter in the lysate; and (g) detecting target/ligand interaction based on the signal from said bioluminescent reporter in the lysate.

In some embodiments, provided herein are methods to detect target/ligand interactions within a cell lysate using luminescence-based readout. For example, in some embodiments, methods comprise the steps of: (a) providing a live, intact cell expressing a fusion of a target protein and a bioluminescent reporter; (b) lysing the cell to produce a cell lysate; (c) allowing time for the target protein to interact with the ligand within the cell lysate; (d) treating the cell lysate under conditions that cause the target protein to unfold to an appropriate extent; (e) exposing the cell lysate to the substrate of the bioluminescent reporter; (f) measuring signal from the bioluminescent reporter in the lysate; and (g) detecting target/ligand interaction based on the signal from said bioluminescent reporter in the lysate.

In some embodiments, provided herein are methods to detect target/ligand interactions in live, intact cells using luminescence-based readout with ratiometric analysis. For example, in some embodiments, methods comprise the steps of: (a) providing a live, intact cell expressing a fusion of a target protein and a bioluminescent reporter; (b) allowing time for the target protein to interact with the ligand within the live, intact cell; (c) exposing the live, intact cell to the substrate of the bioluminescent reporter; (d) measuring signal from the bioluminescent reporter in the live, intact cell under pre-denaturing conditions; (e) treating the live, intact cell under conditions that cause the target protein to unfold to an appropriate extent; (f) measuring signal from the bioluminescent reporter in the live, intact cell under post-denaturing conditions; and (g) detecting target/ligand interaction based on the difference or ratio in signal from the bioluminescent reporter under the pre-denaturing and post-denaturing conditions in the live, intact cell.

In some embodiments, provided herein are methods to detect target/ligand interactions in a cell lysate using luminescence-based readout with ratiometric analysis. For example, in some embodiments, methods comprise the steps of: (a) providing a live, intact cell expressing a fusion of a target protein and a bioluminescent reporter; (b) lysing the cell to produce a cell lysate; (c) allowing time for the target protein to interact with the ligand within the cell lysate; (d) exposing the cell lysate to the substrate of the bioluminescent reporter; (e) measuring signal from the bioluminescent reporter in the cell lysate under pre-denaturing conditions; (f) treating the cell lysate under conditions that cause the target protein to unfold to an appropriate extent; (g) measuring signal from the bioluminescent reporter in the cell lysate under post-denaturing conditions; and (h) detecting target/ligand interaction based on the difference or ratio in signal from the bioluminescent reporter under the pre-denaturing and post-denaturing conditions in the cell lysate.

In some embodiments, provided herein are methods to detect target/ligand interactions in live, intact cells using BRET readout with dye addition following a partial denaturation step (e.g., post-heat). For example, in some embodiments, methods comprise the steps of: (a) providing a live, intact cell expressing a fusion of a target protein and a bioluminescent reporter; (b) allowing time for the target protein to interact with the ligand within the live, intact cell; (c) treating the live, intact cell under conditions that cause the target protein to unfold to an appropriate extent; (d) contacting the live, intact cell with an environmentally-sensitive hydrophobic dye, wherein the emission spectra of the bioluminescent reporter and the excitation spectra of the environmentally-sensitive hydrophobic dye overlap; (e) exposing the live, intact cell to the substrate of the bioluminescent reporter; (f) measuring signal from the environmentally-sensitive hydrophobic dye and bioluminescent reporter in the live, intact cell; and (g) detecting target/ligand interaction based on the ratiometric signal from said environmentally-sensitive hydrophobic dye and bioluminescent reporter in the live, intact cell.

In some embodiments, provided herein are methods to detect target/ligand interactions in live cells using lytic endpoint BRET readout with dye addition. For example, in some embodiments, methods comprise the steps of: (a) providing a live, intact cell expressing a fusion of a target protein and a bioluminescent reporter; (b) allowing time for the target protein to interact with the ligand within the live, intact cell; (c) treating the live, intact cell under conditions that cause the target protein to unfold to an appropriate extent; (d) lysing the cell to produce a cell lysate; (e) contacting the cell lysate with an environmentally-sensitive hydrophobic dye, wherein the emission spectra of the bioluminescent reporter and the excitation spectra of the environmentally-sensitive hydrophobic dye overlap; (f) exposing the cell lysate to the substrate of the bioluminescent reporter; (g) measuring signal from the environmentally-sensitive hydrophobic dye and bioluminescent reporter in the cell lysate; and (h) detecting target/ligand interaction based on the ratiometric signal from said environmentally-sensitive hydrophobic dye and bioluminescent reporter in the cell lysate.

In some embodiments, provided herein are methods to detect target/ligand interactions in cell lysate using BRET readout with dye addition. For example, in some embodiments, methods comprise the steps of: (a) providing a live, intact cell expressing a fusion of a target protein and a bioluminescent reporter; (b) lysing the cell to produce a cell lysate; (c) contacting the cell lysate with an environmentally-sensitive hydrophobic dye, wherein the emission spectra of the bioluminescent reporter and the excitation spectra of the environmentally-sensitive hydrophobic dye overlap; (d) allowing time for the target protein to interact with the ligand within the cell lysate; (e) treating the cell lysate under conditions that cause the target protein to unfold to an appropriate extent; (f) exposing the cell lysate to the substrate of the bioluminescent reporter; (g) measuring signal from the environmentally-sensitive hydrophobic dye and bioluminescent reporter in the cell lysate; and (h) detecting target/ligand interaction based on the ratiometric signal from said environmentally-sensitive hydrophobic dye and bioluminescent reporter in the cell lysate.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 3A-D show a detection of an increase in melting temperature for CDK2-Nluc and Nluc-CDK2 as determined by NANOLUC activity (RLU) after binding to a stabilizing ligand in live, intact cells (FIGS. 3A-B) and digitonin-treated mammalian cells (FIGS. 3C-D) and subsequently exposed to a temperature gradient.

FIGS. 5A-F show detection of an increase in melting temperature for a panel of kinases as determined by NANOLUC activity (RLU) after binding to stabilizing ligands in digitonin treated mammalian cells and subsequently exposed to a temperature gradient.

FIGS. 14A-B show analysis of isothermal dose response curves for a panel of kinase inhibitors with CDK2-Nluc and LCK-Nluc as determined by BRET after incubation in the presence of different concentrations of the individual compounds while time of heating and temperature were kept constant. This highlights the concentration dependence of the thermal stabilization and allows for compound affinity signatures to be obtained.

FIGS. 15A-15B show detection of an increase in melting temperatures (stabilizing ligand) or no change in melting temperatures (non-binding) for cytoplasmic target fusions CDK2-Nluc and Nluc-MAPK14 as determined by BRET after incubation with a panel of compounds thus displaying compound selectivity in mammalian cells subsequently exposed to digitonin and a temperature gradient.

FIGS. 17A-17C show detection of an increase in melting temperature for CDK2-Nluc as determined by BRET after incubation with stabilizing ligand (staurosporine) in mammalian cells subsequently exposed to digitonin and a temperature gradient using three different environmentally-sensitive acceptor dyes reporting on protein folding status as BRET acceptor dyes. Dye examples included: Protein Thermal Shift™ Dye (Life Technologies), SYPRO Orange protein gel stain, and SYPRO Red protein gel stain. $B_{max}$ is acceptor dye dose dependent, but that there is no change in the apparent melting temperature ($T_{agg}$).

FIGS. 20A-B show detection of an increase in melting temperature for the nuclear target fusion HDAC1-Nluc as determined by NANOLUC activity (RLU) and BRET (mBU) after incubation with stabilizing ligand in mammalian cells subsequently exposed to a temperature gradient and either analyzed immediately or incubated at room temperature for 3 minutes prior to analysis.

FIG. 21 displays prophetic examples of alternative energy transfer strategies combined with environmentally sensitive dyes to use in a thermal shift assay.

FIG. 22 is Table 1, providing the order of addition of the components for the experiments depicted in FIGS. 1-20.

FIGS. 23-34 show graphs depiction characterization of dyes synthesized in Example 18: left) BRET be used to detect ligand binding through a change in relative BRET compared to DMSO controls (Unt) as exampled with CDK2-Nluc target fusions [+/−Staurosporine (SSP)] in live or lytic conditions [+/−digitonin (Dig)]. As expected, the shape of the BRET curves are bell-shaped due to the loss of Nluc signal with protein unfolding and increasing temperatures or dye dissociation upon protein aggregation or both; middle) the fold change in BRET signal at 56° C. over the background BRET signal at 42° C. for cells transfected with CDK2-Nluc target that were treated with DMSO and varying dye concentrations. The larger the signal/background (S/B), the more signal window to allow for determining compound binding stability effects. This also allows optimal dye concentrations to be determined; right) the fold change in BRET signal at 52° C. over the background BRET signal at 42° C. for cells transfected with Nluc-MAPK14 target that were treated with DMSO and varying dye concentrations. The larger the signal/background (S/B), the more signal window to allow for determine compound binding stability effects, allowing determination of optimal dye concentrations.

FIG. 36 shows fluorescent mode analysis of CS0096.

DEFINITIONS

Figure 1A:
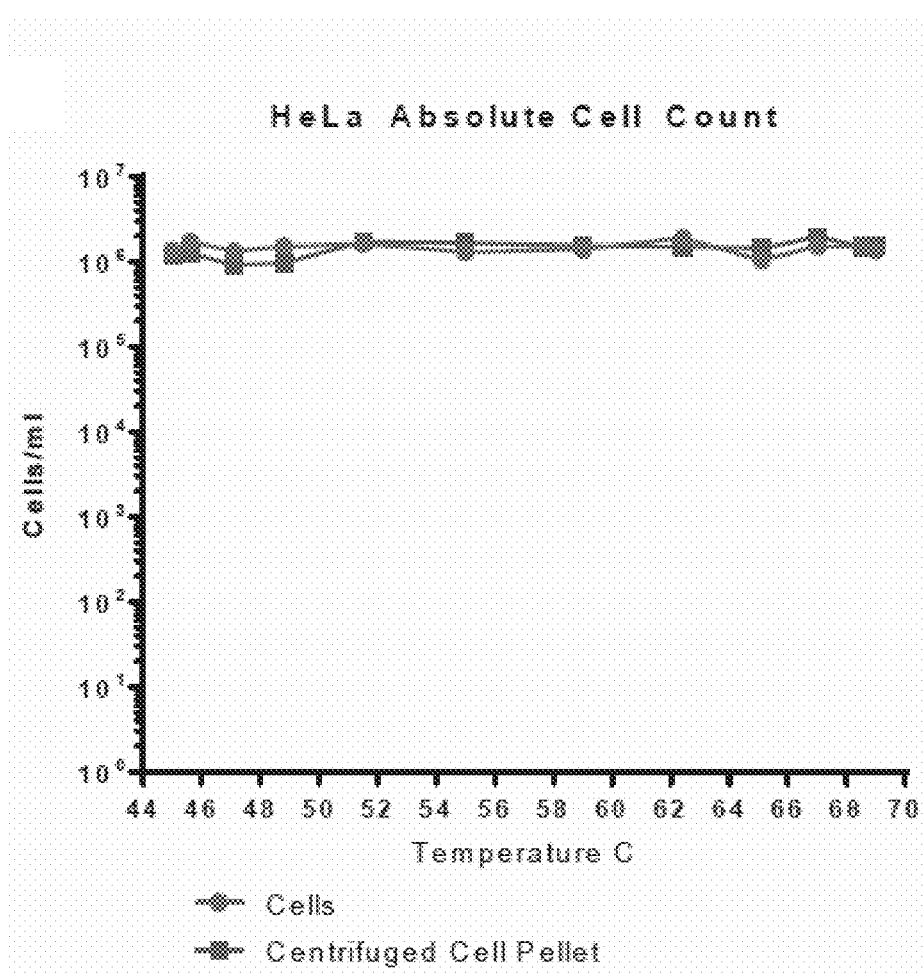
FIGS. 1A-C show the effects of heat treatment on HeLa cell viability (FIGS. 1A and 1B) and NANOLUC activity (RLU) within HeLa cells after exposure to a temperature gradient (FIG. 1C).

As used herein, the terms "fusion," "fusion protein," and "fusion polypeptide" synonymously refer to a chimera of heterologous first and second protein or polypeptide segments, for example, a chimera of a protein of interest (e.g., target protein) joined to a reporter protein (e.g., luciferase). The second protein is typically fused to the N-terminus or C-terminus of the first protein, but may also be inserted internally within the sequence of the first protein.

As used herein, the term "luciferase" refers to any of a variety of monooxygenase enzymes that catalyze the conversion (e.g., oxidation) of a substrate (e.g., firefly luciferin, latia luciferin, bacterial luciferin, coelenterazine, dinoflagellate luciferin, vargulin, and derivatives thereof) into an excited-energy-state product that emits energy in the form of light upon decaying to its ground state.

As used herein, the term "natural polypeptide" as used herein refers to a polypeptide that exists in nature. For example, a "natural luciferase" is a luciferase polypeptide with a sequence and/or any other relevant features (e.g., post-translational modifications) that exists in nature. The term "synthetic polypeptide" refers to a polypeptide having an amino acid sequence that is distinct from those found in nature (e.g., not natural). When used in this context, the term "synthetic" does not relate to the method by which a polypeptide is produced (e.g., recombinant technology, chemical synthesis, etc.). A "wild-type polypeptide" or "wild-type luciferase" is the most common variant occurring in nature; whereas a "variant polypeptide" or "mutant polypeptide" refers to a polypeptide having an amino acid sequence that is distinct from the wild-type sequence. A variant or mutant polypeptide may be natural or synthetic. The aforementioned terms (e.g., "natural", "synthetic", "wild-type", "variant", and "mutant") have the same meanings when used in reference to nucleic acids, genes, peptide, proteins, etc.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "sample" is used broadly to refer to any of biological samples (e.g., fluids, tissues, etc.) and environmental samples as well as reaction mixtures or other multicomponent solutions and mixtures.

As used herein, the term "complex sample" refers to a sample comprising a large number and variety of different compounds, polymers, macromolecules, complexes, etc. A complex sample may comprise buffers, salts, peptides, polypeptides, proteins (including also enzymes), carbohydrates (complex and simple carbohydrates), lipids, fatty acids, fat, nucleic acids, organelles and other cellular components, etc. Examples of complex samples include cells, e.g., live intact cells, cell lysates, body fluids (e.g., blood (or blood products), saliva, urine, etc.), tissues (e.g., biopsy tissue), cells grown in vitro and subsequently injected into animal in vivo and recollected for ex vivo analysis, cells in 3D culture, cells in tissues, reaction mixtures, etc. In particular embodiments, a complex samples contain a target protein as well as additional non-target peptides, polypeptides, and/or proteins.

As used herein, the term "quenched" refers to a decrease in fluorescence emission from a fluorescent entity (e.g., dye) upon interaction of a particular substance (e.g., water) or condition, relative to the fluorescence emission from the fluorescent entity when not interacting with the particular substance or condition. The term "quenched" itself does not place any limitation on the extent of the decrease in fluorescence. The degree of quenching may be expressed at a percentage of fluorescence in the quench state compared to the unquenched state (e.g., 10 RLU in the quenched state compared to 100 RLU in the unquenched state is 90% quenching).

As used herein, the term "BRET" is used to describe the occurrence of bioluminescence resonance energy transfer between a bioluminescent donor (e.g., a luciferase protein) and an acceptor fluorophore. It is a distance-dependent interaction in which energy is transferred from the donor bioluminescent protein and substrate to an acceptor fluorophore without emission of a photon. The efficiency of BRET is dependent on the inverse sixth power of the intermolecular separation, making it useful over distances comparable with the dimensions of biological macromolecules (e.g., within 30-80 Å, depending on the degree of spectral overlap).

As used herein, the term "ligand for a target protein" refers to a molecular entity that binds to a target protein. The ligand may be a small molecule, peptide, antibodies, macromolecules (e.g., nucleic acid, viral proteins, bacterial proteins, polysaccharides, synthetic polymers), or other molecular entity that bind the target protein. The term "test ligand" refers to a molecular entity that is being assayed for the capacity to bind the target protein.

DETAILED DESCRIPTION

Provided herein are systems and methods for characterizing target/ligand engagement. In particular, luciferase-labeled polypeptide targets are used to detect or quantify target/ligand engagement (e.g., within a cell or cell lysate).

In some embodiments, compositions (e.g., fusions of target polypeptides and luciferase reporter), systems (e.g., kits or reaction mixtures comprising, for example, test ligands, luciferase substrates, assay reagents, cells, e.g., live intact cells, cell lysates, etc.) and methods are provided for monitoring (e.g., detecting, quantitating, etc.) target/ligand engagement in complex (cellular) environments (e.g., based on the biophysical principle of ligand-induced thermal stabilization of target proteins). In some embodiments, the luminescent signal generated by a fusion of a target protein and luciferase (e.g., NANOLUC (Promega Corp., Madison, WI); see, e.g., U.S. Pat. Nos. 8,557,970 and 8,669,103, both of which are herein incorporated by reference in their entireties) or a luciferase peptide/polypeptide interacts with a complement polypeptide/peptide to produce an active enzyme (e.g., NLPep and NLPoly (Promega Corp., Madison, WI); see, e.g., U.S. Pub. No. 2014/0348747, which is herein incorporated by reference in its entirety) is monitored over temperature range sufficient to result in unfolding and aggregation of the unbound target protein, both in the presence and absence of a ligand or test ligand for the target protein. An altered or shifted luminescent signal over the range of temperatures indicates interaction between the target protein and ligand. In some embodiments, the luminescent signal (e.g., relative light units (RLU)) from the luciferase reporter portion of the fusion is directly monitored. In some embodiments, bioluminescence resonance energy transfer (BRET) from the luciferase reporter portion of the fusion to an environmentally sensitive dye (e.g., a dye that interacts with the hydrophobic portions of the target protein as they become exposed at higher temperatures, a protein-aggregation detection dye, etc.) is measured.

In some embodiments, the target/luciferase fusion is expressed in cells (e.g., a live intact cell or a relevant cell line), and the cells and/or a cell lysate thereof, is exposed to a ligand of interest (e.g., ligand for the target protein, test ligand (e.g., potential drug), etc.) and subsequently exposed to conditions (e.g., increased temperature) capable of causing the unfolding and/or aggregation of the unbound target protein. In such embodiments, a target protein that has been stabilized by interaction with ligand in the cell or cell lysate will exhibit an altered or shifted melting temperature as detected by alteration of the luminescent or BRET signal in the presence and absence of ligand.

In some embodiments in which luciferase signal is directly detected as a measure of thermal shift, luciferase substrate (and purified complementary peptide/polypeptide in the case complementation assays (e.g., using NLPep and NLPoly (Promega Corp., Madison, WI); see, e.g., U.S. Pub. No. 2014/0348747, which is herein incorporated by reference in its entirety)) is added to the samples (e.g., cells, cell lysate, etc.) for analysis. In other embodiments in which BRET signal from the luciferase of the fusion to an environmentally sensitive dye (e.g., a dye that interacts with the hydrophobic portions of the target protein as they become exposed at higher temperatures, a protein-aggregation detection dye, etc.) is detected as a measure of thermal shift, luciferase substrate (and purified complementary peptide/polypeptide in the case complementation assays (e.g., using NLPep and NLPoly)) and the environmentally sensitive dye are added to the samples (e.g., cells, cell lysate, etc.) for analysis. In some embodiments, detergents (e.g. Digitonin), lysis buffer (e.g. NANOGLO Lytic reagent), and/or other reagents are added to the sample. In some embodiments, luminescence and/or BRET is analyzed using, for example, by a luminometer at one or more specific temperatures (e.g., encompassing a temperature in which the target protein unfolds). Shift of the signal (e.g., luciferase signal or BRET signal) in the presence vs. absence of ligand indicates interaction (e.g., binding) of the target and ligand.

It has long been recognized that the binding of low molecular weight ligands increases the thermal stability of a protein (Koshland (1958). Proc Natl Acad Sci USA. 44 (2): 98-104; Linderstrøm-Lang & Schellman (1959). The Enzymes. 1(2) 443-510; herein incorporated by reference in its entirety). A TSA detects this stabilizing effect by measuring the thermal stability of a target protein in the presence and absence of a ligand, thereby detecting or quantifying the target/ligand interaction. A traditional TSA is a fluorescence-based method for monitoring target/ligand interactions (WO 1997/020952; herein incorporated by reference in its entirety); the primary weakness of such an assay is that it detects the unfolding of any proteins present in the sample being assayed (e.g., target and non-target protein), and therefore can only be used to analyze purified protein. Because target/ligand interactions may be affected by a multitude of factors in vivo, a traditional TSA of purified protein may be of limited informational value. Other TSA-type assays have been developed (See, e.g., Moreau M J, et al. Quantitative determination of protein stability and ligand binding using a green fluorescent reporter system. Mol. Biosyst. (6); 1285-1292. 2010; and CETSA, U.S. Pub No. 2014/0057368; herein incorporated by reference in their entireties); however, these assays rely on post-denaturation quantification of soluble vs. denatured protein as a measure of target protein stability and require multiple purification and/or detection steps. Provided herein are assays that can be used to identify ligands that bind to a target protein and/or to quantify the affinity of such interactions. The assays described herein are distinct from other methods (e.g., traditional thermal shift, GFP reporter systems, CESTA, etc.), for example, because: (1) the assays allow characterization of target/ligand interactions with non-purified protein; (2) the assays can be conducted in a cell, cell lysate, or other complex liquid containing many different biomolecules; (3) the assay technology does not rely upon antibodies recognizing target protein epitopes; (4) the assays are homogeneous; (5) the assays use common and simple reagents, materials and instruments (e.g., a luminometer); and/or (6) assays are not limited to a single read.

In some embodiments, the systems and methods described herein utilize fusion constructs (e.g., fusion polypeptides and nucleic acids and vectors encoding them) comprising a target protein (e.g., the binding characteristics of which are being examined) and a reporter peptide or polypeptide. In some embodiments, any protein of interest may find use as the target protein. Assays described herein provide for analysis of the binding characteristics (e.g., potential ligands, binding affinity, etc.) of such proteins. A reporter of the fusion construct may be any peptide or polypeptide, the activity of which can be detected within a cell, e.g., a live intact cell, or cell lysate, in real-time. While the scope of embodiments herein is not limited by the identity of the reporter, many embodiments utilize a luciferase reporter. In such embodiments, a suitable luciferase is fused (e.g., directly or by a linker (e.g., peptide or other linker moiety)) to the N-terminus or C-terminus of a target protein (or inserted internally within the target protein) to generate a fusion polypeptide for use in the systems and methods herein. In some embodiments, nucleic acid constructs are provided that encode fusion polypeptides (e.g., N-target-reporter-C, N-reporter-target-C, N-target-linker-reporter-C, N-reporter-linker-target-C, etc.). In some embodiments, vectors (e.g., plasmids, bacmids, cosmids, viral vectors (e.g., lentivirus vectors, adeno-associated viral vectors (AAVs), etc.), etc.) comprising nucleic acid constructs that encode fusion polypeptides (e.g., along with appropriate incorporation and/or expression elements) are provided. In some embodiments, cells (e.g., bacterial, mammalian, human, etc.) transformed or transfected (e.g., transiently or stably) with nucleic acids and/or vectors encoding fusion polypeptides useful for assays described herein are provided.

Although the reporter of a fusion construct may be one that exhibits any suitably detectable activity, in some embodiments, the reporter is a luciferase enzyme. Suitable luciferase enzymes include those selected from the group consisting of: *Photinus pyralis* or North American firefly luciferase; *Luciola cruciata* or Japanese firefly or Genjibotaru luciferase; *Luciola italic* or Italian firefly luciferase; *Luciola lateralis* or Japanese firefly or Heike luciferase; *Luciola mingrelica* or East European firefly luciferase; *Photuris pennsylvanica* or Pennsylvania firefly luciferase; *Pyrophorus plagiophthalamus* or Click beetle luciferase; *Phrixothrix hirtus* or Railroad worm luciferase; *Renilla reniformis* or wild-type *Renilla* luciferase; *Renilla reniformis* Rluc8 mutant *Renilla* luciferase; *Renilla reniformis* Green *Renilla* luciferase; *Gaussia princeps* wild-type Gaussia luciferase; *Gaussia princeps* Gaussia-Dura luciferase; *Cypridina noctiluca* or Cypridina luciferase; *Cypridina hilgendorfii* or Cypridina or Vargula luciferase; *Metridia longa* or Metridia luciferase; and Oplophorus luciferase (e.g., *Oplophorus gracilirostris* (OgLuc luciferase), *Oplophorus grimaldii, Oplophorus spinicauda, Oplophorus foliaceus, Oplophorus noraezeelandiae, Oplophorus typus, Oplophorus noraezelandiae* or *Oplophorus spinous*). For any of the above luciferases, fusions may contain a wild-type or naturally-occurring variant of the luciferase or may comprise a synthetic version (e.g., optimized for one or more characteristics (e.g., emission, stability, etc.). In some embodiments, assays are carried out both in the presence and absence of a ligand for the target protein (or a test ligand) and in the presence of the appropriate substrate for the luciferase. A negative control assay may be performed in the absence of substrate. A positive control may be performed with the un-fused luciferase and appropriate substrate in the presence and absence of ligand and/or in the presence an absence of un-fused target protein.

In some embodiments, a substrate for the reporter (e.g., bioluminescent reporter (e.g., luciferase, etc.), etc.) is provided. In some embodiments, a bioluminescent reporter converts the substrate into a reaction product and releases light energy, e.g., luminescence, as a byproduct. In some embodiments, the substrate is a substrate for a luciferase enzyme. Appropriate substrates for known reporters are understood in the field.

In some embodiments, a fusion construct comprises a target protein fused to a *Oplophorus grachlorostris* luciferase (OgLuc). The fusion may comprise a natural (e.g., wild-type or variant) OgLuc sequence or may comprise a synthetic OgLuc (e.g., optimized for one or more characteristics (e.g., luminescence, signal stability, protein stability, etc.), etc.). The natural wild-type OgLuc sequence is given in SEQ ID NO: 1. Some suitable Oplophorus luciferases are described, for example, in U.S. Pat. Nos. 8,669,103 and 8,557,970. In some embodiments, a luciferase polypeptide comprises at least 60% (e.g., >65%, >70%, >75%. >80%, >85%, >90%, >95%, >98%, >99%, 100%, and any ranges therein) sequence identify with SEQ ID NO: 1. In some embodiments, comprises a amino acid substitutions at positions relative to one or more of positions: 1, 2, 4, 6, 10, 11, 14, 15, 16, 18, 19, 20, 21, 22, 23, 24, 25, 27, 28, 31, 32, 33, 34, 36, 38, 39, 40, 42, 43, 44, 45, 46, 47, 48, 49, 50, 51, 54, 55, 56, 58, 59, 60, 66, 67, 68, 69, 70, 71, 72, 74, 75, 76, 77, 86, 87, 89, 90, 92, 93, 94, 95, 96, 97, 98, 99, 100, 102, 104, 106, 109, 110, 111, 112, 113, 115, 117, 119, 124, 125, 126, 127, 128, 129, 130, 135, 136, 138, 139, 142, 143, 144, 145, 146, 147, 148, 149, 150, 152, 154, 155, 159, 158, 163, 166, 167, 168, or 169 of SEQ ID NO: 1. In some embodiments, a luciferase exhibits one or more of enhanced luminescence, enhanced signal stability, and enhanced protein stability relative to a wild-type *Oplophorus* luciferase. In some embodiments, comprises at least 60% (e.g., >65%, >70%, >75%. >80%, >85%, >90%, >95%, >98%, >99%, 100%, and any ranges therein) sequence identify with SEQ ID NO: 2. In some embodiments, comprises SEQ ID NO: 2.

In some embodiments, a target protein is fused to a first peptide or polypeptide (e.g., that does not independently exhibit substantial detectable activity) that forms an active reporter construct through structural complementation with a second polypeptide or peptide (See, e.g. U.S. Ser. No. 14/209,610 and U.S. Ser. No. 14/209,546; herein incorporated by reference in their entireties.). In such embodiments, only one of the two (or more) elements (peptide or polypeptide) that form the reporter construct is fused to the target. The structural complement of the fused element of the reporter construct is added separately to the system (e.g., cell (e.g., added exogenously, expressed by the cell), cell lysate, in vitro system, etc. In particular embodiments, a target protein is fused to a first peptide or polypeptide (e.g., that doesn't independently exhibit a detectable activity) that forms an active luciferase construct through structural complementation with a second polypeptide or peptide (See, e.g. U.S. Ser. No. 14/209,610 and U.S. Ser. No. 14/209,546; herein incorporated by reference in their entireties.). In such embodiments, the fusion polypeptide will not independently catalyze a significant amount of substrate a high-energy-state product that will produce light upon return to a stable state. Rather, only in the presence of the complement polypeptide or peptide is the active luciferase construct formed. Embodiments will typically be described as comprising a target fused to a complete reporter; however, unless indicated otherwise, it should be understood that the reporter may be formed by structural complementation of multiple (e.g., 2, 3, or more) elements, only one of which is fused to the target.

In some embodiments, a first peptide (e.g., fused to the target protein) comprises at least 60% (e.g., 65%, 70%, 75%. 80%, 85%, 90%, and any ranges therein) but less than 100% sequence identify with SEQ ID NO: 3, and a complement polypeptide comprises at least 60% (e.g., 65%, 70%, 75%. 80%, 85%, 90%, 95%, and any ranges therein) but less than 100% sequence identify with SEQ ID NO: 4. In some embodiments, the first peptide comprises an amino acid substitutions at positions relative to one or more of positions: G157del, T159S, C164F, E165K, N166K, L168S, A169del of SEQ ID NO: 3 (wherein SEQ ID NO: 3 numbering is 157-169). In some embodiments, the complement polypeptide comprises a amino acid substitutions at positions relative to one or more of positions: Q11E, G15A, F31L, G35A, L46R, G51A, G67A, G71A, M75E, I76V, H93P, I107L, D108N, N144T, L149M, 157S (addition of S at 157 position) of SEQ ID NO: 4 (wherein SEQ ID NO: 4 numbering is 1-156).

In some embodiments, a first polypeptide (e.g., fused to the target protein) comprises at least 60% (e.g., 65%, 70%, 75%. 80%, 85%, 90%, 95%, and any ranges therein) but less than 100% sequence identify with SEQ ID NO: 4, and a complement polypeptide comprises at least 60% (e.g., 65%, 70%, 75%. 80%, 85%, 90%, and any ranges therein) but less than 100% sequence identify with SEQ ID NO: 3. In some embodiments, the first polypeptide comprises a amino acid substitutions at positions relative to one or more of positions (e.g., Q11E, G15A, F31L, G35A, L46R, G51A, G67A, G71A, M75E, I76V, H93P, I107L, D108N, N144T, L149M, 157S (addition of S at 157 position) of SEQ ID NO: 4 (wherein SEQ ID NO: 4 numbering is 1-156)). In some embodiments, the complement peptide comprises a amino acid substitutions at positions relative to one or more of positions (e.g., G157del, T159S, C164F, E165K, N166K, L168S, A169del of SEQ ID NO: 3 (wherein SEQ ID NO: 3 numbering is 157-169)).

Depending upon the identity of the bioluminescent reporter used, an appropriate substrate will be selected, for example, from those including, but not limited to: firefly luciferin, latia luciferin, bacterial luciferin, coelenterazine, dinoflagellate luciferin, vargulin, and suitable derivatives thereof. In some embodiments, the substrate is a substrate for an *Oplophorus* luciferase, e.g., NANOLUC enzyme from Promega Corporation (e.g., SEQ ID NO: 2). In some embodiments, the substrate comprises coelenterazine, a coelenterazine derivative, a structural or functional equivalent of coelenterazine, a molecule substantially equivalent to coelenterazine (e.g., structurally and/or functionally), or molecule functionally or structurally similar to coelenterazine. In some embodiments, the bioluminescent reporter converts the coelenterazine, coelenterazine derivative, structural or functional equivalent of coelenterazine, or substantial equivalent to coelenterazine into coelenteramide, a coelenteramide derivative, a structural or functional equivalent of coelenteramide, or a substantial equivalent to coelenteramide and releases light energy as a byproduct.

In some embodiments, a reporter is an epitope tag (See FIG. 21, top panel). In such embodiments, a labeled (e.g., fluorescently labeled) antibody that recognizes and binds the epitope is included. In some embodiments, BRET occurs between the label on the antibody and the fluorescent dye when both are bound to the epitope-tagged target protein. In some embodiments, the epitope is accessible to the antibody when the protein is folded or unfolded. In other embodiments, some degree of target unfolding is required for the antibody to access the epitope tag. In some embodiments, following a thermal denaturation step, addition of a detection antibody labeled with a donor fluorophore (e.g. terbium, europium, etc.) is used in a FRET assay with denaturation/aggregation-sensitive (e.g., environmentally-sensitive dye, hydrophobic dye, etc.) dye as a FRET acceptor. Ligand-mediated thermal stabilization results in a loss of FRET/TR-FRET signal and/or the requirement of more denaturing conditions (e.g., higher temperature) to achieve the FRET/TR-FRET signal.

In some embodiments, two epitope tags (e.g. FLAG-V5) are fused to a target protein (See FIG. 21, bottom panel). In such embodiments, the epitopes are accessible to separate, differently-labeled antibodies (e.g., donor and acceptor labeled) for the respective epitopes when the target protein is folded (FRET signal is produced). Upon partial or complete unfolding of the target, the epitopes become unavailable and the FRET signal is lost.

In some embodiments, the formation of a fusion protein does not substantially impact or alter the stability or function of either the target or reporter relative to the function of each individual protein. For example, for a fusion of target enzyme and a luciferase, the formation of the fusion does not substantially alter the stability of either portion, the luminescence of the luciferase, the signal stability of the luciferase, or the activity of the enzyme.

In some embodiments, the target polypeptide and reporter polypeptide (e.g., luciferase) are connected directly without intervening amino acid sequence. For example, the target polypeptide may be fused to the N-terminus or the C-terminus of the reporter. In other embodiments, the target polypeptide and reporter polypeptide (e.g., luciferase) are connected by a linker moiety or connector sequence. In some embodiments, a linker provides connection and allows a desired amount of space/distance between the elements (e.g., to reduce interactions between target and reporter). Although a linker is typically a peptide linker, in some embodiments, other chains or polymers may be utilized. In some embodiments, a connector sequence comprises or consists of one or more amino acids (e.g., a peptide or polypeptide chain of 2-50 amino acids (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and any ranges therein). In some embodiments, the presence of a connector sequence in a fusion protein does not substantially impact or alter the stability or function of either the target or reporter relative to the function of each individual protein. For example, for a fusion of target enzyme and a luciferase, the presence of a connector sequence does not substantially alter the stability of either portion, the light output of the luciferase, or the activity of the enzyme. In some embodiments, a connector sequence is included in a fusion to prevent interactions between the target and reporter that could affect the stability of activity of either or both portions. For any particular combination of proteins in a fusion, a wide variety of connector sequences may be employed. In one embodiment, the connector sequence is a sequence recognized by an enzyme, e.g., a cleavable sequence. For instance, the connector sequence may be one recognized by a caspase or TEV protease, or may be a chemically-cleavable or photocleavable sequence.

In some embodiments, the activity (e.g., luminescence) of a reporter (e.g., luciferase) fused to a target protein is directly detected. In some embodiments, the activity (e.g., luminescence) of a reporter construct (e.g., luciferase dimer), a portion of which is fused to a target protein (e.g., the structural complement portion is not fused to the target protein), is directly detected. In some embodiments, reporter activity is measured at one or more temperatures as a measure of target protein stability. In some embodiments, at lower temperatures (e.g., <50° C., <48° C., <46° C., <44° C., <42° C., <40° C., <38° C., <36° C., 34° C., <32° C., <30° C., and ranges therein (e.g., 30-50° C., 35-45° C., etc.), depending upon the target and reporter stabilities) both the target and reporter are stably folded. As temperatures are increased, and one or both of the target and reporter begin unfolding or aggregating, signal from the reporter decreases (e.g., the activity of the reporter decreases as it becomes unfolded or aggregated). In some embodiments, because the reporter and target are fused, a more stable the target protein results in a more stable reporter and reporter signal. Similarly, a less stable target results in destabilization of the reporter and a loss, or reduction, of reporter signal at a lower temperature. In some embodiments, if a ligand binds to the target protein, the target protein is stabilized. Since, in some embodiments, stabilization of the target protein results in stabilization of the reporter and enhancement of signal stability, binding of the ligand to the target can be observed as an increase in the stability of the reporter signal. Embodiments in which the signal from the reporter (e.g., luciferase) at a given temperature (e.g., around the $T_m$ of the protein) or temperature range is directly used as a measure of protein stability are referred to herein as "direct detection."

In some embodiments, ligand binding destabilized the target protein. In some embodiments, the reporter is thermally stable or labile compared to the protein of interest it is fused to.

In some embodiments, the activity (e.g., luminescence) from a target/reporter fusion is measured at one or more temperatures (e.g., over a range of temperatures (e.g., from below the $T_m$ of the target protein to above the $T_m$ of the target protein)), both in the presence and absence of a ligand for the target or a test ligand. If the ligand or test ligand binds to or interacts with the target protein under the conditions assayed (e.g., in a cell, in a cell lysate, etc.), a corresponding shift in the activity of the reporter is observed. For example, at a given temperature (e.g., near the $T_m$ of the target protein) the activity (e.g., luminescence (e.g., RLUs)) of the reporter (e.g., luciferase) is increased. If the unfolding of the protein is analyzed at a range of temperatures, so as to determine a $T_m$, ligand binding and stabilization of the target protein is apparent as a shift (e.g., right shift) in the $T_m$ to a higher temperature.

Traditional thermal shift assays utilize purified target protein and a dye that (1) binds nonspecifically to hydrophobic surfaces and (2) is quenched by water (e.g., Sypro Orange). In such an assay, at lower temperatures (e.g., <50° C., <48° C., <46° C., <44° C., <42° C., <40° C., <38° C., <36° C., 34° C., <32° C., <30° C., and ranges therein (e.g., 30-50° C., 35-45° C., etc.), depending upon the target stability) the target is stably folded, and the hydrophobic regions of the target are buried and inaccessible to the hydrophobic dye. Under these folded conditions, the dye cannot significantly bind to the target protein, and therefore fluorescence from the dye is quenched by water in the aqueous environment. As temperatures are increased, the target begins unfolding and/or aggregating, the hydrophobic regions of the target become reveled, and the dye binds to the target. Upon binding the target protein, the dye becomes unquenched and the fluorescent signal increases. The more stable the target, the higher the temperature required to observe the fluorescence increase. Similarly, a less stable target results in destabilization of the target and an increase in fluorescent signal at a lower temperature. In such an assay, if a ligand binds to the target protein, the target protein is stabilized, which can be observed as an increase in the temperature required to generate the fluorescent signal.

The traditional TSA relies on nonspecific binding of the dye (e.g., Sypro Orange) to the hydrophobic regions of the target protein. Therefore, if proteins other than the target protein are present in the assay, the dye will bind to those proteins as well (e.g., as they become unfolded), thereby confounding the results. For at least this reason, traditional TSAs are performed using purified target protein and cannot be performed in cells, cell lysate, or other complex environments.

The direct detection embodiments described above overcome the limitation of the traditional TSA by detecting activity of a reporter fused to the target protein. The unfolding of proteins not fused to the reporter (e.g., proteins present in the cellular milieu or cell lysate) do not directly affect the signal. In another embodiment, a BRET TSA is provided that makes use of the target-specificity of the direct-detection embodiments described herein (e.g., only the unfolding of proteins fused to a reporter are monitored (e.g., even in a complex environment)), as well as the sensitivity of the traditional TSA (e.g., the increase in fluorescence from the dye is directly correlated with the degree of unfolding of the target protein). In such embodiments, a fusion of a target protein and reporter (e.g., luciferase) is generated, and fluorescence measurements are taken in the presence of an environmentally-sensitive dye (e.g., a dye that: (1) binds nonspecifically to hydrophobic surfaces, (2) has an excitation spectra that significantly overlaps the emission spectra of the reporter, and optionally (3) the fluorescence of which is quenched by water). The activity of the dye may be quenched by water (e.g., as in a traditional TSA), or the dye may be active (e.g., capable of emitting light at a particular wavelength in response to an excitation) whether bound to a protein or free in solution. In some embodiments, because the dye will be excited via BRET from the reporter and not directly, the capacity for the dye to fluoresce when not bound to the target (e.g., when bound to other proteins within a cell or cell lysate.) does not affect the assay (e.g., because only target-bound dye is within the range (e.g., 1-10 nm) to receive energy transfer from the reporter). In some embodiments, at lower temperatures (e.g., <50° C., <48° C., <46° C., <44° C., <42° C., <40° C., <38° C., <36° C., 34° C., <32° C., <30° C., and ranges therein (e.g., 30-50° C., 35-45° C., etc.), depending upon the target stability) the target is stably folded, and the hydrophobic regions of the target are buried and inaccessible to the hydrophobic dye. Under these folded conditions, signal from the reporter (e.g., fused to the target) is detected, but because the dye cannot significantly bind to the folded target protein (e.g., because hydrophobic regions are no accessible on the folded target) fluorescence from the dye as a result of BRET is not detected (e.g., significant direct reporter signal is observed, but BRET to the dye is not observed, is decreased, and/or is minimal). The proximity limitation of BRET prevents significant energy transfer from occurring between the reporter and unbound dye. In embodiments in which the dye is quenched by water, unbound dye is also not detected by direct excitation (e.g., from a light source). In embodiments in which the dye maintains its activity in water, while not producing a signal from BRET, the unbound dye may be detected by direct excitation (e.g., from a light source). As temperatures are increased, the target begins unfolding and/or aggregating, the hydrophobic regions of the target become revealed, the dye binds to the target, and the dye becomes unquenched (e.g., the quantum yield of the dye increases). Under these partially-folded or unfolded conditions, BRET occurs from the reporter to the bound dye (e.g., dye bound to the revealed hydrophobic portions of the target protein), and fluorescence from the dye, as the result of BRET, is detectable as a direct measure of (e.g., is proportional to) target protein unfolding. The more stable the target, the higher the temperature required to observe the increase in BRET. Similarly, a less stable target results in destabilization of the target and an increase in the BRET signal at a lower temperature. In such an assay, if a ligand binds to the target protein, the target protein is stabilized, which can be observed as an increase in the temperature required to generate the BRET signal (e.g., to generate increased BRET signal (e.g., increased over background)). In BRET TSA, although the hydrophobic dye will bind to any proteins present in the complex sample (e.g., cell, cell lysate, etc.), only the target protein is fused to the reporter, therefore the BRET signal will be specific to the target protein. Due to the proximity constraints placed on BRET, significant energy transfer only occurs between the reporter and target-bound dye. The BRET signal is made possible by 1) presence of reporter (e.g., NLuc) activity and 2) binding of the dye to the fusion protein allowing the reporter to donate and excite the dye to emit at a certain wavelength. The fusion of the reporter to the target provides the target specificity; the dye provides a readout of the target protein state (e.g., folded, partially folded, unfolded, etc.).

In some embodiments, BRET TSAs described herein utilize fluorogenic dyes. In other embodiments, dyes are non-fluorogenic.

In some embodiments, BRET TSAs described herein utilize fluorescent dyes that: (1) are quenched by an aqueous environment (e.g., when not bound by a target); (2) interact with (e.g., bind) hydrophobic surfaces, such a hydrophobic peptide segments; and (3) exhibit enhanced or increased fluorescence upon binding a hydrophobic surface.

Certain fluorescent compounds exhibit only a weak fluorescence emission when free in aqueous solution (Semisotnov, et al., Biopolymers 31:119, 1991; herein incorporated by reference in its entirety), but fluoresce much more strongly when bound to organized hydrophobic surfaces. Binding of these compounds to fully folded globular proteins is typically weak, since hydrophobic residues are predominantly buried in the interior of the protein. Furthermore, binding of these compounds to random coil conformations (as found in fully unfolded or denatured polypeptides) is also disfavored because in these conformations hydrophobic residues, though exposed, are not sufficiently well organized to support high affinity binding of the probes. The dyes, however, typically bind with higher affinity and stoichiometry to compact unfolded protein conformations, such as "molten globules", which are characterized by compactness relative to random coil unfolded states, the presence of substantial secondary structure, and the lack of a unique overall conformation. These probes may be referred to herein as "environmentally-sensitive hydrophobic dyes."

In some embodiments, BRET TSAs described herein utilize fluorescent dyes that bind to the hydrophobic regions of unfolding proteins, molten globules, and aggregates. Due to the proximity limitations of BRET, significant energy transfer from the bioluminescent report to the fluorescent dye only occurs when the dye is bound to the unfolding target protein. When the target protein is fully folded, the fluorescent dye does not bind the target protein, the dye is not within the proximity of the bioluminescent reporter, and BRET does not occur. In such embodiments, the bioluminescent reporter provides the system's specificity for the target protein while the fluorescent dye provides the measure of protein unfolding.

Examples of dyes that find use in embodiments described herein include SYPRO Orange, 1-anilino-8-naphthalene sulfonate (ANS), bis-1-anilino-8-naphthalene sulfonate (bis-ANS), 6-propionyl-2-(N,N-dimethyl)-aminonaphthalene (Prodan) (Molecular Probes, Eugene, OR), SYPRO Red, SYPRO Ruby, SYPRO Tangerine, and Nile Red. Other suitable dyes are those listed in Table 1.

TABLE 1

| Structure | MS | Optical Property (in DMSO) | | Reference # |
|---|---|---|---|---|
| | | Emission | Excitation | |
| [structure shown] | 487.2 | 468-490 | 620 | CS0000 |

TABLE 1-continued
| Structure | MS | Emission | Excitation | Reference # |
|---|---|---|---|---|
| 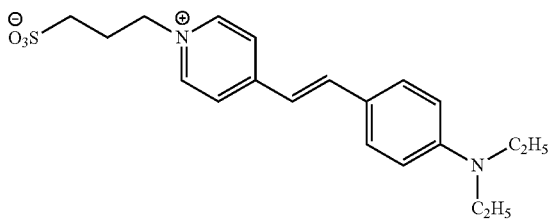 | 375.6 | 468 | 618 | CS0004 |
| 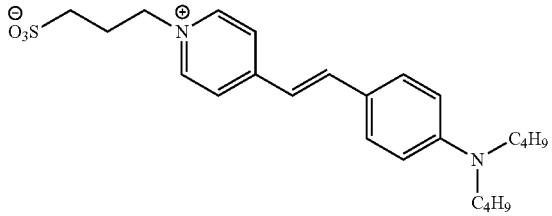 | 431.7 | 468-490 | 622 | CS0007 |
| 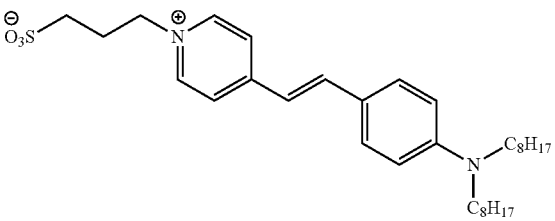 | 543.9 | 468-490 | 620 | CS0008 |
| 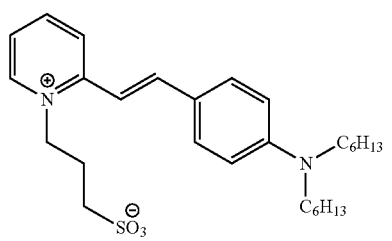 | 487.7 | 468 | 602 | CS0020 |
| 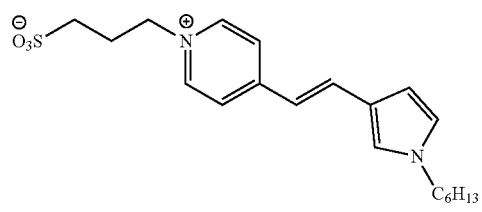 | 377.3 | 450 | 526 | CS0013 |
| 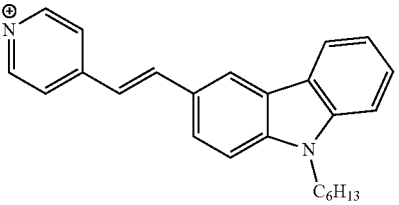 | 477.3 | 430-450 | 580 | CS0010 |

TABLE 1-continued

| Structure | MS | Optical Property (in DMSO) Emission | Excitation | Reference # |
|---|---|---|---|---|
| [structure] | 427.2 | 405 | 505 | CS0017 |
| [structure] | 399.5 | 489-514 | 644 | CS0018 |
| [structure] | 513.9 | 468 | 620 | CS0043 |
| [structure] | 537.9 | 560 | 680 | CS0028 |
| [structure] | 513.6 | 516 | 702 | CS0024 |
| [structure] | 359.7 | 470-480 | 620 | CS0075 |

TABLE 1-continued

| Structure | MS | Optical Property (in DMSO) Emission | Excitation | Reference # |
|---|---|---|---|---|
| (structure) | 479.7 (M+) | 480 | 624 | CS0101 |
| (structure) | 451.7 (M+) | 480 | 624 | CS0036 |
| (structure) | 711.1 (M+) | 480 | 622 | CS0100 |
| (structure) | 654.9 (M+) | 480 | 622 | CS0045 |
| (structure) | 776.1 | 478 | 620 | CS0048 |

TABLE 1-continued
| Structure | MS | Optical Property (in DMSO) Emission | Excitation | Reference # |
|---|---|---|---|---|
| 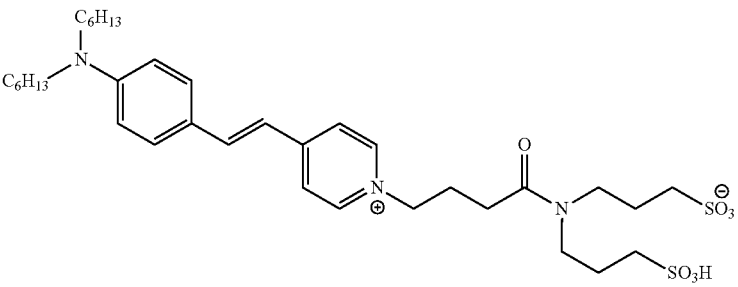 | 695.1 | 480 | 620 | CS0073 |
| 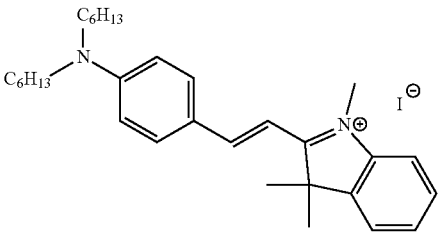 | 455.7 (M+) | 550 | 604 | CS0067 |
| 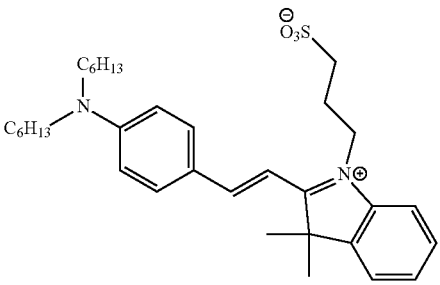 | 553.9 | 550 | 604 | CS0068 |
| 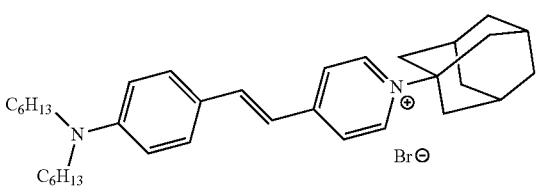 | 499.8 (M+) | 480 | 618 | CS0096 |
| 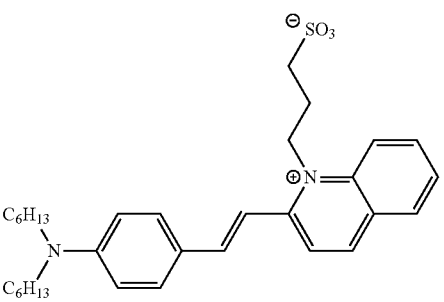 | 537.9 | 532 | 640 | CS0081 |
| 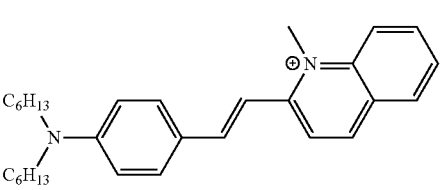 | 429.8 (M+) | 532 | 640 | CS0085 |

TABLE 1-continued
| Structure | MS | Emission | Excitation | Reference # |
|---|---|---|---|---|
| 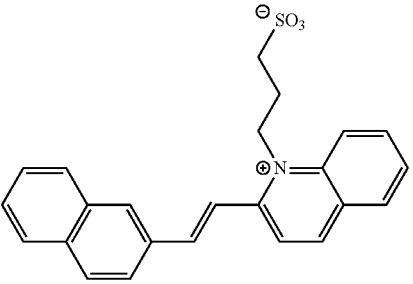 | 404.6 | 400 | 550 | CS0086 |
|  | 296.4 (M⁺) | 400 | 550 | CS0087 |
| 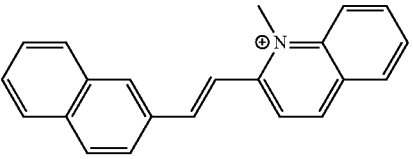 | 365.6 | 468 | 620 | CS0117 |
|  | 711.8 (M⁺) | 480 | 620 | CS0121 |
| 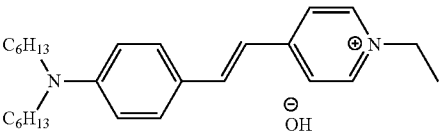 | 393.6 (M⁺) | 480 | 620 | CS0112 |
|  | 406.3 (M²⁺) | 480 | 620 | CS0158 |
| 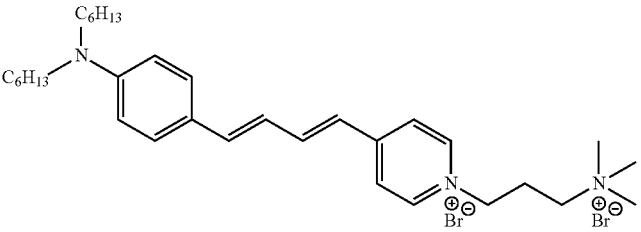 | 491.8 (M²⁺) | 516 | 702 | CS0155 |

TABLE 1-continued

| Structure | MS | Optical Property (in DMSO) Emission | Excitation | Reference # |
|---|---|---|---|---|
| 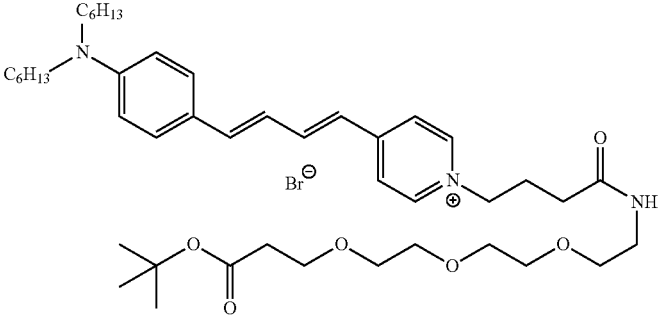 | 737.2 (M+) | 516 | 702 | CS0147 |
| 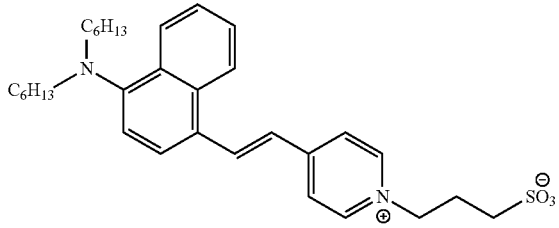 | 537.8 | 462 | 654 | CS0038 |
| 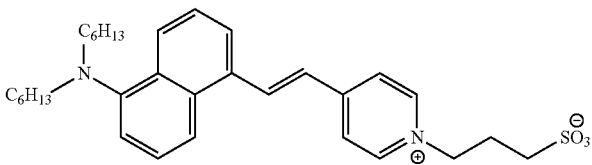 | 537.8 | not fluorescent | | CS0071 |
| 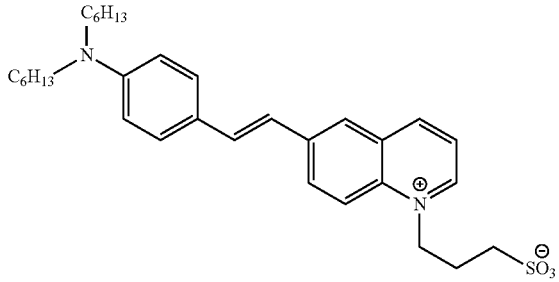 | 537.8 | not fluorescent | | CS0072 |
| 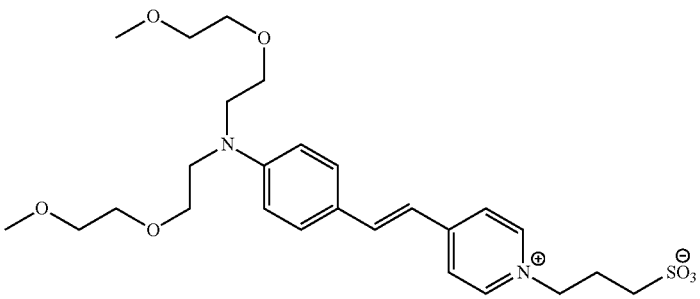 | 523.7 | | | CS000X |

In some embodiments, combinations of dyes are used. In some embodiments, a combination of dyes having varying binding properties is used, such that the dye mix finds use with target proteins having different structural characteristics. Other dyes (e.g., dyes known in the field) may also find use in embodiments described herein.

One advantage of some embodiments described herein is the ability of the assays to be performed in complex samples (e.g., those containing non-target proteins). In some embodiments, samples that find use with the TSAs described herein include cells (e.g., cell culture, cell sample from a patient, etc.), tissue samples (e.g., tissue from biopsy), cell lysates (e.g., lysed of cells expressing a target/reporter fusion, cell lysate expressing target/reporter fusion in vitro, cell lysate with exogenous target/reporter fusion, etc.), complex reaction mixtures (e.g., in vitro reaction mixtures comprising the components necessary for the assay as well as non-essential components (e.g., non-target proteins, competitor proteins, competitor ligands, etc.), simple in vitro reaction mixtures comprising the components necessary for the assay, etc.), etc.

In some embodiments, reporter and/or BRET signal is detected under conditions that favor protein folding and/or conditions that favor some degree of protein unfolding. Two means of varying conditions are temperature and protein denaturants. For example, lower temperatures (e.g., <50° C., <48° C., <46° C., <44° C., <42° C., <40° C., <38° C., <36° C., 34° C., <32° C., <30° C., and ranges therein (e.g., 30-50° C., 35-45° C., etc.)) favor protein folding, while higher temperatures (e.g., >50° C., >55° C., >60° C., >65° C., >70° C., >75° C., >80° C., >85° C., >90° C., >95° C., and ranges therein (e.g., 60-90, ° C. 55-75° C., etc.)) favor protein unfolding, exposure of hydrophobic regions, and/or aggregation. Similarly, the presence of various denaturants and increasing concentrations thereof, favor protein unfolding. Numerous protein denaturants are known in the art and could be empirically selected for use herein. Without being limited to a particular protein denaturant, exemplary protein denaturants include guanidinium thiocyanate, guanidinium hydrochloride, arginine, sodium dodecyl sulfate (SDS), urea, or any combination thereof. In some embodiments, a combination of one or more protein denaturants and increased temperature is employed.

In some embodiments, the reporter signal and/or BRET signal (e.g., the result of energy transfer from bioluminescent protein to environmentally-sensitive hydrophobic dye) is detected under a single condition, and a comparison is made between the signals in the presence and absence of ligand. In such embodiments, the signal is typically detected under partially denaturing conditions, or conditions in which the unbound target protein is beginning to unfold, but it is expected that the ligand-bound target will not be unfolding or will be less unfolded (as will be apparent from the change in signal (e.g., direct reporter signal or BRET signal, depending upon the assay)). Appropriate conditions for such a single-point assay can be determined empirically based on the stability of the particular target protein. In some embodiments, conditions (e.g., temperature and/or denaturant concentration) are selected at or near (e.g., ±5%, ±10%, ±15%, ±20%, ±25%, ±30%, ±35%, ±40%, ±45%, ±50%) the melting temperature ($T_m$) for the target protein. The melting temperature (e.g., in the presence of the intended denaturant concentration) of the target protein can be determined using any of a variety of well-known techniques, including, but not limited to: UV/visible spectrometry, nuclear magnetic resonance spectroscopy (NMR), circular dichroism (CD), etc.

In other embodiments, the reporter signal and/or BRET signal (e.g., the result of energy transfer from bioluminescent protein to environmentally-sensitive hydrophobic dye) is detected under multiple conditions or over a range of conditions (e.g., varying temperature and/or denaturant concentration), and a comparison is made between the signals in the presence and absence of ligand. In such embodiments, signal may be detected at a first condition in which both the ligand-bound and inbound target are expected to be well folded. Under such conditions, similar signals are typically (although not always) expected in both the presence and absence of ligand. In some embodiments, signal is also detected under one or more additional conditions (e.g., increasing temperature, increasing pressure, and/or increasing denaturant concentration) approaching and/or exceeding the expected $T_m$ (e.g., under the denaturant concentration) of the target protein in the absence of ligand. As increasingly unfavorable folding conditions are applied, a difference will be observed between the signal (e.g., from a direct reporter signal or BRET signal, depending upon the assay) from a ligand-bound sample and an unbound target sample.

The number of conditions to assay may be made by weighing factors such as: desired speed of the assay, desired precision/accuracy of the measurements, affinity of binding to be detected, etc. For example, in some embodiments, an assay detects signal under a first condition in which the target is well-folded, a second condition near the $T_m$ of the unbound target, and a third condition in which the unbound target is expected to be unfolded and/or aggregated. These conditions may be determined empirically using the methods described herein or other techniques for monitoring protein folding that are known in the field. As another example, an assay makes stepwise (e.g., every 0.1° C., every 0.2° C., every 0.5° C., every 1.0° C., every 2.0° C., every 5.0° C., etc.) signal detections (e.g., from reporter and/or BRET) over a range of temperatures (e.g., from: 10° C., 15° C., 20° C., 25° C., 30° C., 35° C., 40° C., etc.; to: 50° C., 55° C., 60° C., 65° C., 70° C., 75° C., 80° C., 85° C., 90° C., 95° C., etc.), and or a range of denaturant concentrations.

In some embodiments, a melt-curve analysis is performed for each sample, according to the detected signals at the various conditions assayed. In some embodiments, a visual or automated analysis of the melt-curves in the presence and absence of ligand reveals target/ligand interaction or binding. In some embodiments, a melting temperature ($T_m$) is calculated for each sample, according to the detected signals at the various conditions assayed. In some embodiments, a comparison of $T_m$'s in the presence and absence of ligand reveals target/ligand interaction or binding.

In some embodiments, assays described herein are performed in cells, e.g., live intact cells, or in a lysate of cells. In such embodiments, a nucleic acid construct encoding a target/reporter fusion may be transfected or transformed into cells in order to allow expression of the fusion within cells (e.g., live intact cells, cells in which the assay will be performed, cells which will be lysed before the assay is performed, etc.). In some embodiments, assays described herein provide the detection of molecular interactions between a target and ligand within a cell, e.g., a live intact cell, or in living organisms (e.g., bacteria, yeast, eukaryotes, mammals, primates, human, etc.). In some embodiments, a target/reporter fusion protein is expressed in the cell, e.g., a live intact cell, or whole organism, and signal is detected under various conditions in the presence and absence of ligand. In some embodiments, cells are transiently and/or stably transformed or transfected with vector(s) (e.g., encoding target/reporter fusion protein, structural complement (e.g., NLPep and NLPoly), etc.). In some embodiments, transgenic organisms are generated that code for the necessary assay components (e.g., target/reporter fusion protein, structural complement (e.g., NLPep and NLPoly), etc.) for carrying out the assays described herein. In other embodiments, vectors are injected into whole organisms. A suitable vector may be viral (e.g., lentivirus, AAV, etc.) or non-viral (e.g., plasmid, bacmid, etc.). In some embodiments, in addition to encoding a target/reporter fusion, a vector further comprises elements to allow/promote expression of as much.

In some embodiments, other assay components not expressed in cells or organisms (e.g., reporter substrate, ligand, environmentally-sensitive hydrophobic dye, etc.) are added to the cell or organism exogenously. In embodiments in which assays are not performed in vivo, the target/reporter fusion may also be added exogenously.

Embodiments described herein provide compositions, systems, and methods that are useful in a variety of fields including basic research, medical research, drug discovery, etc. The reagents and assays described herein are not limited to any particular applications, and any useful application should be viewed as being within the scope of the present invention.

Typical applications that make use of embodiments described herein involve the monitoring/detection of protein-ligand interactions. Such assays are useful for monitoring molecular interactions under any suitable conditions (e.g., in vitro, in vivo, in situ, whole animal, etc.), and find use in, for example, drug discovery, elucidating molecular pathways, studying equilibrium or kinetic aspects of complex assembly, high throughput screening, etc.

In some embodiments, assays are used to elucidate the affinity of, or understand the interaction of, a protein of interest and a potentially associated entity of interest (protein, nucleic acid, small molecule, etc.) under complex conditions (e.g., intracellularly).

Embodiments described herein find use in drug screening and/or drug development. For example, the interaction of a small molecule drug or an entire library of small molecules with target protein of interest (e.g., therapeutic target) is monitored (e.g., within a physiologically-relevant cell line, etc.). In some embodiments, drug screening applications are carried out in a high through-put format to allow for the detection of the binding of tens of thousands of different molecules to a target, or to test the effect of those molecules on the binding of a ligand.

In some embodiments, provided herein is the detection of target/ligand interactions in living organisms (e.g., bacteria, yeast, eukaryotes, mammals, primates, human, etc.) and/or cells. In some embodiments, cells are transiently and/or stably transformed or transfected with vector(s) (e.g., encoding target/reporter fusions, complement polypeptide, etc.). In some embodiments, transgenic organisms are generated that code for the necessary components (e.g., encoding target/reporter fusions, complement polypeptide, etc.) to carry out the assays described herein. In other embodiments, vectors are injected into whole organisms.

EXPERIMENTAL

Example 1

Materials and Methods

Method for Expression Plasmid Construction for Full Length NANOL UC-Target Fusions (Applies to Examples Using Full Length NANOL UC)

To produce NANOLUC fusions with protein targets of interest, pF31K Nluc [CMV/Neo] and pF32 [CMV/Neo] were used to place NANOLUC at the N-terminus or the C-terminus of the target protein (respectively) using the manufacturer's protocol (Promega). cDNAs encoding the following target proteins were made and were a 100% match to their respective NCBI reference sequence identifiers; CDK2, DHFR, KDR, SRC, EZH2, HDAC1, BRD4, MAPK14, LCK, ABL, DDR1, and BTK.

Method for Expression Plasmid Construction for NLPep and NLPoly NLPep and NLPoly Target Fusions (Pep86-CDK2, CDK2-Pep86, CDK2-Nluc156, CDK2-Pep11S)

For plasmid constructions, the source of CDK2 was pFN21-CDK2 (Promega FLEXI vector backbone) received from Kazusa DNA Research Institute (Chiba, Japan).

Pep86-CDK2: This construct was built by transferring CDK2 to the FLEXI vector, pF-n5K3-86-GSSG-barnase, according to Promega's recommended protocols in the FLEXI vector technical manual.

CDK2-Pep86: This construct was built by transferring CDK2 to the FLEXI vector, pF-c5K3-barnase-GSSG-86, according to Promega's recommended protocols in the FLEXI vector technical manual.

CDK2-Nluc156: This construct was built by first transferring CDK2 to the FLEXI vector, pF-nCA-barnase-GSSG-Nluc, according to Promega's recommended protocols in the FLEXI vector technical manual. The Nluc portion of this vector was then modified by site-directed mutagenesis to contain a G51A substitution. It was then further modified by site-directed mutagenesis to contain a deletion of the sequence coding for the final 13 amino acids of Nluc.

CDK2-11S: This construct was built by transferring CDK2 to the FLEXI vector, pF-c5K3-barnase-GS SG-11S, according to Promega's recommended protocols in the FLEXI vector technical manual.

Each of the constructs contained a GSSG linker between CDK2 and either NLPep86, Nluc156, or NLpoly11S.

Method for Generation of Purified Detection NLPep86 and NLPoly11S

NLPep86 (SEQ ID NO: 5) (containing an N-terminal acetyl and C-terminal amide) was made synthetically by Peptide 2.0. NLpoly11S (SEQ ID NO: 6)(NLpoly11S with C-terminal 6His tag) was isolated by transforming E. coli KRX cells (Promega) with the FLEXI vector, pF6HisCK, and then overexpressing and purifying according to Promega's recommended protocol for isolating His-tagged proteins (HISLINK Protein Purification technical manual).

General Protocol Cell Transfection for All Experiments:

NANOLUC-target or NLPep and NLPoly-target fusion constructs were diluted into carrier DNA (pGEM3ZF-, Promega) at a mass ratio of 1:10 or 1:100 (mass/mas) prior to forming FuGENE HD complexes according to the manufacturer's protocol (Promega). DNA:FuGENE complexes were formed at a ratio of 1:3 (ug DNA/uL FuGENE), then 1 part of the transfection complexes was then mixed with 20 parts (volume/volume) of HeLa cells (ATCC) suspended at a density of $2 \times 10^5$ in DMEM (Gibco)+10% FBS (Hyclone), followed by incubation in a humidified, 37° C./5% $CO_2$ incubator for 18-24 hours.

Example 2

Direct-Luciferase-Detection Thermal Shift Assay with Full Length NANOLUC

Experiments were conducted during development of embodiments of the present invention to demonstrate direct detection of the stabilization of a target protein by the interaction with a target ligand via temperature dependent alteration of luminescent signal from a luciferase fused to the target protein.

To ensure the NANOLUC (Nluc) luminescent signal was originating from intact cells after the cells had been exposed to a temperature gradient, the integrity of the cells and cell membranes after heating was investigated as well as measuring Nluc activity in the cells versus in the supernatant.

HeLa cells were heated to different temperatures, cooled at room temperature, mixed with trypan blue, and the absolute cell numbers and dye exclusion were measured. Parallel samples were spun down to pellet, and the cells and supernatant collected.

HeLa cells were transfected with CDK2-Nluc DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of $2\times10^4$ cells/well in a 100 uL/well volume, and the plates were placed into a thermal cycler (MW Research) where the samples were heated individually at different temperatures spanning a gradient of 42-66° C. across the plate for 3 minutes followed by cooling at 22° C. for 3 minutes. To determine the absolute cell count and viability, 10 uL cell aliquot from each temperature was mixed with an equal volume of 0.4% (w/v) trypan blue exclusion dye solution (Life technologies) and analyzed using the Countess Automated cell counter (Life Technologies). To determine where the Nluc luminescent signal was originating, the 96-well PCR plate was centrifuged to pellet the cells. The supernatant and cell pellet was collected separately and placed into a 96-well tissue culture plate (Corning). Furimazine Live Cell Substrate (Promega) was added to a final concentration of 1×, and luminescence was measured on a BMG Clariostar luminometer equipped with a 450 nm BP filter. Samples were also collected from a 96-well PCR plate that had not undergone centrifugation and placed into a tissue culture plate followed by addition of furimazine substrate and luminescence analysis.

Figure 1B:
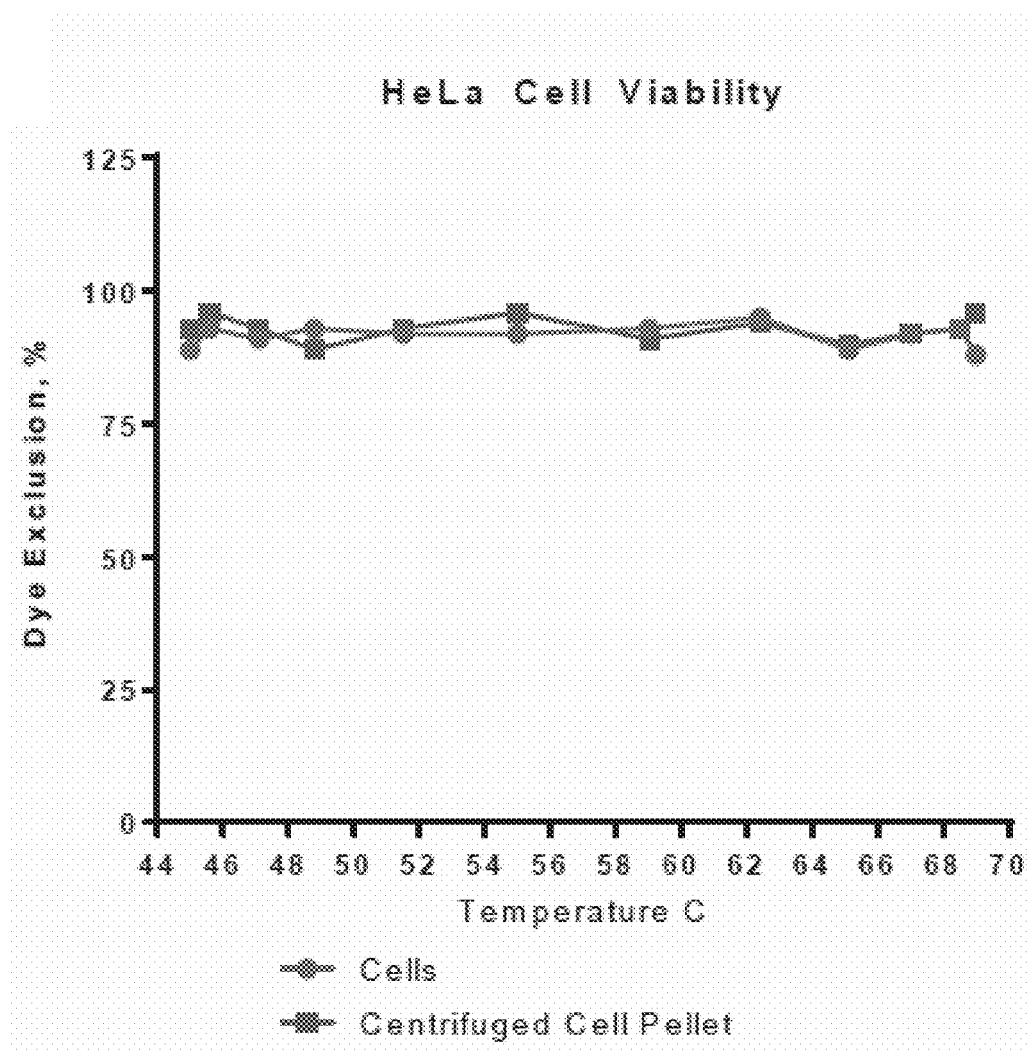
Figure 1C:
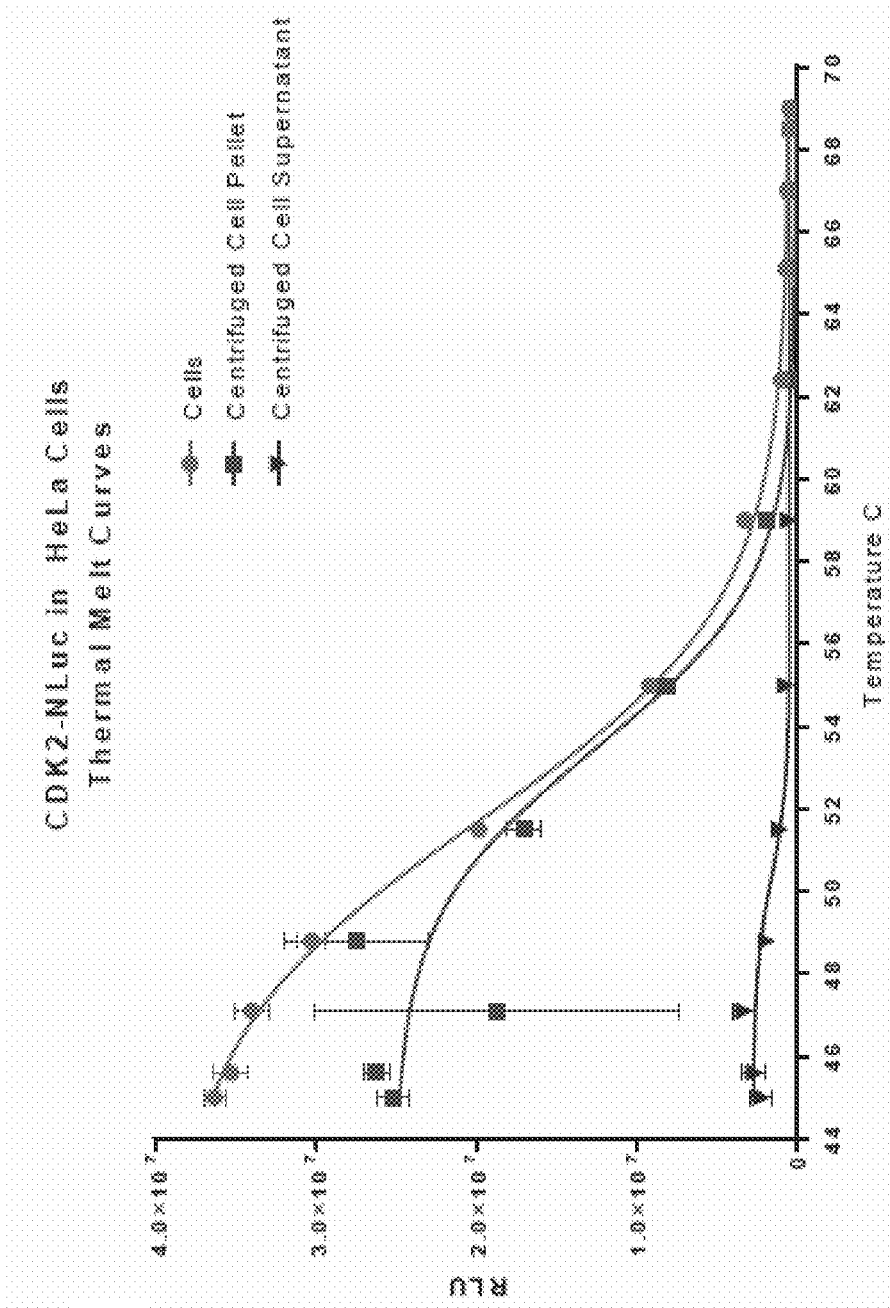

The data demonstrates that the cells were not lysed, even at higher temperatures, since the number of cells remained unchanged and membranes remained intact as determined by dye exclusion (FIG. 1A-B). Furthermore, the Nluc activity was retained in the cells with the luciferase signal originating from the cell samples and not the supernatant post-heat treatment (FIG. 1C).

Example 3

Direct-Luciferase-Detection Thermal Shift Assay with Full Length NANOLUC

Experiments were conducted during development of embodiments of the present invention to demonstrate direct detection of the stabilization of a target protein by the interaction with a target ligand via temperature dependent alteration of luminescent signal from a luciferase fused to the target protein.

HeLa cells were transfected separately with the various Nluc-fusion DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of $2\times10^4$ cells/well in a 90 uL/well volume, and either treated with 10 uL/well of a 10% DMSO solution (Sigma) or 10 uL/well of a 0.5 mg/ml solution of digitonin (Sigma). The plates were placed into a thermal cycler (MW Research) where the samples were heated individually at different temperatures spanning a gradient of 42-66° C. across the plate for 3 minutes followed by cooling at 22° C. for 3 minutes. 90 uL/well samples were then transferred to a tissue culture plate (Corning), and Furimazine Live Cell Substrate (Promega) was added to a final concentration of 1×. Luminescence was measured on a BMG Clariostar luminometer equipped with a 450 nm BP filter. Data was normalized by relating RLU signals to the RLU of the lowest temperature for the respective sample. Data was then fitted to obtain apparent melting temperature where the protein is precipitating ($T_{agg}$ values) using the Boltzmann Sigmoidal equation with Graphpad Prism software.

Figure 2A:
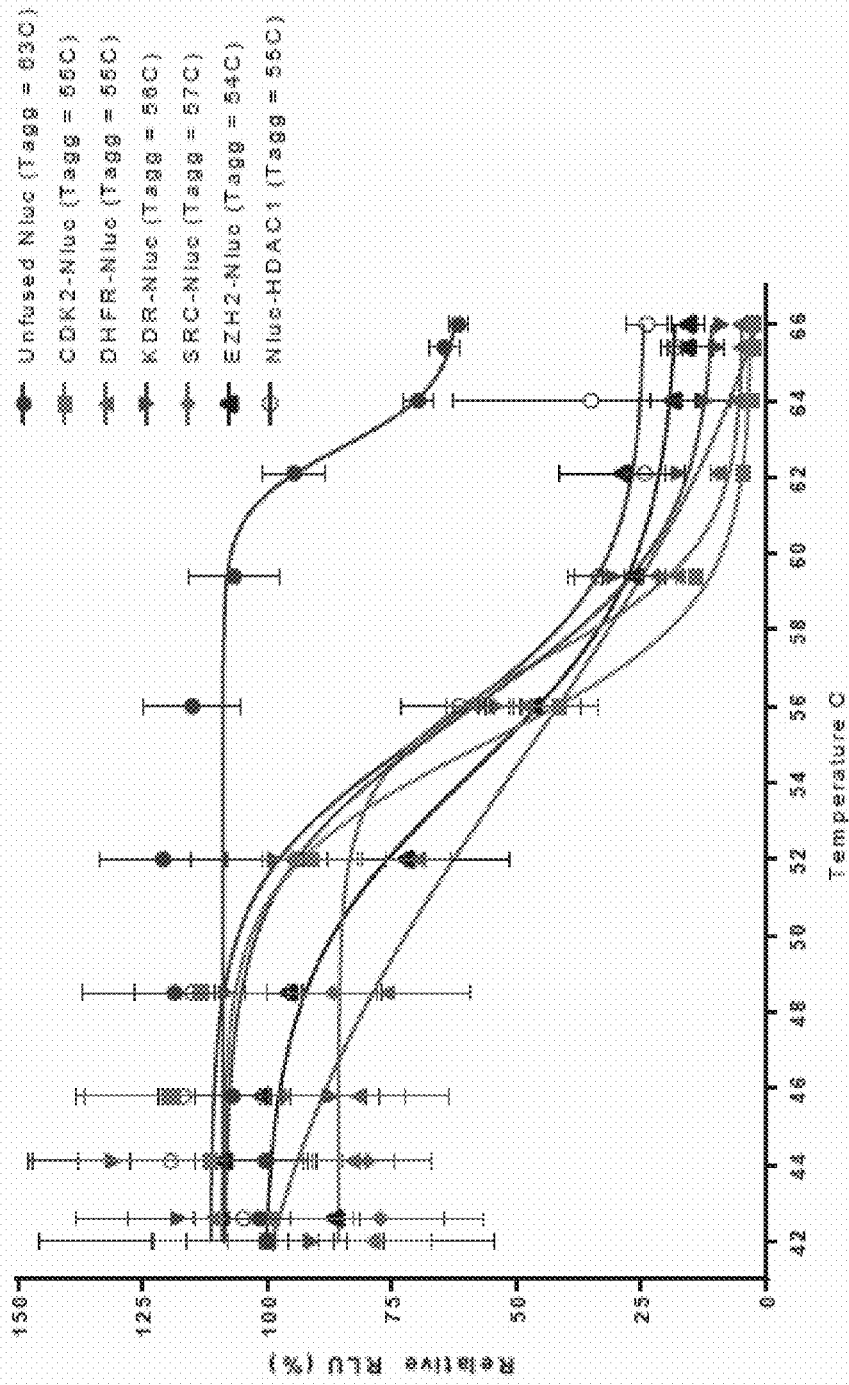
FIGS. 2A-B show analysis of melting temperatures of several example target-NANOLUC (Nluc) fusions across a range of target classes as determined by NANOLUC activity (RLU) in live, intact cells (FIG. 2A) and digitonin-treated (FIG. 2B) mammalian cells when exposed to a temperature gradient.
Figure 2B:
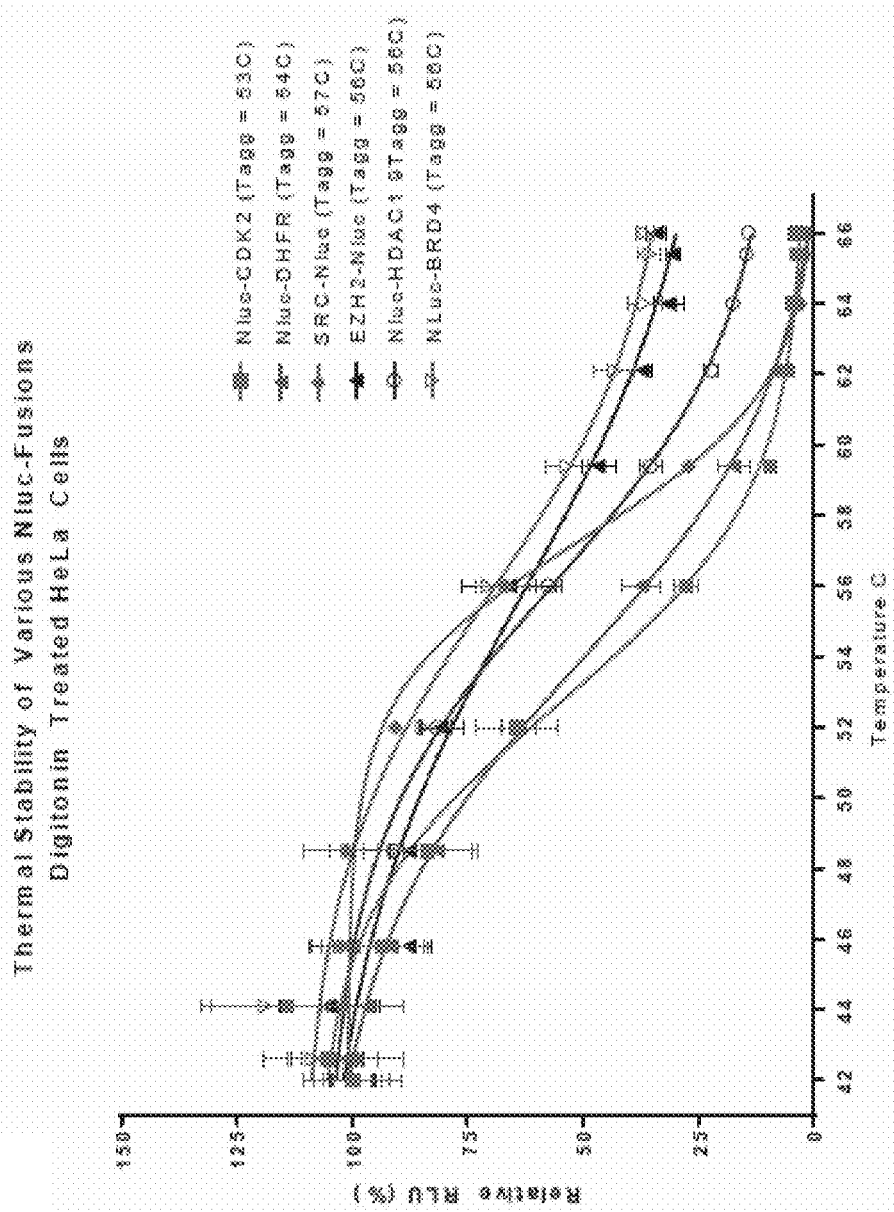

Protein thermal melt curves can be generated for Nluc-target fusions spanning several different target classes and subcellular localization (nuclear, cytoplasmic, and membrane) in live, intact cells (FIG. 2A), and cells that had been treated with the detergent digitonin (FIG. 2B) with results indicating each protein displayed distinct melting curves as analyzed by luciferase activity and reported as apparent aggregation temperatures ($T_{agg}$).

Example 4

Direct-Luciferase-Detection Thermal Shift Assay with Full Length NANOLUC

Experiments were conducted during development of embodiments of the present invention to demonstrate direct detection of the stabilization of a target protein by the interaction with a target ligand via temperature dependent alteration of luminescent signal from a luciferase fused to the target protein.

To determine if a shift in $T_{agg}$ after exposure to stabilizing ligand can be detected, the thermal melt curve for CDK2, which showed a distinct melt curve in the presence of DMSO (control), was evaluated. When AZD5438 (a drug known to bind to CDK2) was added, clear shifts in the melting curves with increases in apparent $T_{agg}$ were detected compared to DMSO controls and analyzed by luciferase activity indicating specific binding and protein stabilization of the CDK2 by the inhibitor.

HeLa cells were transfected with CDK2-Nluc or Nluc-CDK2 DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of $2\times10^4$ cells/well in a 90 uL/well volume and treated with 10 uL of 10% DMSO (Sigma), 10 uL/well of a 0.5 mg/ml solution of digitonin (Sigma), 10 uL of 1 mM AZD5438 (Selleckchem) in 10% DMSO, and/or 10 uL of 1 mM Methotrexate (Sigma) in 10% DMSO. The plates were then incubated for 1-2 hours in a humidified, 37° C./5% $CO_2$ incubator. The plates were placed into a thermal cycler (MW Research) where the samples were heated individually at different temperatures spanning a gradient of 42-66° C. across the plate for 3 minutes followed by cooling at 22° C. for 3 minutes. 90 uL/well samples were then transferred to a tissue culture plate (Corning), and Furimazine Live Cell Substrate (to a final concentration of 1×; Promega) or NANOGLO lytic reagent (Promega) was added. Luminescence was measured on a BMG Clariostar luminometer equipped with a 450 nm BP filter. Data was normalized by relating RLU signals to the RLU signals of the lowest temperature for the respective sample. Data was then fitted to obtain apparent melting temperature where the protein is precipitating ($T_{agg}$ values) using the Boltzmann Sigmoidal equation with Graphpad Prism software.

Figure 4:
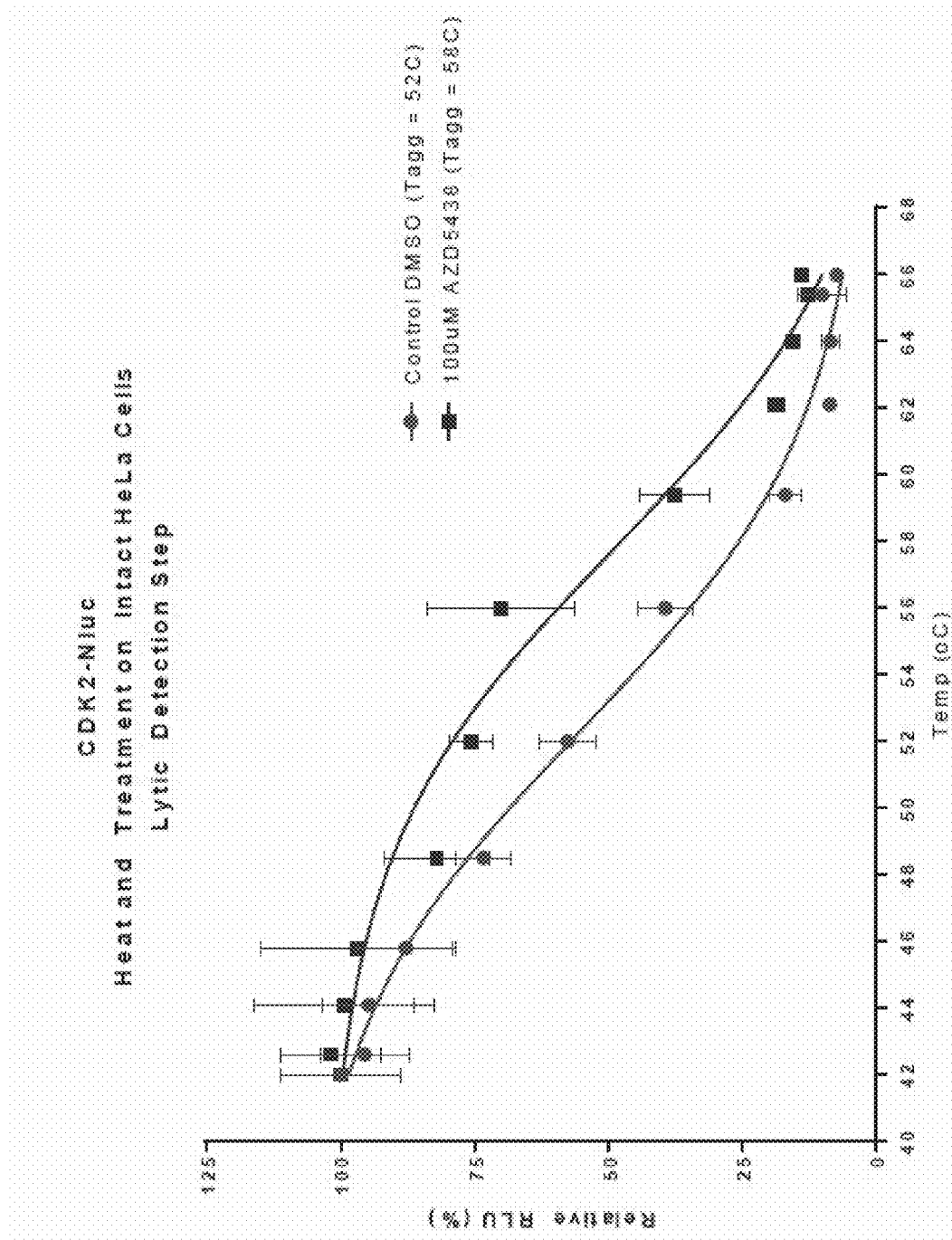
FIG. 4 shows a detection of an increase in melting temperature for CDK2-Nluc as determined by NANOLUC activity (RLU) after binding to a stabilizing ligand in live mammalian cells subsequently lysed with lytic NANOGLO Detection Reagent (Promega) and subsequently exposed to a temperature gradient.

The thermal shift induced by AZD5438 was insensitive to Nluc positioning on the N- or C-terminal of CDK2 (FIG. 3) and was demonstrated in live (FIG. 3A-B) and digitonin-treated cells (FIG. 3C-D) as well as in cells lysed with the addition of lytic substrate (FIG. 4).

Example 5

Direct-Luciferase-Detection Thermal Shift Assay with Full Length NANOLUC

Experiments were conducted during development of embodiments of the present invention to demonstrate direct detection of the stabilization of a target protein by the interaction with a target ligand via temperature dependent alteration of luminescent signal from a luciferase fused to the target protein.

To demonstrate that the assay can be applied to a larger class of kinase proteins, specific melt curves and thermal shifts across a panel of kinases were obtained after exposure to specific stabilizing compounds. HeLa cells, expressing different kinase Nluc-target fusions with varying functions and subcellular localization, were exposed to compounds known to target each one and then exposed to the temperature treatment.

HeLa cells were transfected separately with the various Nluc-target DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of $2 \times 10^4$ cells/well in a 80 uL/well volume and treated with 10 uL/well of a 0.5 mg/ml solution of digitonin (Sigma), 10 uL of 1 mM AZD5438 (Selleckchem) in 10% DMSO, 10 uL of 0.25 mM AMG548 (Tocris) in 10% DMSO, 10 uL of 1 mM Dasatinib (BioVision) in 10% DMSO, or 10 uL of 0.5 mM Staurosporine (LC Laboratories) in 10% DMSO. The plates were then incubated for 1 hour in a humidified, 37° C./5% $CO_2$ incubator. The plates were placed into a thermal cycler (MW Research) where the samples were heated individually at different temperatures spanning a gradient of 42-66° C. across the plate for 3 minutes followed by cooling at 22° C. for 3 minutes. Furimazine Live Cell Substrate (Promega) was added to a final concentration of 1× in 20 uL/well volume. 100 uL/well was then transferred to a tissue culture plate (Corning), and luminescence was measured on a BMG Clariostar luminometer equipped with a 450 nm BP filter. Data was normalized by relating RLU signals to the RLU signals of the lowest temperature for the respective sample. Data was then fitted to obtain apparent melting temperature where the protein is precipitating ($T_{agg}$ values) using the Boltzmann Sigmoidal equation with Graphpad Prism software.

Obvious shifts in melting temperature, with increases in $T_{agg} \geq 4°$ C. in all cases, were seen when the cells were treated with the specific binding compounds as compared to DMSO controls for each kinase tested (FIGS. 5A-F).

Example 6

Direct-Luciferase-Detection Thermal Shift Assay with Full Length NANOLUC

Experiments were conducted during development of embodiments of the present invention to demonstrate direct detection of the stabilization of a target protein by the interaction with a target ligand via temperature dependent alteration of luminescent signal from a luciferase fused to the target protein.

To demonstrate the assay's ability to determine compound target selectivity and highlight the assay's potential screening capabilities for proposed inhibitors, an assay against two kinase target fusions, CDK2-Nluc and Nluc-ABL1, with the same panel of kinase inhibitors known to have different selectivity against these two kinase targets was performed. The assay accurately validated ligand selectivity, and rank order potency, with the compounds known to bind to CDK2 and/or ABL1 causing a shift in melting temperature (apparent $T_{agg}$), and those compounds known not to have affinity towards CDK2 and/or ABL1 leaving the melting temperature relatively unchanged, as compared to the DMSO control.

HeLa cells were transfected separately with CDK2-Nluc or Nluc-ABL1 DNA at a 1:100 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of $2 \times 10^4$ cells/well in a 90 uL/well volume and treated with 10 uL of 10% DMSO (Sigma) or 10 uL of a 1 mM stock solution of test compound in 10% DMSO. Test compounds included: Staurosporine (LC Laboratories), Dasatinib (BioVision), Nilotinib (BioVision), Ponatinib (SYNKinase), AMG548 (Tocris), SB203580 (AdipoGen), and AZD5438 (Selleckchem). The plates were then incubated for ½ hour in a humidified, 37° C./5% $CO_2$ incubator prior to addition of 10 uL/well of a 0.5 mg/ml solution of digitonin (Sigma) and 10% DMSO (Sigma). The plates were placed into a thermal cycler (MW Research) where the samples were heated individually at different temperatures spanning a gradient of 42-66° C. across the plate for 3 minutes followed by cooling at 22° C. for 3 minutes. Furimazine Live Cell Substrate (Promega) was added to a final concentration of 1× in 20 uL/well volume. 100 uL/well was then transferred to a tissue culture plate (Corning), and luminescence was measured on a BMG Clariostar luminometer equipped with a 450 nm BP filter. Data was normalized by relating RLU signals to the RLU of the lowest temperature for the respective sample. Data was then fitted to obtain apparent melting temperature where the protein was precipitating ($T_{agg}$ values) using the Boltzmann Sigmoidal equation with Graphpad Prism software.

Figure 6A:
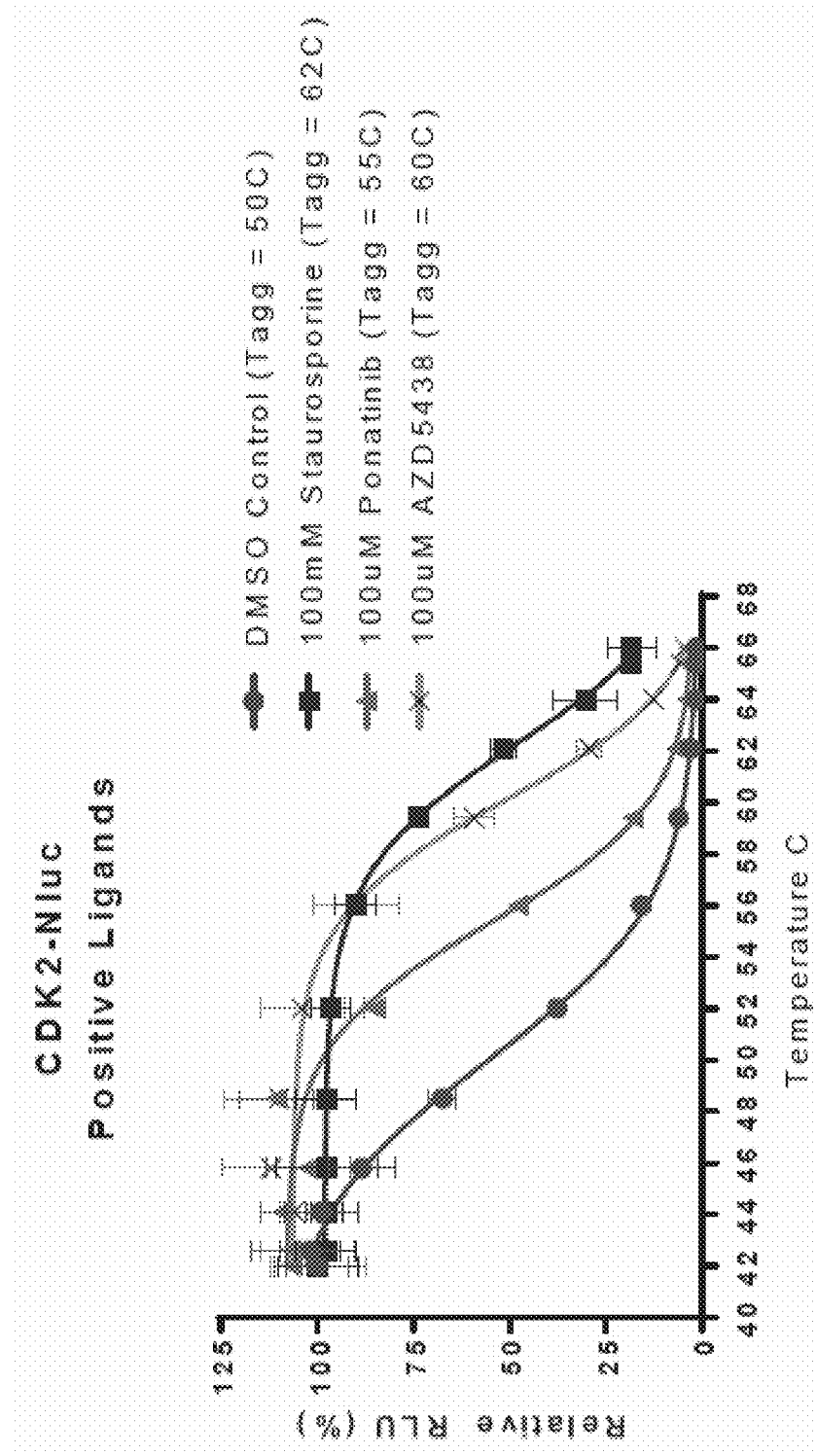
FIGS. 6A-D show detection of an increase in melting temperatures or no change in melting temperatures for CDK2-Nluc and Nluc-ABL1 as determined by NANOLUC activity (RLU) after incubation with a panel of compounds thus displaying compound selectivity for the cytoplasmic targets in mammalian cells subsequently exposed to digitonin and a temperature gradient.
Figure 6B:
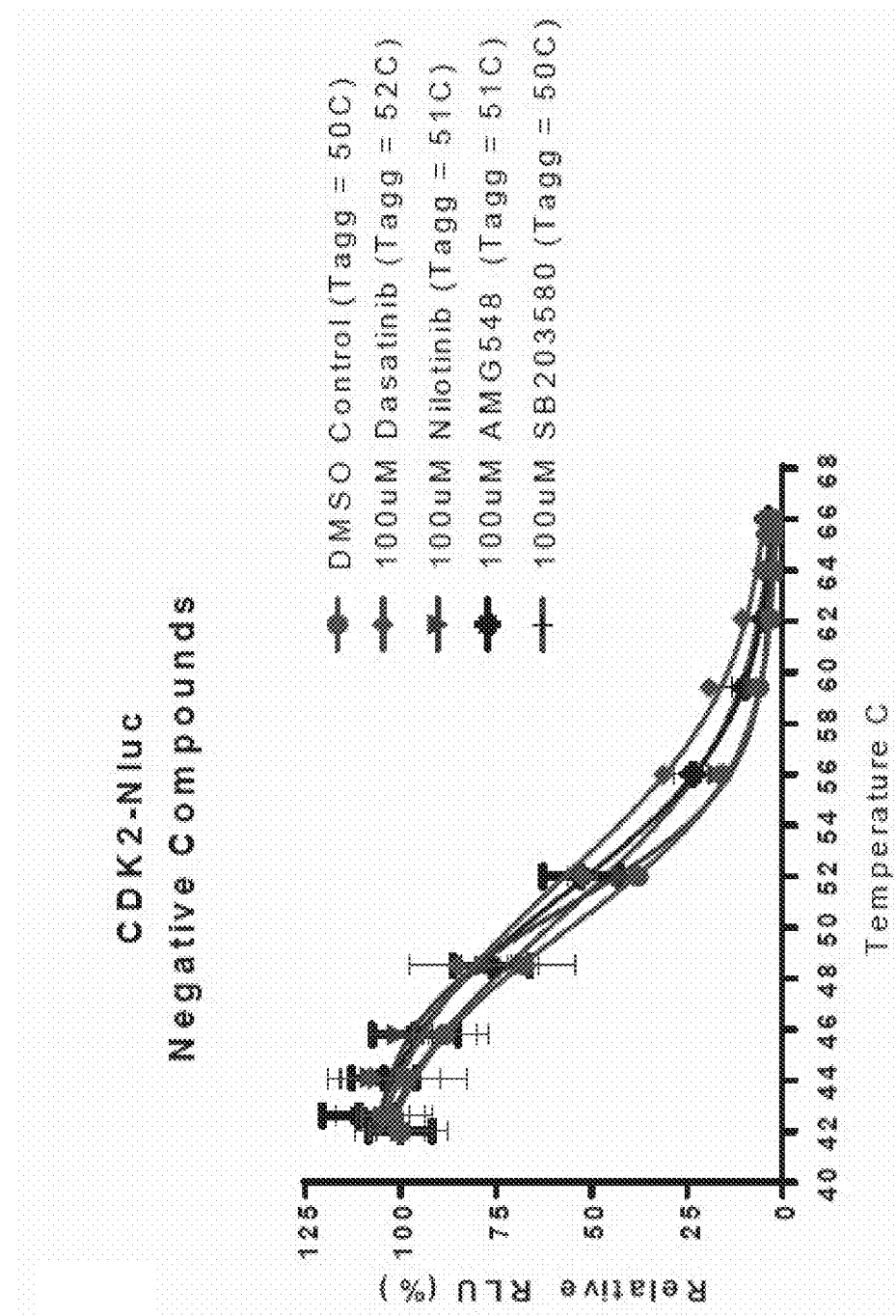
Figure 6C:
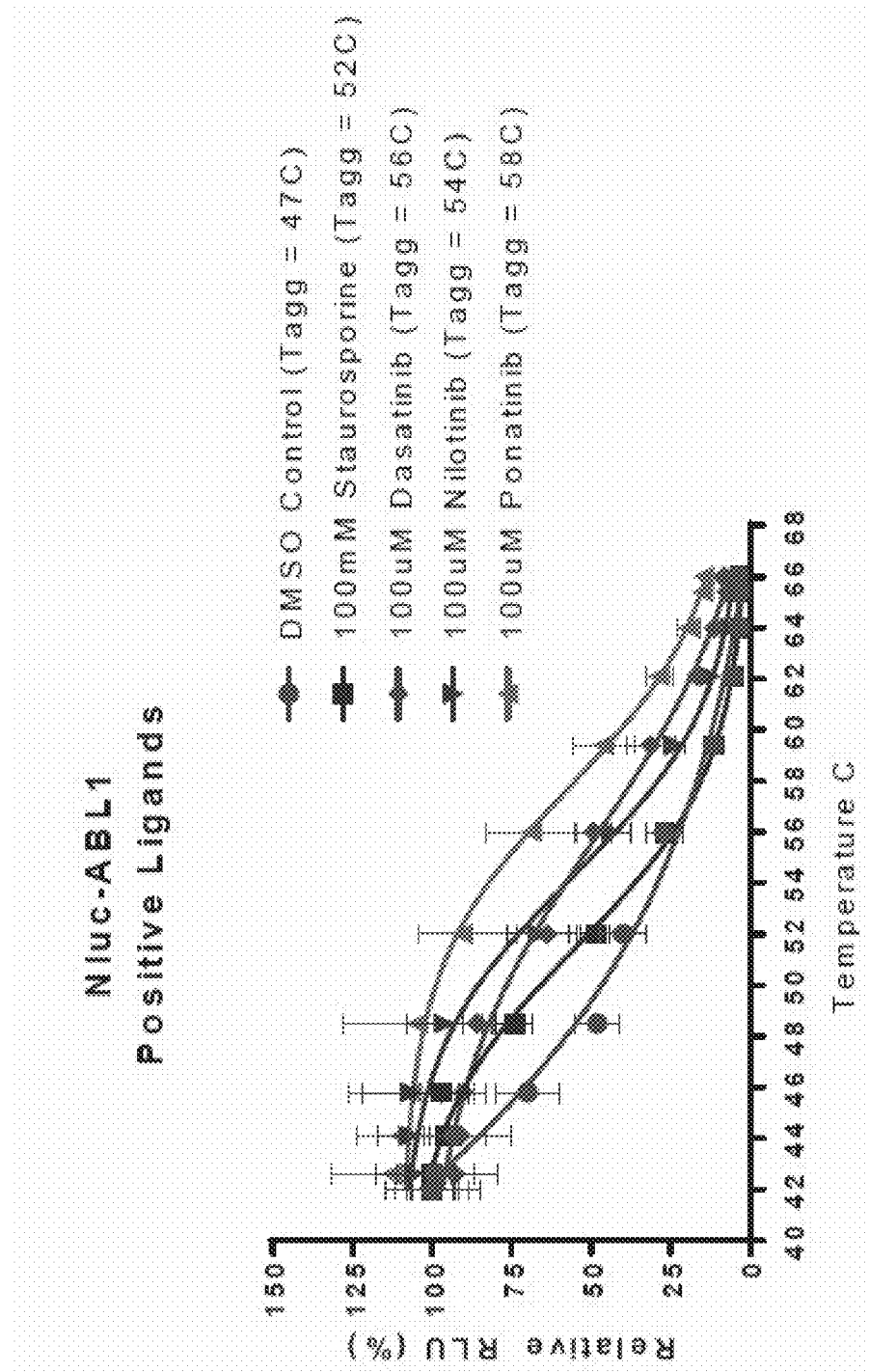
Figure 6D:
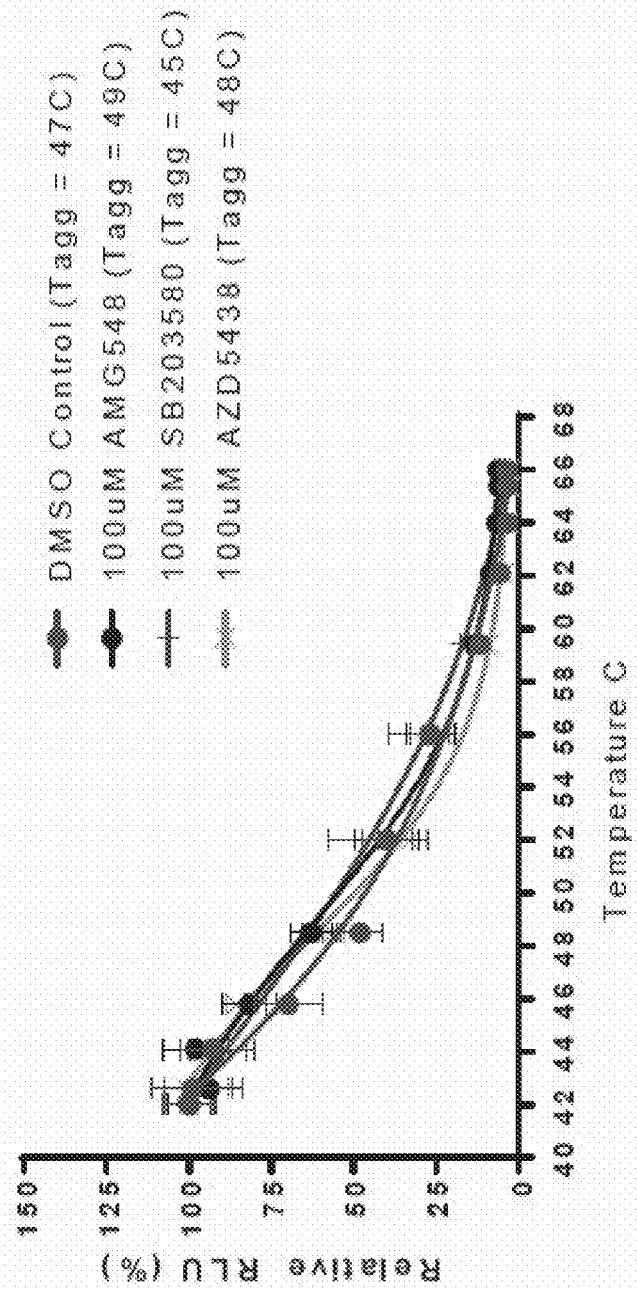

For the CDK2 target fusion, the known target inhibitors, staurosporine, Ponatinib, and AZD5438, all caused a significant increase in apparent $T_{agg}$. Dasatinib, Nilotinib, AMG548, and SB20358, which are all compounds not known to interact with CDK2, did not result in a significant shift in apparent $T_{agg}$ compared to DMSO controls when incubated with cells expressing the CDK2-Nluc fusion (FIG. 6A-B). Similarly, Staurosporine, Dasatinib, Nilotinib, and Ponatinib, all of which target ABL1 kinase, caused a significant shift in apparent $T_{agg}$ compared to DMSO controls, whereas the negative ligands AMG548, SB203580, and AZD5438 did not as expected (FIG. 6C-D).

Example 7

Direct-Luciferase-Detection Thermal Shift Assay with Full Length NANOLUC

Experiments were conducted during development of embodiments of the present invention to demonstrate direct detection of the stabilization of a target protein by the interaction with a target ligand via temperature dependent alteration of luminescent signal from a luciferase fused to the target protein.

To demonstrate the TSA approach described herein can be applied broadly, the experiment performed in FIGS. 6A-D was repeated using a target protein that maintains a nuclear subcellular localization and originated from a drug target class very different from kinases. Cells were transfected with HDAC1-Nluc fusions and tested against a panel of known HDAC inhibitors with Staurosporine, a kinase inhibitor, serving as an additional negative control with DMSO.

HeLa cells were transfected with HDAC1-Nluc DNA at a 1:100 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of $2×10^4$ cells/well in a 90 uL/well volume and treated with 10 uL of 10% DMSO (Sigma) or 10 uL of a 1 mM stock solution of test compound in 10% DMSO. Test compounds included: SAHA (TOCRIS), Mocetinostat (Selleckchem), Panibinostat (LC Laboratories), ACY1215 (Selleckchem), and Staurosporine (LC Laboratories). The plates were then incubated for ½ hour in a humidified, 37° C./5% $CO_2$ incubator prior to addition of 10 uL/well of a 0.5 mg/ml solution of digitonin (Sigma) and Furimazine Live Cell Substrate (final concentration 1× (Promega)). The plates were placed into a thermal cycler (MW Research) where the samples were heated individually at different temperatures spanning a gradient of 42-66° C. across the plate for 3 minutes followed by cooling at 22° C. for 3 minutes. 100 uL/well was then transferred to a tissue culture plate (Corning), and luminescence was measured on a BMG Clariostar luminometer equipped with a 450 nm BP filter. Data was normalized by relating RLU signals to the RLU of the lowest temperature for the respective sample. Data was then fitted to obtain apparent melting temperature where the protein is precipitating ($T_{agg}$ values) using the Boltzmann Sigmoidal equation with Graphpad Prism software.

Figure 7:
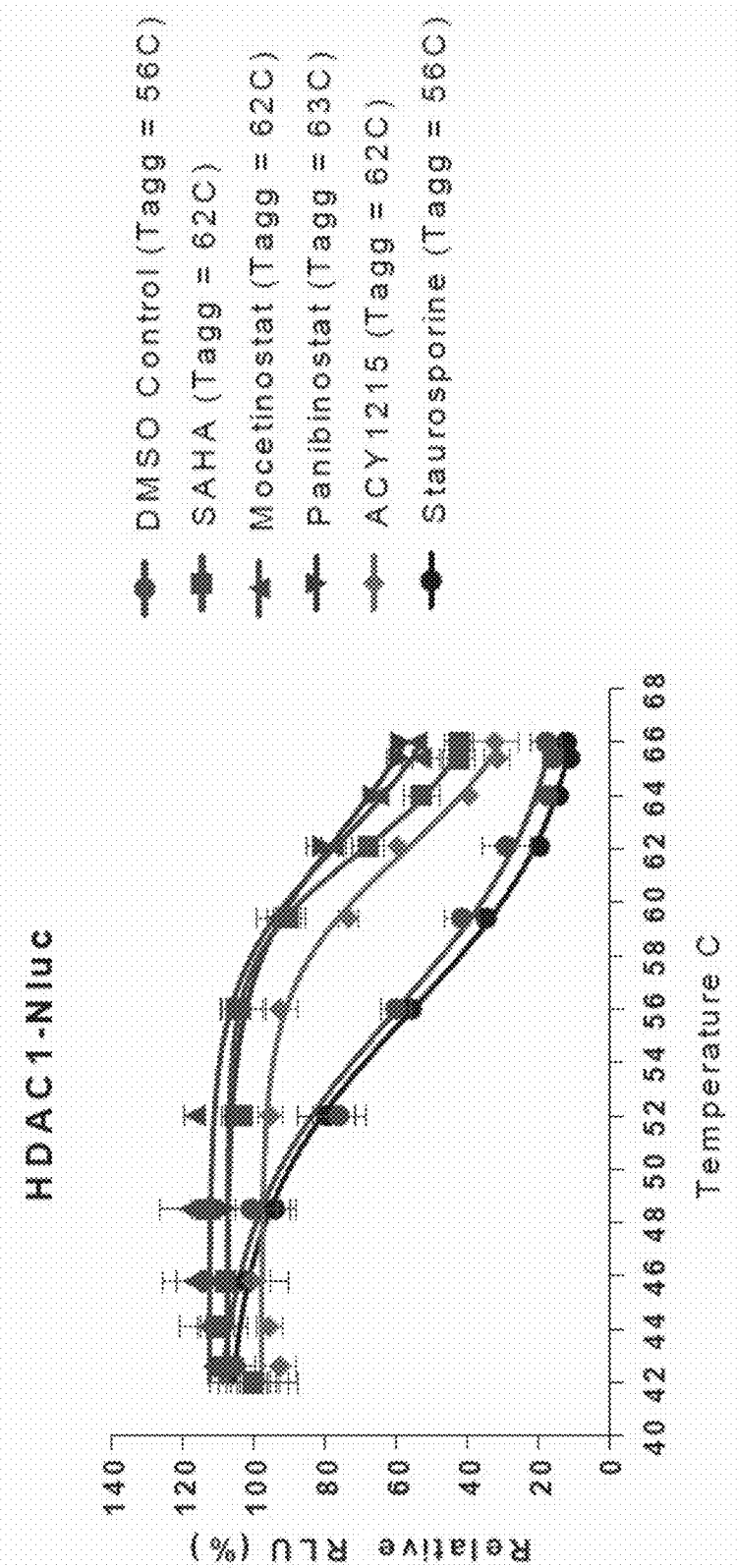
FIG. 7 shows detection of an increase in melting temperatures or no change in melting temperatures for HDAC1-Nluc as determined by NANOLUC activity (RLU) after incubation with a panel of compounds thus displaying compound selectivity for the nuclear target in mammalian cells and subsequently exposed to digitonin and a temperature gradient.

All four HDAC known inhibitors (SAHA, Mocetinostat, Panibinostat, and ACY1215) produced a significant shift in melting temperature (apparent $T_{agg}$) indicating ligand binding compared to the controls as analyzed by luciferase activity (FIG. 7).

Example 8

Direct-Luciferase-Detection Thermal Shift Assay with Full Length NANOLUC

Experiments were conducted during development of embodiments of the present invention to demonstrate direct detection of the stabilization of a target protein by the interaction with a target ligand via temperature dependent alteration of luminescent signal from a luciferase fused to the target protein.

To determine if the assay can be performed when the ligands added are not maintained under equilibrium conditions, the assay was performed with a compound washout step. This would also confirm that the target engagement was happening in live cells as well as have the ability to analyze binding kinetics.

HeLa cells were transfected with KDR-Nluc or DHFR-Nluc at a 1:10 DNA ratio and incubated overnight in t75 tissue culture flasks (Corning). Media was aspirated and replaced with media containing a final concentration of 100 uM BIBF-1120 (Selleckchem) for cells expressing KDR-Nluc or 100 uM Methotrexate (Sigma) for cells expressing DHFR-Nluc. DMSO at a final concentration of 1% was used as control and added to each cell population. The cells were allowed to incubate with compounds for 2 hours in a humidified, 37° C./5% $CO_2$ incubator. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). Cells were seeded into 96-well tall-chimney PCR plate (Fisherbrand) at a density of $2×10^4$ cells/well in a 100 uL/well and placed into a thermal cycler (MW Research) where the samples were heated individually at different temperatures spanning a gradient of 42-66° C. across the plate for 3 minutes followed by cooling at 22° C. for 3 minutes. 90 uL/well was then transferred to a tissue culture plate (Corning), and Furimazine Live Cell Substrate (final concentration 1× (Promega)) was added. Luminescence was measured on a BMG Clariostar luminometer equipped with a 450 nm BP filter. Data was normalized by relating RLU signals to the RLU of the lowest temperature for the respective sample. Data was then fitted to obtain apparent melting temperature where the protein is precipitating ($T_{agg}$ values) using the Boltzmann Sigmoidal equation with Graphpad Prism software.

Figure 8A:
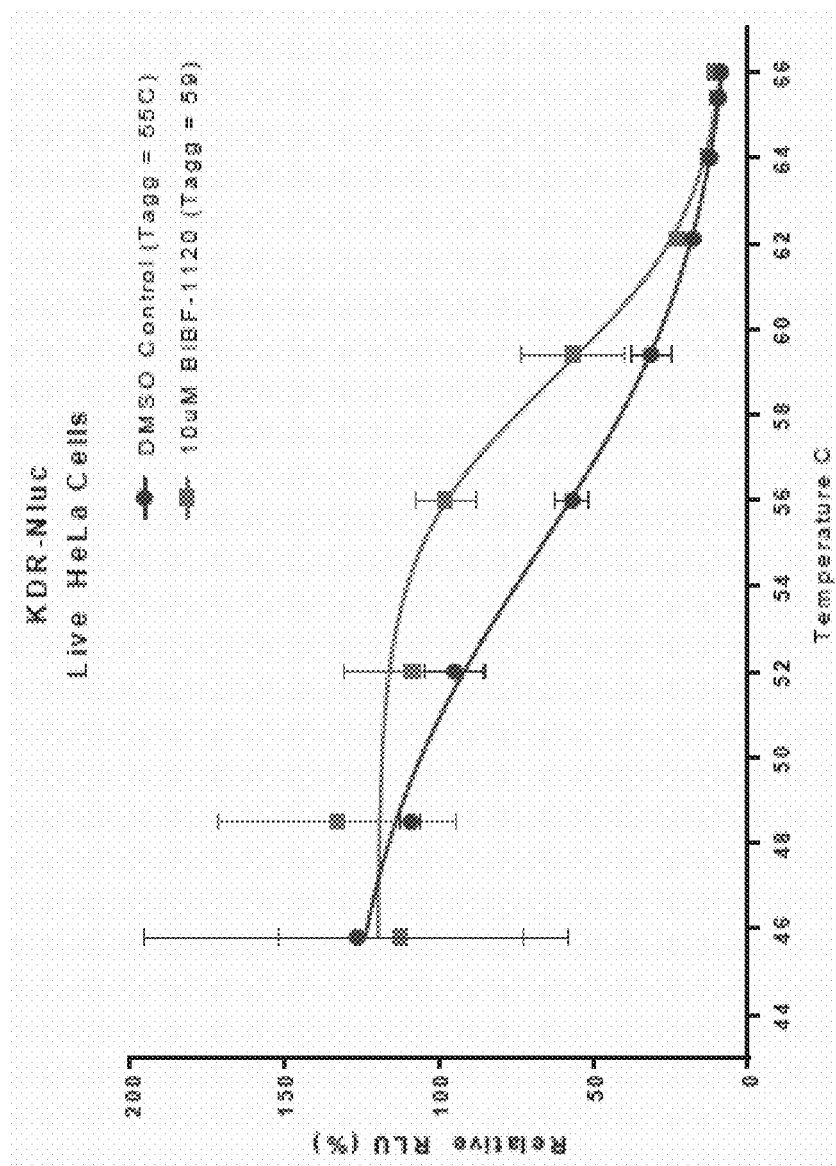
FIGS. 8A-B show detection of an increase in melting temperature for the targets KDR-Nluc and DHFR-Nluc as determined by NANOLUC activity (RLU) after incubation with stabilizing ligand in mammalian cells subsequently harvested with the compound being washed out and then subjected to a temperature. With this compound washout step, the experiment is analyzed not under compound equilibrium conditions and has the ability to analyze binding kinetics. KDR is a membrane protein highlighting another subcellular location that the assay is able to monitor. This assay was performed with live, intact cells throughout the whole assay conditions.
Figure 8B:
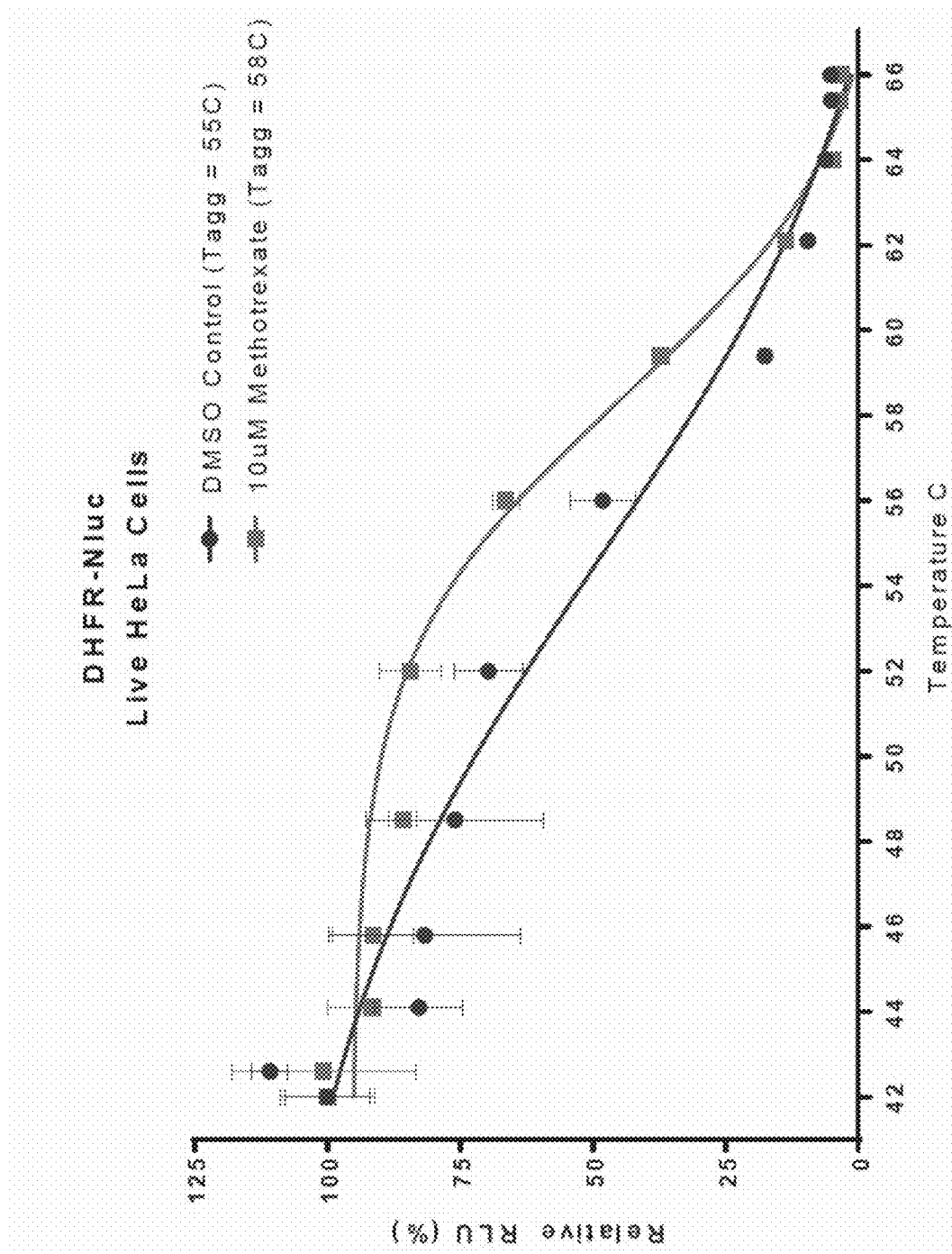

FIGS. 8A-B show detection of an increase in melting temperature for the targets KDR-Nluc (FIG. 8A) and DHFR-Nluc (FIG. 8B) as determined by NANOLUC activity (RLU) after incubation with known stabilizing ligand in mammalian cells subsequently harvested with the compound being washed out, and then subjected to a temperature. KDR is a membrane protein highlighting another subcellular location that the assay is able to monitor.

Example 9

Direct-Luciferase-Detection Thermal Shift Assay with NLPep and NLPoly Through Spontaneous Binary Complementation Experiments were conducted during development of embodiments of the present invention to demonstrate direct detection of the stabilization of a target protein by the interaction with a target ligand via temperature dependent alteration of luminescent signal in which the luminescent signal results through spontaneous binary complementation from a peptide fused to the target protein with the complementary subunit present in the detection reagent.

To determine if the luciferase-based thermal shift assay described herein could be performed using a spontaneous binary complementation, the NLPep and NLPoly technology (Promega; See, e.g., U.S. Pub. No. 2014/0348747: herein incorporated by reference in its entirety) was used.

HeLa cells were transfected with CDK2-NLpep86 or NLpep86-CDK2 DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega), which had been reconstituted in DMSO (Sigma). The cells were seeded into 96-well tall-chimney PCR plate (Fisherbrand) at a density of $2×10^4$ cells/well in a 90 uL/well volume and treated with 1 uL of 100% DMSO (Sigma) or 1 uL of a 10 mM stock solution of AZD5438 (Selleckchem) in 10% DMSO, and 10 uL/well of a 0.5 mg/ml solution of digitonin (Sigma). The plates were then incubated for 1-2 hour in a humidified, 37° C./5% $CO_2$ incubator. The plates were placed into a thermal cycler (MW Research) where the samples were heated individually at different temperatures spanning a gradient of 42-66° C. across the plate for 3 minutes followed by cooling at 22° C. for 3 minutes. 90 uL/well was then transferred to a tissue culture plate (Corning), and the complementary subunit, NLpoly11S, was added to a final concentration of 1 uM with Furimazine Live Cell Substrate (final concentration 1× (Promega)). Luminescence was measured on a BMG Clariostar luminometer equipped with a 450 nm BP filter. Data was normalized by relating RLU signals to the RLU of the lowest temperature for the respective sample and subtracting the background luminescence signal generated by NLpoly11S. Data was then fitted to obtain apparent melting temperature where the protein is precipitating ($T_{agg}$ values) using the Boltzmann Sigmoidal equation with Graphpad Prism software.

Figure 9A:
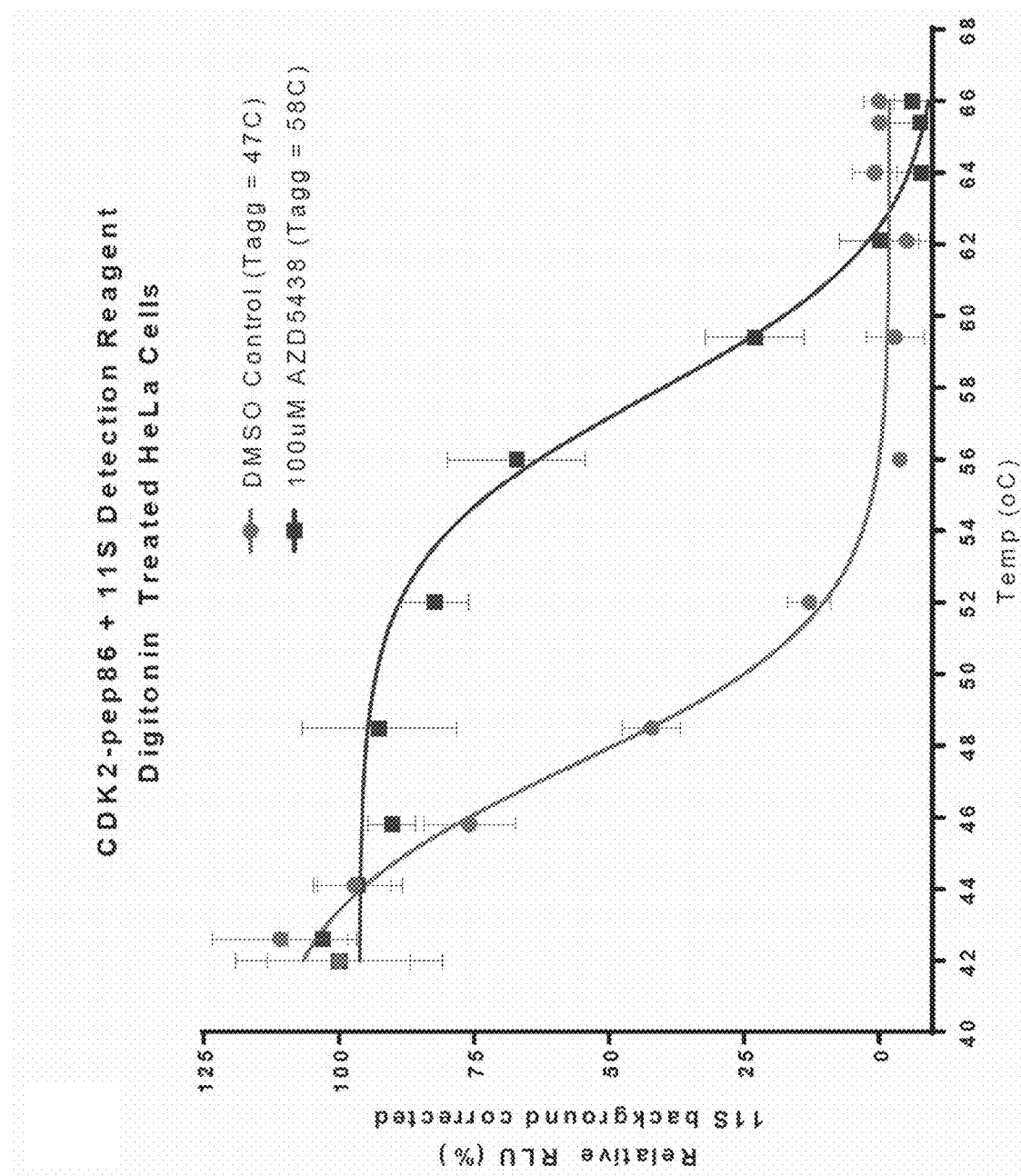
FIGS. 9A-9B show detection of an increase in melting temperature for CDK2-pep86 and pep86-CDK2 as determined by luciferase activity through spontaneous binary complementation after incubation in the presence of a stabilizing ligand in digitonin-treated mammalian cells subsequently exposed to a temperature gradient.
Figure 9B:
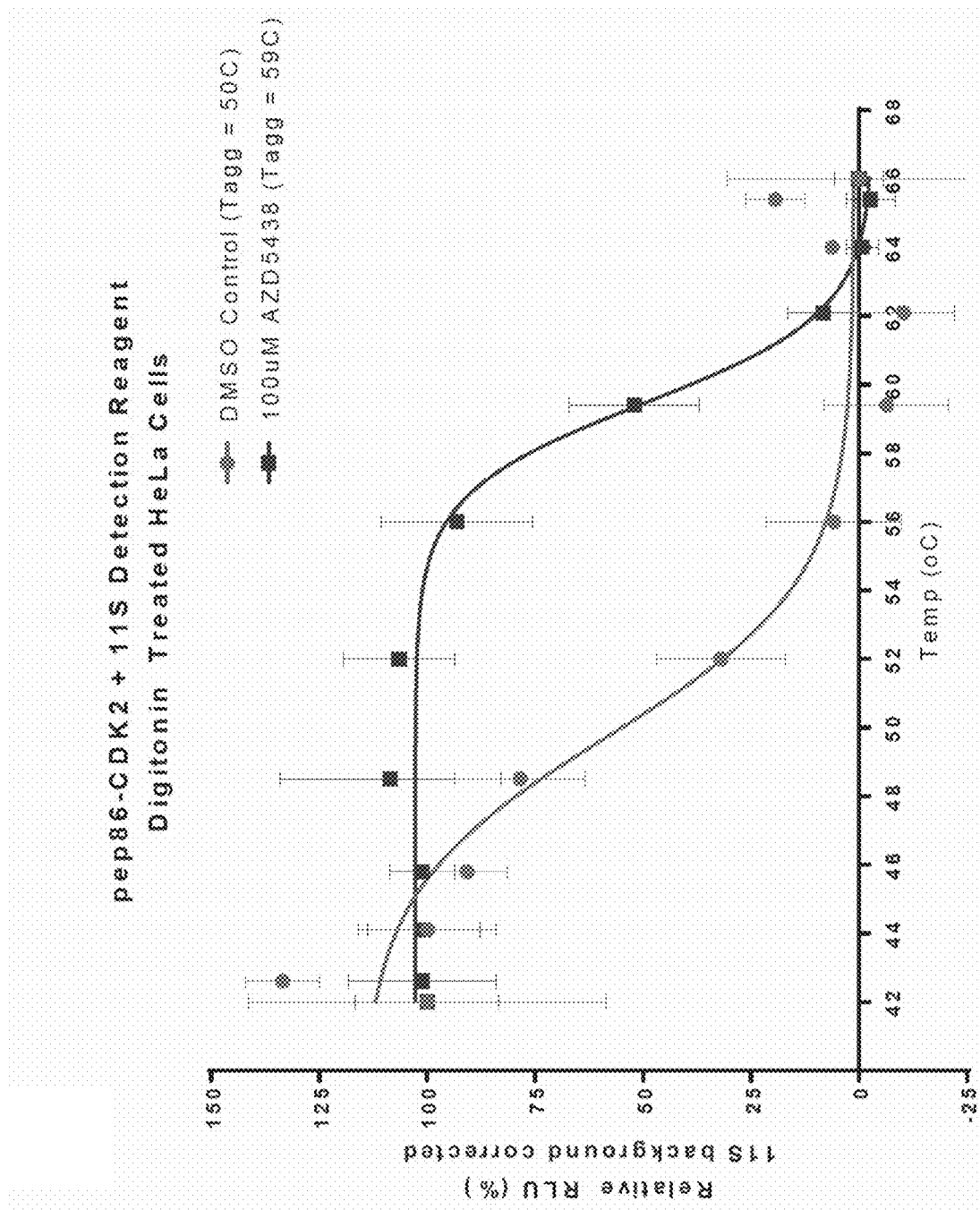

FIG. 9 shows detection of an increase in melting temperature for CDK2-NLpep86 and NLpep86-CDK2 as determined by luciferase activity through spontaneous binary complementation after incubation in the presence of the stabilizing ligand AZD5438 in digitonin-treated mammalian cells subsequently exposed to a temperature gradient and addition of substrate and complementary subunit NLpoly11S as compared to the DMSO control.

Example 10

Direct-Luciferase-Detection Thermal Shift Assay with NLPep and NLPoly Through Spontaneous Binary Complementation Experiments were conducted during development of embodiments of the present invention to demonstrate direct detection of the stabilization of a target protein by the interaction with a target ligand via temperature dependent alteration of luminescent signal in which the luminescent signal results through spontaneous binary complementation from a peptide fused to the target protein with the complementary subunit present in the detection reagent.

The following experiment is similar to Example 9, but used another pair of complementary subunits, NLpoly156 (SEQ ID NO: 7) and NLpep86. NLpoly156 was fused to the target protein, and NLpep86 was placed in the detection reagent.

HeLa cells were transfected with CDK2-Nluc156 DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of 2×10⁴ cells/well in a 90 uL/well volume and treated with 1 uL of 100% DMSO (Sigma) or 1 uL of a 10 mM stock solution of AZD5438 (Selleckchem) in 10% DMSO, and 10 uL/well of a 0.5 mg/ml solution of digitonin (Sigma). The plates were then incubated for 1-2 hour in a humidified, 37° C./5% CO₂ incubator. The plates were placed into a thermal cycler (MW Research) where the samples were heated individually at different temperatures spanning a gradient of 42-66° C. across the plate for 3 minutes followed by cooling at 22° C. for 3 minutes. 90 uL/well was then transferred to a tissue culture plate (Corning), and the complementary subunit, NLpep86, was added to a final concentration of 1 uM with Furimazine Live Cell Substrate (final concentration 1× (Promega)). Luminescence was measured on a BMG Clariostar luminometer equipped with a 450 nm BP filter. Data was normalized by relating RLU signals to the RLU of the lowest temperature for the respective. Data was then fitted to obtain apparent melting temperature where the protein is precipitating ($T_{agg}$ values) using the Boltzmann Sigmoidal equation with Graphpad Prism software.

Figure 10:
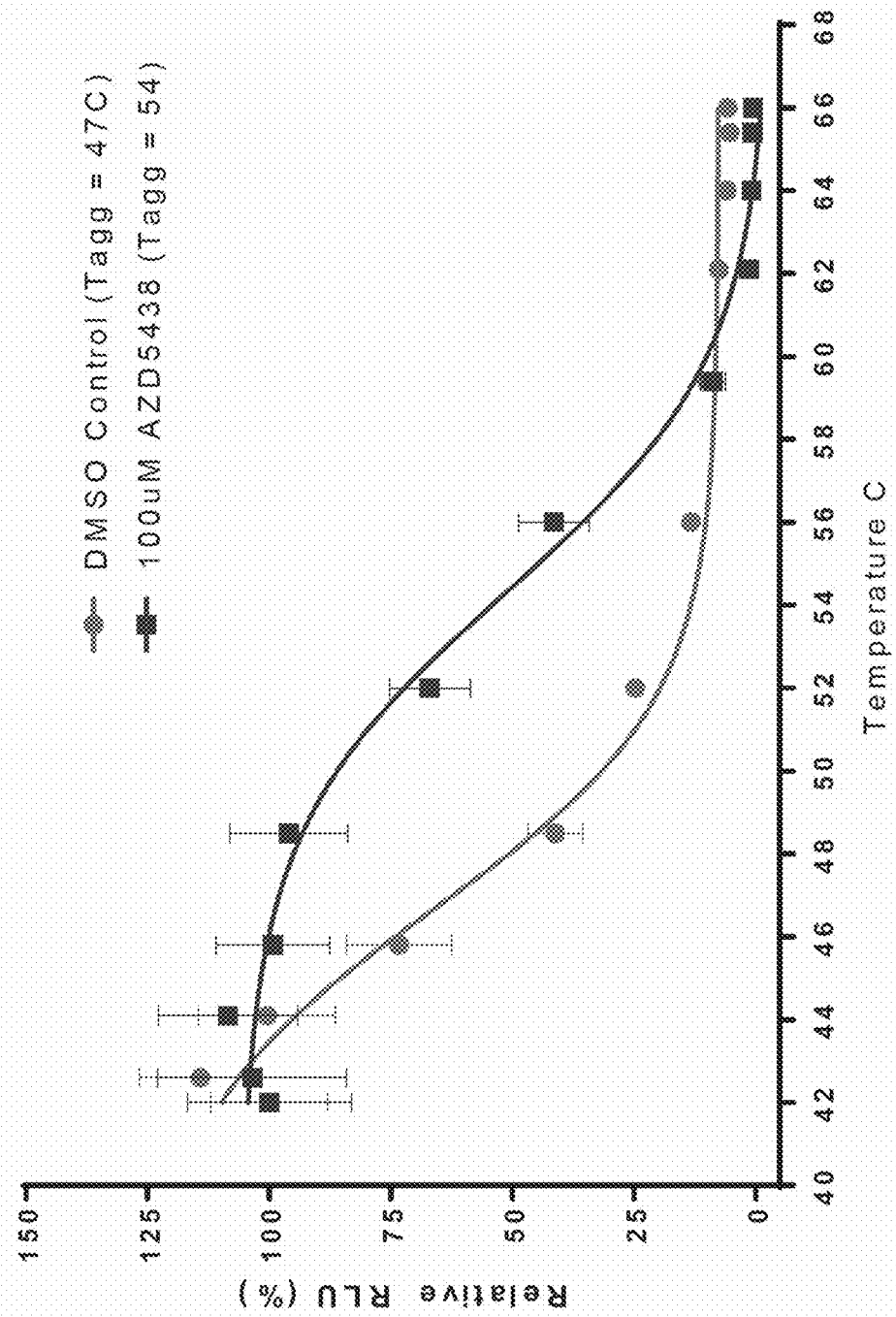
FIG. 10 shows detection of an increase in melting temperature for CDK2-NLuc156 as determined by luciferase activity through spontaneous binary complementation after incubation in the presence of a stabilizing ligand in digitonin-treated mammalian cells subsequently exposed to a temperature gradient.

FIGS. 10A-C demonstrates the detection of an increase in melting temperature for CDK2-NLpoly156 as determined by luciferase activity through spontaneous binary complementation after incubation in the presence of the stabilizing ligand AZD5438 in digitonin-treated mammalian cells subsequently exposed to a temperature gradient and addition of substrate and complementary subunit NLpep86 as compared to the DMSO control.

Example 11

Direct-Luciferase-Detection Thermal Shift Assay with NLPep and NLPoly Through Spontaneous Binary Complementation Experiments were conducted during development of embodiments of the present invention to demonstrate direct detection of the stabilization of a target protein by the interaction with a target ligand via temperature dependent alteration of luminescent signal in which the luminescent signal results through spontaneous binary complementation from a peptide fused to the target protein with the complementary subunit present in the detection reagent.

HeLa cells were transfected with CDK2-NLpep86 or CDK2-NLpoly11S DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of 2×10⁴ cells/well in a 90 uL/well volume and treated with 1 uL of a 100× stock solution in a dilution series of AZD5438 (Selleckchem) in 10% DMSO, and 10 uL/well of a 0.5 mg/ml solution of digitonin (Sigma). The plates were then incubated for 1-2 hour in a humidified, 37° C./5% CO₂ incubator. The plates were placed into a thermal cycler (MW Research) where the samples were heated individually at different temperatures spanning a gradient of 42-66° C. across the plate for 3 minutes followed by cooling at 22° C. for 3 minutes. 90 uL/well was then transferred to a tissue culture plate (Corning) and complementary subunit NLpoly11S or NLpep86 was added to a final concentration of 1 uM with Furimazine Live Cell Substrate (final concentration 1× (Promega)). Luminescence was measured on a BMG Clariostar luminometer equipped with a 450 nm BP filter. For $EC_{50}$ analysis, compound concentration was plotted against RLU, and the data was transformed prior to being fitted using the sigmoidal dose response (variable slope) equation with Graphpad Prism software. For apparent $T_{agg}$ analysis, data was normalized by relating RLU signals to the RLU of the lowest temperature for the respective. Data was then fitted to obtain apparent melting temperature where the protein is precipitating ($T_{agg}$ values) using the Boltzmann Sigmoidal equation with Graphpad Prism software.

Figure 11A:
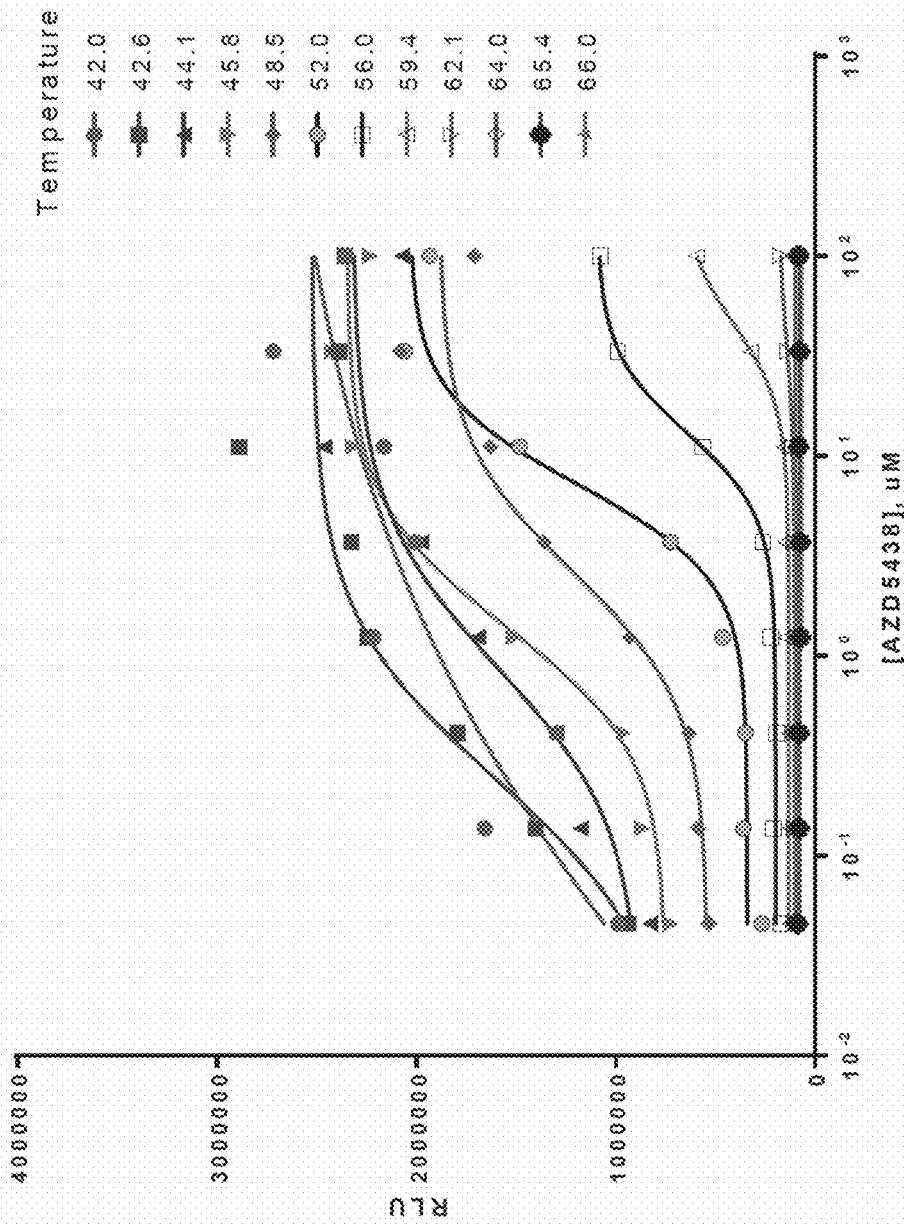
FIGS. 11A-11B show temperature and stabilizing ligand concentration effects on melting temperature of CDK2-pep86 as determined by luciferase activity through spontaneous binary complementation after incubation in the presence of stabilizing ligand in digitonin-treated mammalian cells subsequently exposed to a temperature gradient.
Figure 11B:
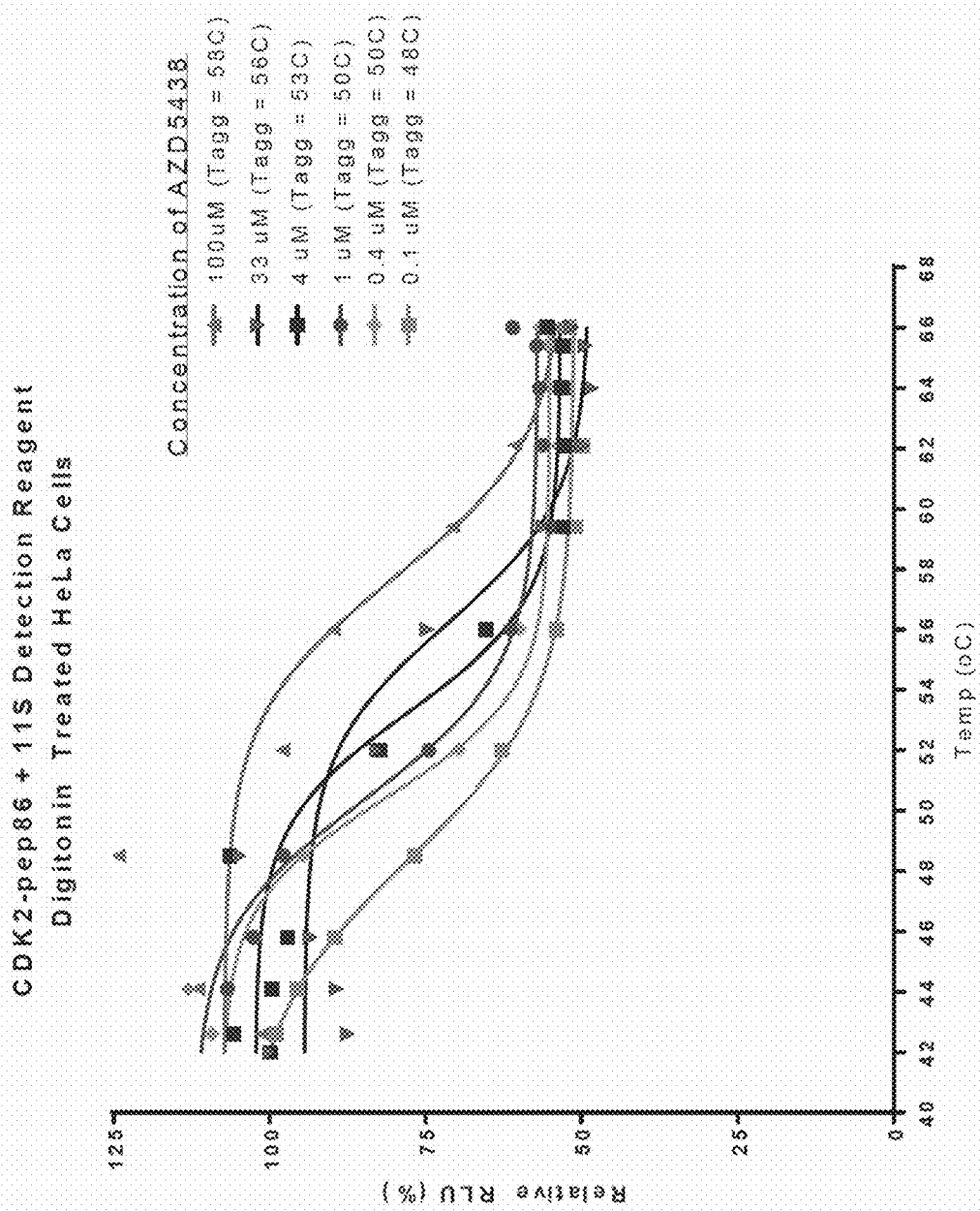
Figure 12A:
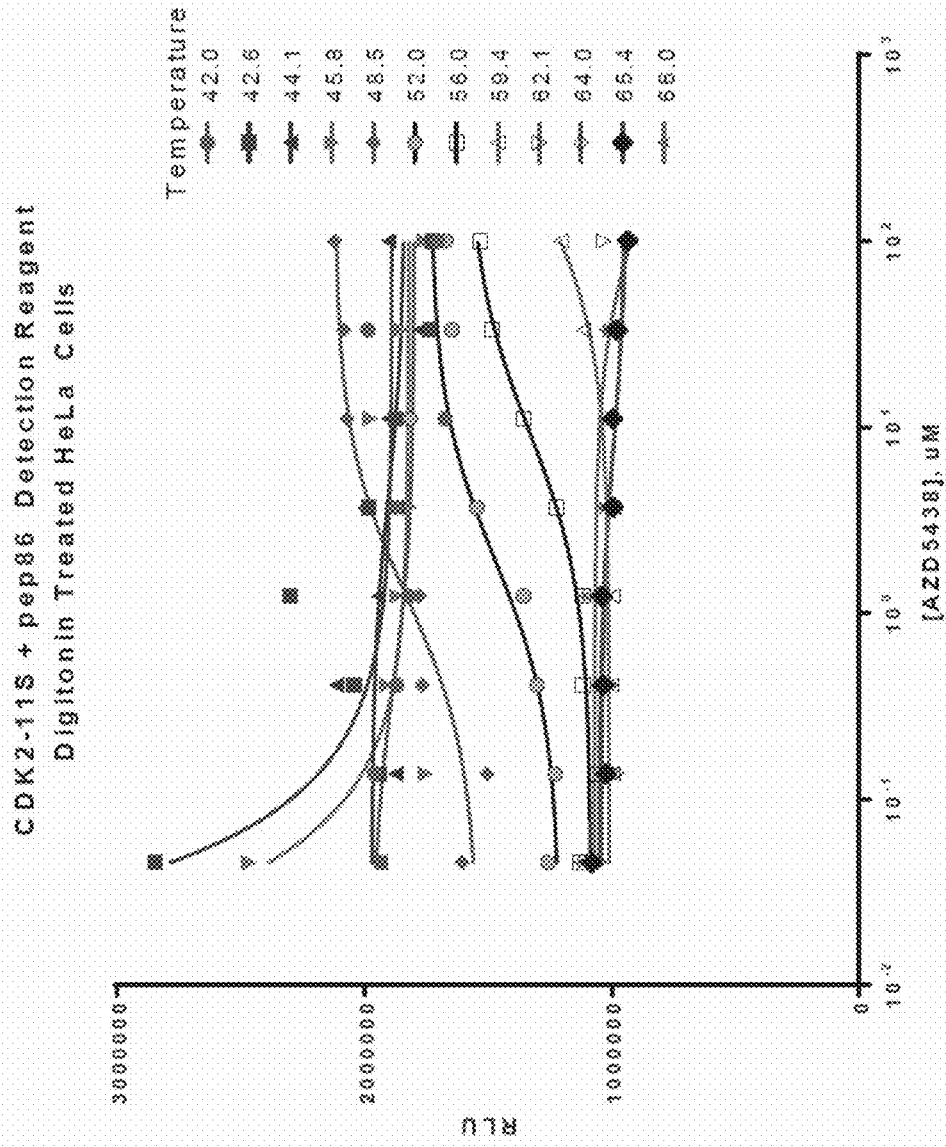
FIGS. 12A-B show temperature and stabilizing ligand concentration effects on melting temperature of CDK2-11S as determined by luciferase activity through spontaneous binary complementation after incubation in the presence of stabilizing ligand in digitonin-treated mammalian cells subsequently exposed to a temperature gradient.
Figure 12B:
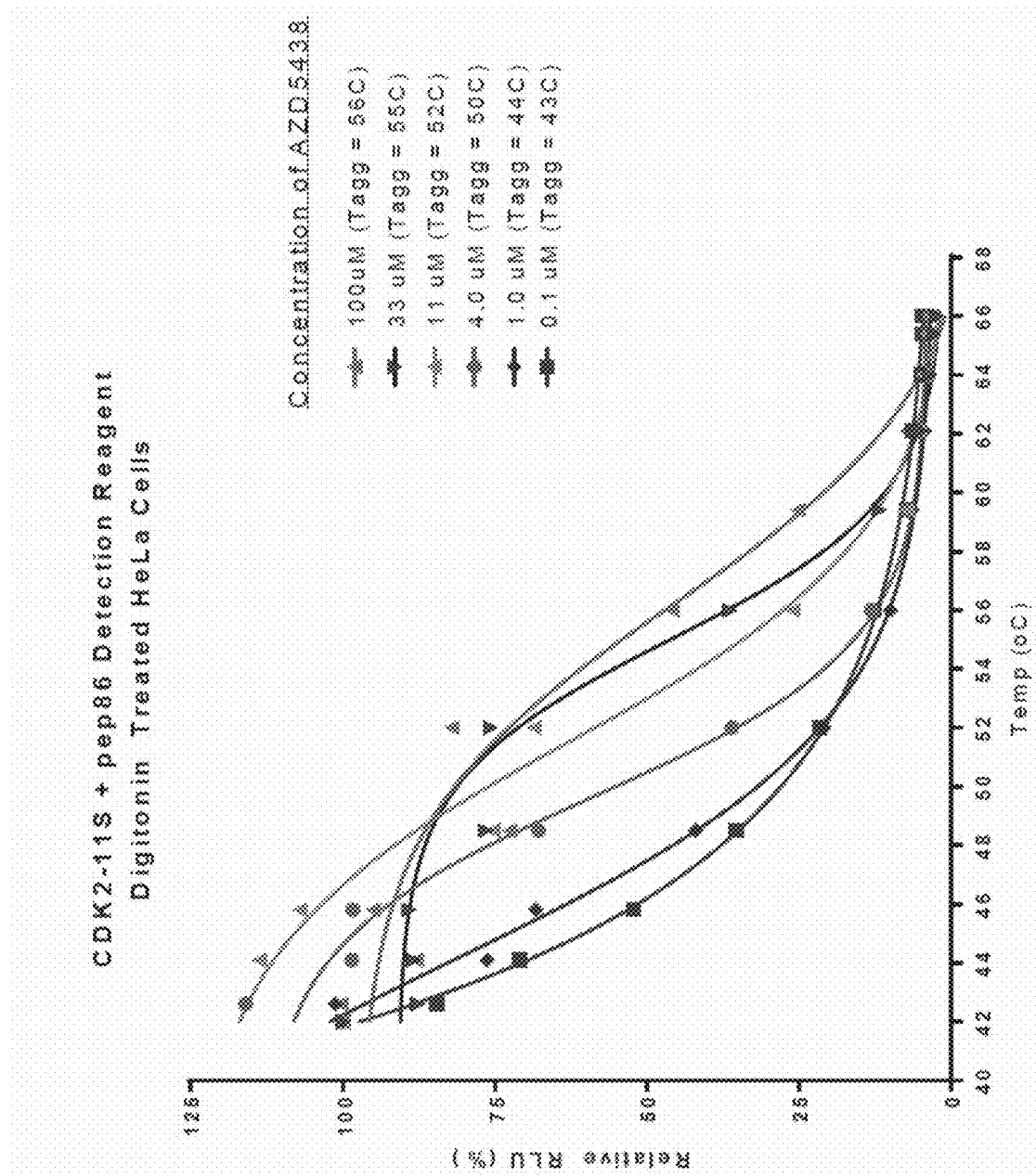

FIGS. 11 and 12 demonstrates the temperature and stabilizing ligand concentration dependency of the luciferase-based thermal shift assay which is consistent with other reported methods of thermal shift assay. Here, the $EC_{50}$ of the ligand AZD5438 shifts as a function of temperature and the apparent $T_{agg}$ shifts as a function of stabilizing ligand concentration. In this case, the targets consisted of CDK2-NLpep86 fusions (FIGS. 11A-C) and CDK2-NLpoly11S fusions (FIGS. 12A-B).

Example 12

BRET-Detection Thermal Shift Assay

Experiments were conducted during development of embodiments of the present invention to demonstrate detection of the stabilization of a target protein by the interaction with a target ligand via temperature dependent alteration of BRET signal generated by the energy transfer from a luciferase fused to the target protein to an environmentally sensitive dye that binds to all proteins unfolding in the sample including the target protein.

Protein thermal melting curves can be generated for purified proteins in which the extent of unfolding is measured by the gain in fluorescent signal from environmentally sensitive dyes that bind to the exposed hydrophobic surfaces of the protein as they unfold. Taking advantage of this property and adding these dyes to the luciferase-based thermal shift assay described herein, the environmentally-sensitive dye binds to the target protein-Nluc fusion, and BRET is produced upon addition of substrate when there is active Nluc available to excite the dye. The dye acts as a fluorescent BRET acceptor, and the transfer of energy is moderated by the proximity of the two partners. While the dye will bind to all proteins unfolding in the sample, the luciferase fusion gives the target protein specificity; hence any BRET signal is a direct readout on the state of the protein of interest.

HeLa cells were transfected with CDK2-Nluc or Nluc-LCK DNA at a 1:100 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of 2×10$^4$ cells/well in an 80 uL/well volume and treated with 10 uL/well of a 0.5 mg/ml solution of digitonin (Sigma) and 10 uL of 10% DMSO (Sigma) or 10 uL of a 1 mM stock solution of test compound in 10% DMSO. Test compounds included: Dasatinib (BioVision), AZD5438 (Selleckchem), Staurosporine (LC Laboratories), and Nilotinib (BioVision). The plates were then incubated for 1 hour in a humidified, 37° C./5% CO$_2$ incubator. The plates were placed into a thermal cycler (MW Research) where the samples were heated either individually at different temperatures spanning a gradient of 42-66° C. across the plate for 3 minutes to obtain apparent $T_{agg}$, or the samples are all heated for 3 minutes at one constant temperature to obtain ITDRC, followed by cooling at 22° C. for 3 minutes. The Protein Thermal Shift™ dye (Life Technologies) was added at a final concentration of 0.5× concentration (supplied as 1000×) in 1 uL/well volume. Furimazine Live Cell Substrate (Promega) was added to a final concentration of 1× in 20 uL/well volume, and a total volume of 100 uL/well was then transferred to a tissue culture plate (Corning). To measure BRET, filtered luminescence was measured on a BMG Clariostar luminometer equipped with 450 nm BP filter (donor) and 610 nm LP filter (acceptor), using 0.5 s integration time. MilliBRET units (mBU) were calculated by using the equation: (acceptor/donor)*1000. To obtain apparent $T_{agg}$ values, data was fitted using the bell shaped curve equation. To analyze ITDFC data, data was transformed and fitted to obtain apparent EC50s using the sigmoidal dose-response (variable slope) equation. All analyses were performed with Graphpad Prism software.

Figure 13:
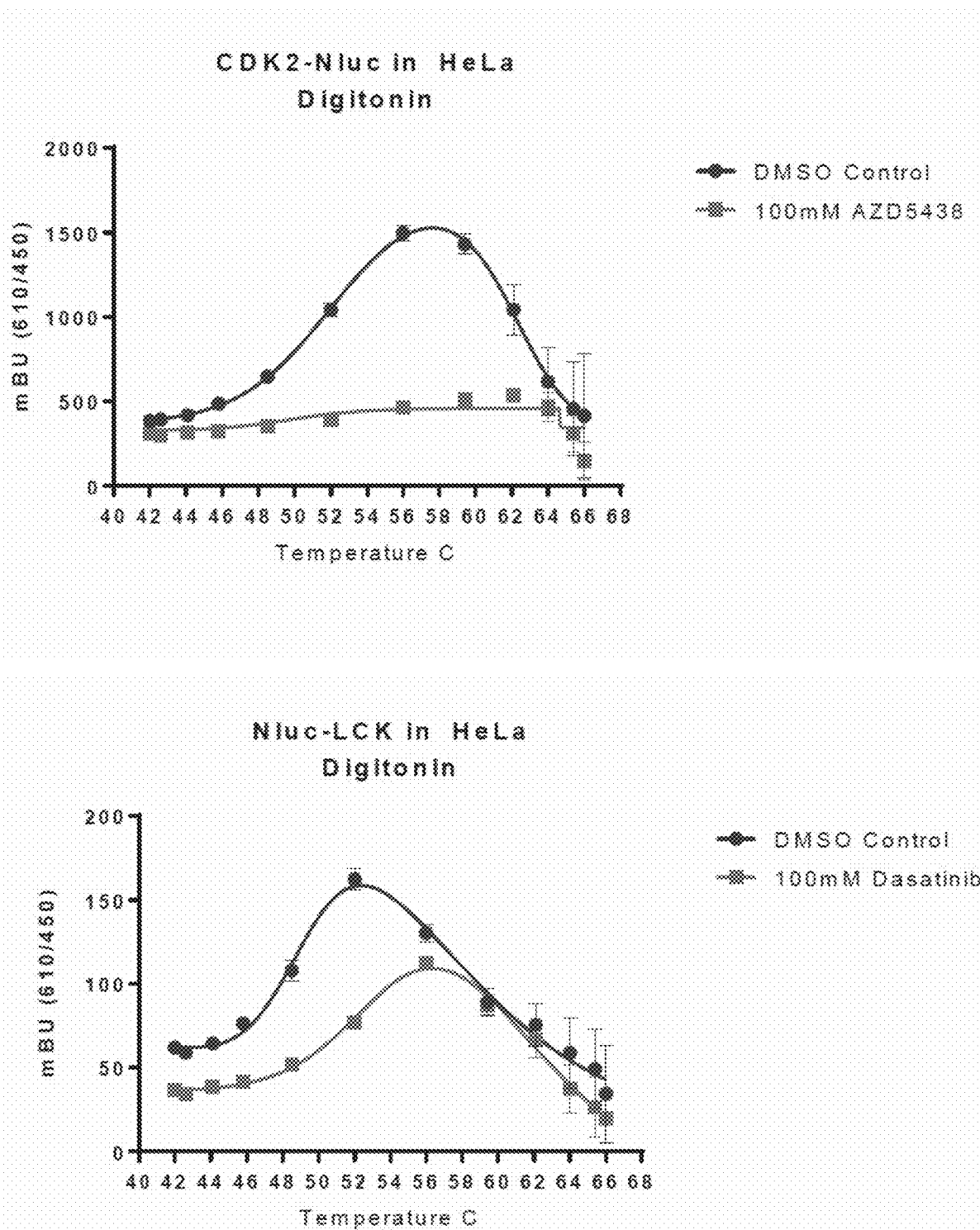
FIG. 13 shows detection of ligand binding through a change in melting temperature for CDK2-Nluc and LCK-Nluc as determined by bioluminescence resonance energy transfer (BRET) after incubation in the presence of stabilizing ligand in digitonin-treated mammalian cells subsequently exposed to a temperature gradient.

FIG. 13 demonstrates that BRET can be used to detect ligand binding through a change in melting temperature curves compared to DMSO controls as exampled with CDK2-Nluc (+/−AZD5438) and LCK-Nluc (+/−Dasatinib) target fusions. As expected, the shape of the BRET curves are bell shaped due to loss of Nluc signal with protein unfolding and increasing temperatures or dye dissociation upon protein aggregation or both.

In FIGS. 14A-B, to obtain isothermal dose response curves (ITDRC) in order to obtain compound rank order affinity and apparent EC50s, the curves generated when the samples were subjected to the temperature gradient to ensure compliance with the model were inspected first, apparent $T_{agg}$ calculated, and an appropriate temperature chosen for follow-up ITDRC or screening experiments. This was a temperature at which a majority of the protein is unfolded or precipitated in the absence of stabilizing compound, but at which a majority of the protein remains soluble in the presence of a saturating concentration of known stabilizing compound. To demonstrate this, ITDRC for a panel of kinase inhibitors with known different selectivity was established and tested for target engagement with CDK2-Nluc and LCK-Nluc fusions as determined by BRET after incubation in the presence of different concentrations of the individual compounds while time of heating and temperature were kept constant. This demonstrates the concentration dependence of the thermal stabilization and allows for compound affinity signatures to be obtained.

Example 13

BRET-Detection Thermal Shift Assay

Experiments were conducted during development of embodiments of the present invention to demonstrate detection of the stabilization of a target protein by the interaction with a target ligand via temperature dependent alteration of BRET signal generated by the energy transfer from a luciferase fused to the target protein to an environmentally sensitive dye that binds to all proteins unfolding in the sample including the target protein.

To demonstrate analysis of compound selectivity using the BRET method of thermal shift, a panel of compounds with known selectivity against CDK2, MAPK14, and HDAC1 was tested. It was found that the assay accurately detected the positive and negative ligands against these targets.

HeLa cells were transfected with CDK2-Nluc, Nluc-MAPK14, or HDAC1-Nluc DNA at a 1:100 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of 2×10$^4$ cells/well in an 90 uL/well volume and treated with 10 uL of 10% DMSO (Sigma) or 10 uL of a 1 mM stock solution of test compound in 10% DMSO. Test compounds included: Dasatinib (BioVision), AZD5438 (Selleckchem), Staurosporine (LC Laboratories), Nilotinib (BioVision), Ponatinib (SYNKinase), AMG548 (TOCRIS), SB203580(Adipogen), SAHA (TOCRIS), Mocetinostat (Selleckchem), Panibinostat (LC Laboratories), and ACY1215 (Selleckchem). The plates were then incubated for ½ hour in a humidified, 37° C./5% CO$_2$ incubator. Immediately prior to heating, 10 uL/well of a 0.5 mg/ml solution of digitonin (Sigma), Protein Thermal Shift™ dye (Life Technologies) was added at a final concentration of 0.5× concentration (supplied as 1000×) in 1 uL/well volume, and Furimazine Live Cell Substrate (Promega) was added to a final concentration of 1× in 20 uL/well volume. Plates were placed into a thermal cycler (MW Research) where the samples were heated individually at different temperatures spanning a gradient of 42-66° C. across the plate for 3 minutes followed by cooling at 22° C. for 3 minutes, and a total volume of 100 uL/well was then transferred to a tissue culture plate (Corning). To measure BRET, filtered luminescence was measured on a BMG Clariostar luminometer equipped with 450 nm BP filter (donor) and 610 nm LP filter (acceptor), using 0.5 s integration time. MilliBRET units (mBU) were calculated by using the equation: (acceptor/donor)*1000. Data was analyzed up to 62° C., and the data fitted to obtain apparent melting temperature where the protein is precipitating ($T_{agg}$ values) using the Boltzmann Sigmoidal equation with Graphpad Prism software.

Figure 15B:
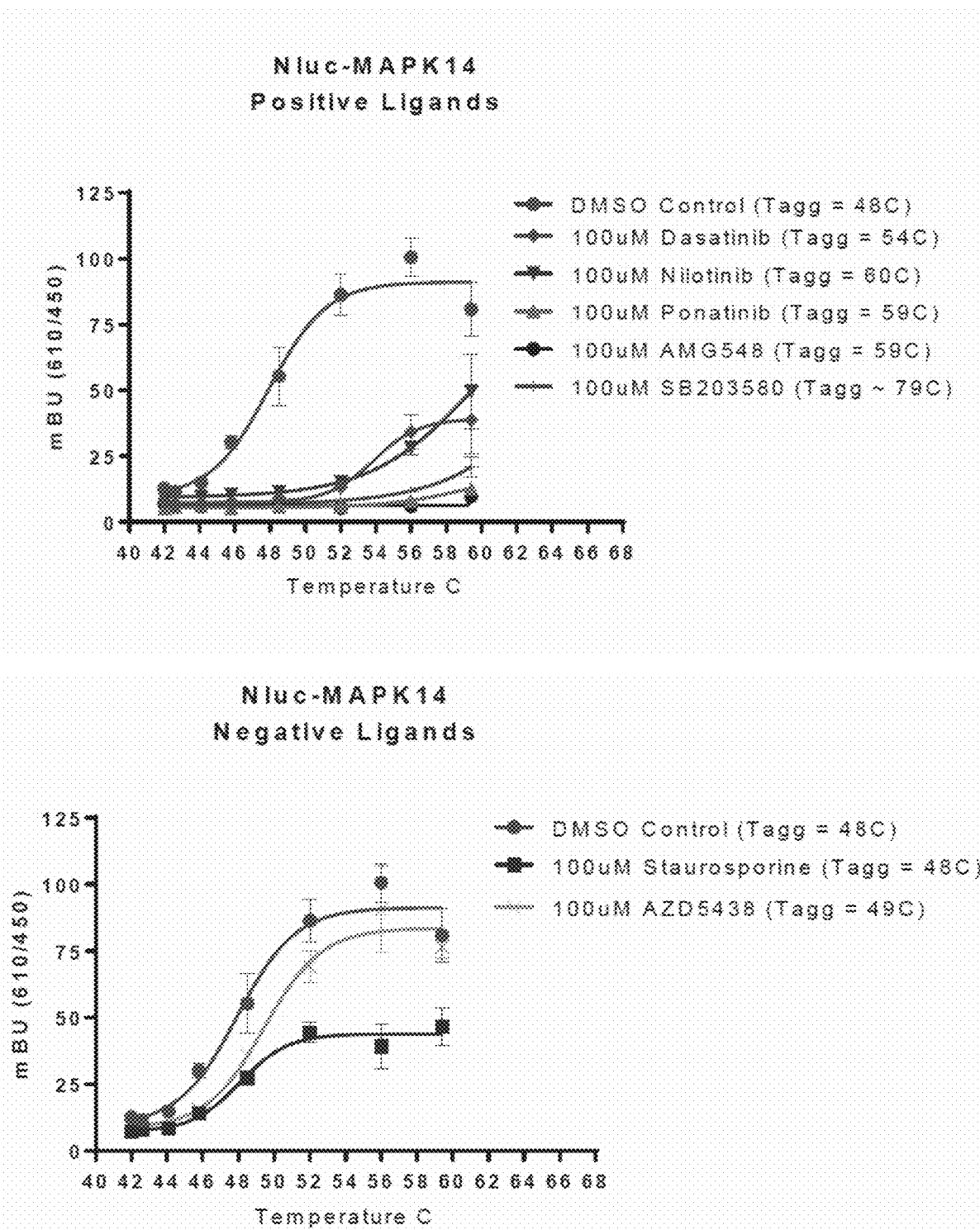
Figure 16:
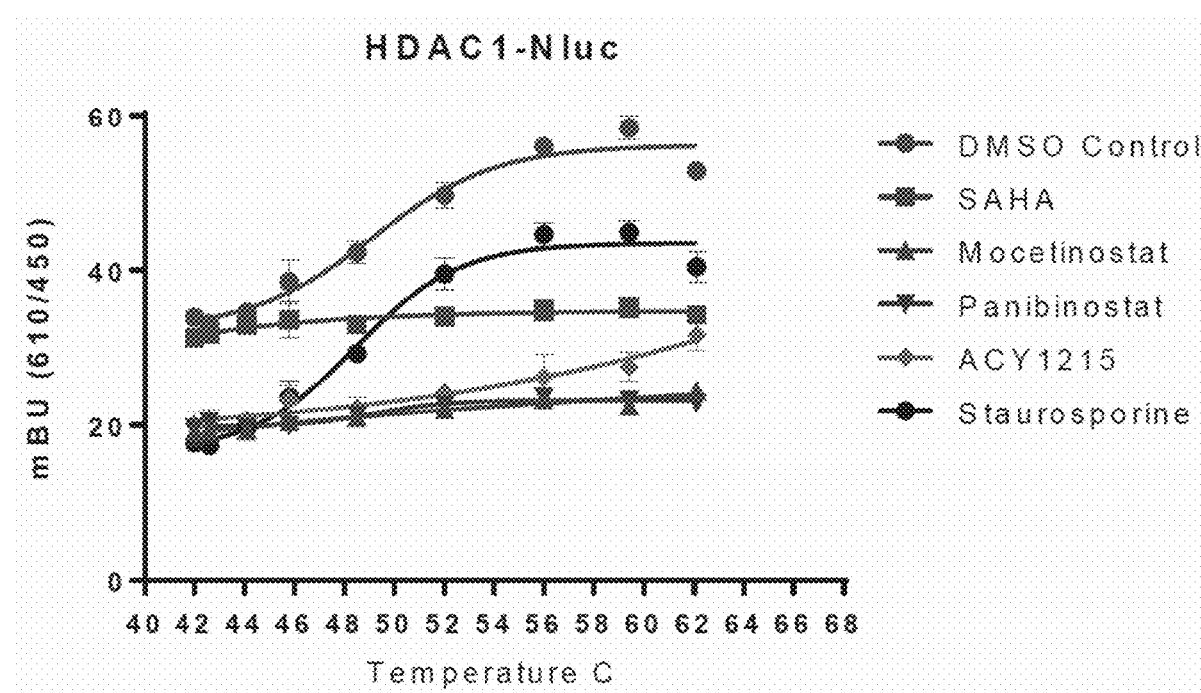
FIG. 16 shows detection of an increase in melting temperatures (stabilizing ligand) or no change in melting temperatures (non-binding) for the nuclear target fusion HDAC1-Nluc as determined by BRET after incubation with a panel of compounds in mammalian cells subsequently exposed to digitonin and a temperature gradient.

FIG. 15 shows detection of an increase in melting temperatures (stabilizing ligand) or no change in melting temperatures (non-binding) for cytoplasmic target fusions CDK2-Nluc and Nluc-MAPK14 as determined by BRET after incubation with a panel of compounds, thus displaying compound selectivity in mammalian cells subsequently exposed to digitonin and a temperature gradient. FIGS. 16A-F show detection of an increase in melting temperatures (stabilizing ligand) or no change in melting temperatures (non-binding) for the nuclear target fusion HDAC1-Nluc as determined by BRET after incubation with a panel of compounds in mammalian cells subsequently exposed to digitonin and a temperature gradient.

Example 14

BRET-Detection Thermal Shift Assay

Experiments were conducted during development of embodiments of the present invention to demonstrate detection of the stabilization of a target protein by the interaction with a target ligand via temperature dependent alteration of BRET signal generated by the energy transfer from a luciferase fused to the target protein to an environmentally sensitive dye that binds to all proteins unfolding in the sample including the target protein.

To demonstrate that many dyes are suitable for the luciferase-based thermal shift assay analyzed by BRET described herein, several different dyes were tested. Dye examples included: Protein Thermal Shift™ Dye, SYPRO Orange protein gel stain, and SYPRO Red protein gel stain.

HeLa cells were transfected with CDK2-Nluc at a 1:100 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of 2×10$^4$ cells/well in an 90 uL/well volume and treated with 10 uL of 10% DMSO (Sigma) or 10 uL of a 1 mM stock solution of Staurosporine (LC Laboratories) in 10% DMSO. The plates were then incubated for ½ hour in a humidified, 37° C./5% $CO_2$ incubator. Immediately prior to heating, 10 uL/well of a 0.5 mg/ml solution of digitonin (Sigma), Furimazine Live Cell Substrate (Promega) to a final concentration of 1× in 20 uL/well volume, and 1 ul of each dye dilution was added. Dyes included the SYPRO Orange, SYPRO Red, and PROTEIN THERMAL SHIFT Dye (all from Life Tech). Plates were placed into a thermal cycler (MW Research) where the samples were heated individually at different temperatures spanning a gradient of 42-66° C. across the plate for 3 minutes followed by cooling at 22° C. for 3 minutes, and a total volume of 100 uL/well was then transferred to a tissue culture plate (Corning). To measure BRET, filtered luminescence was measured on a BMG Clariostar luminometer equipped with 450 nm BP filter (donor) and 610 nm LP filter (acceptor), using 0.5 s integration time. MilliBRET units (mBU) were calculated by using the equation: (acceptor/donor)*1000. Data was then fitted to obtain apparent melting temperature where the protein is precipitating ($T_{agg}$ values) using the Boltzmann Sigmoidal equation with Graphpad Prism software.

Figure 17A:
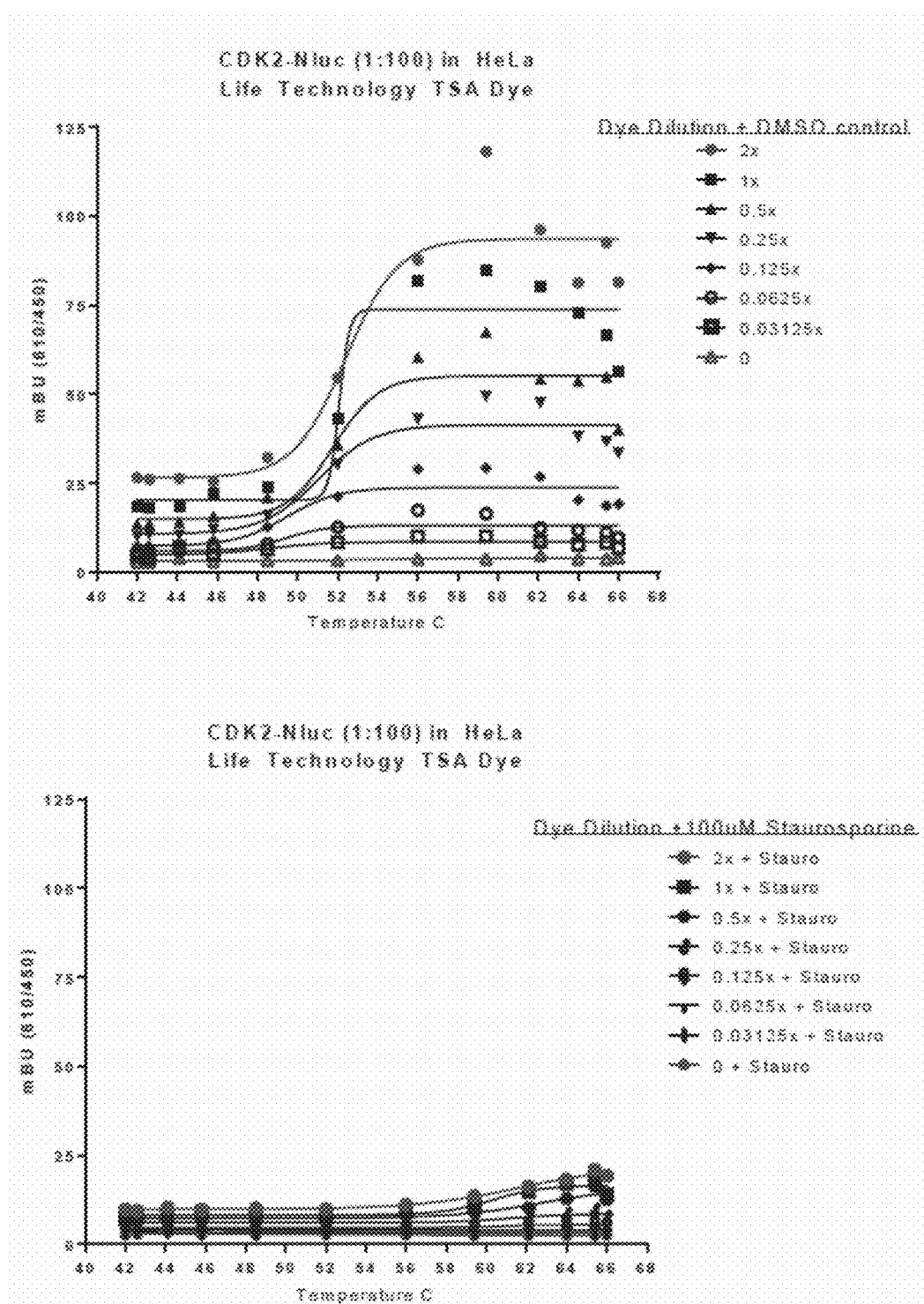
Figure 17C:
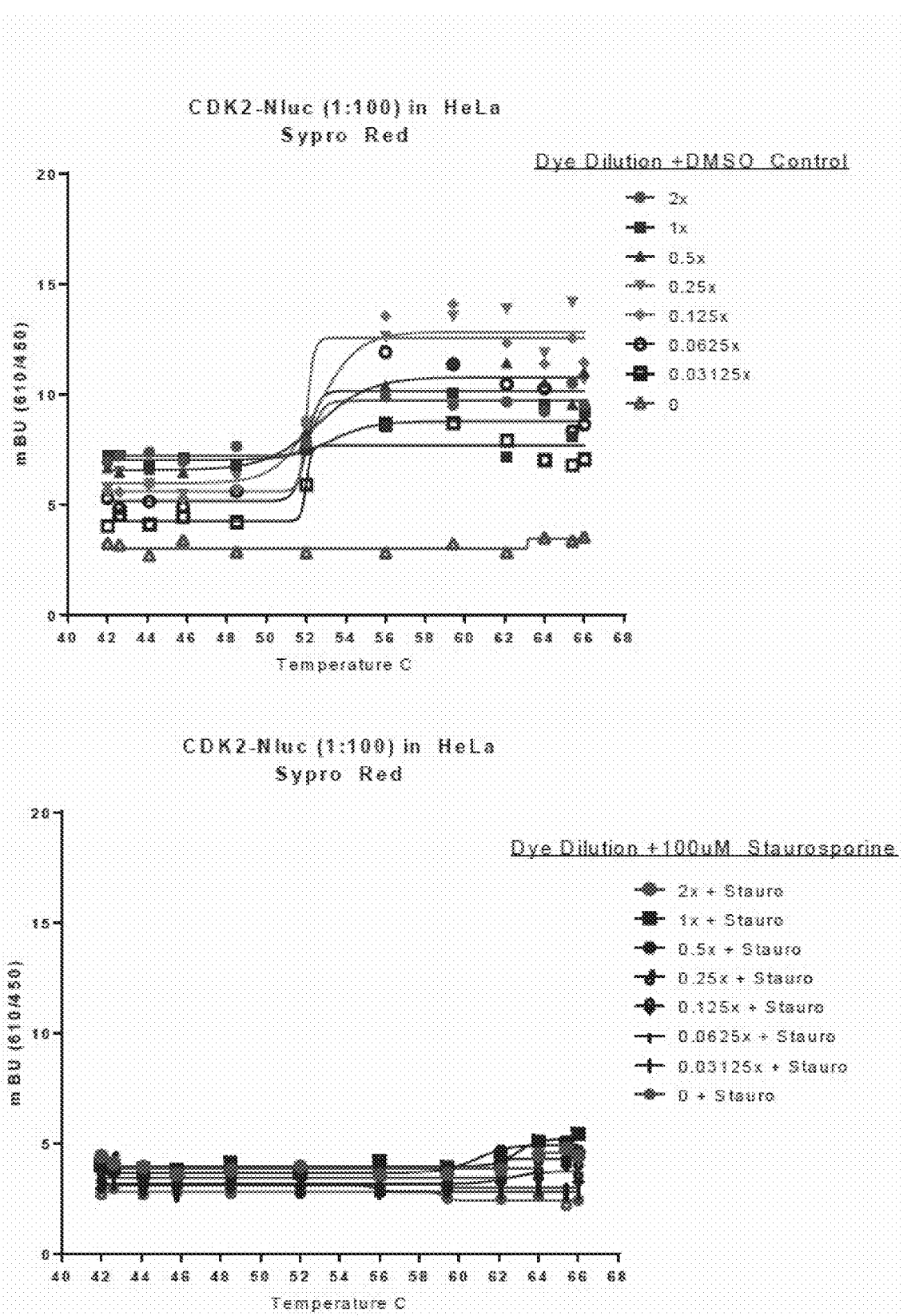

FIGS. 17A-B show detection of an increase in melting temperature for CDK2-Nluc as determined by BRET after incubation with stabilizing ligand (staurosporine) in mammalian cells subsequently exposed to digitonin and a temperature gradient using three different environmentally sensitive acceptor dyes reporting on protein folding status as BRET acceptor dyes. $B_{max}$ is acceptor dye dose dependent, but that there is no change in the apparent melting temperature ($T_{agg}$).

Example 15

BRET-Detection Thermal Shift Assay

Experiments were conducted during development of embodiments of the present invention to demonstrate detection of the stabilization of a target protein by the interaction with a target ligand via temperature dependent alteration of BRET signal generated by the energy transfer from a luciferase fused to the target protein to an environmentally sensitive dye that binds to all proteins unfolding in the sample including the target protein.

Figure 18A:
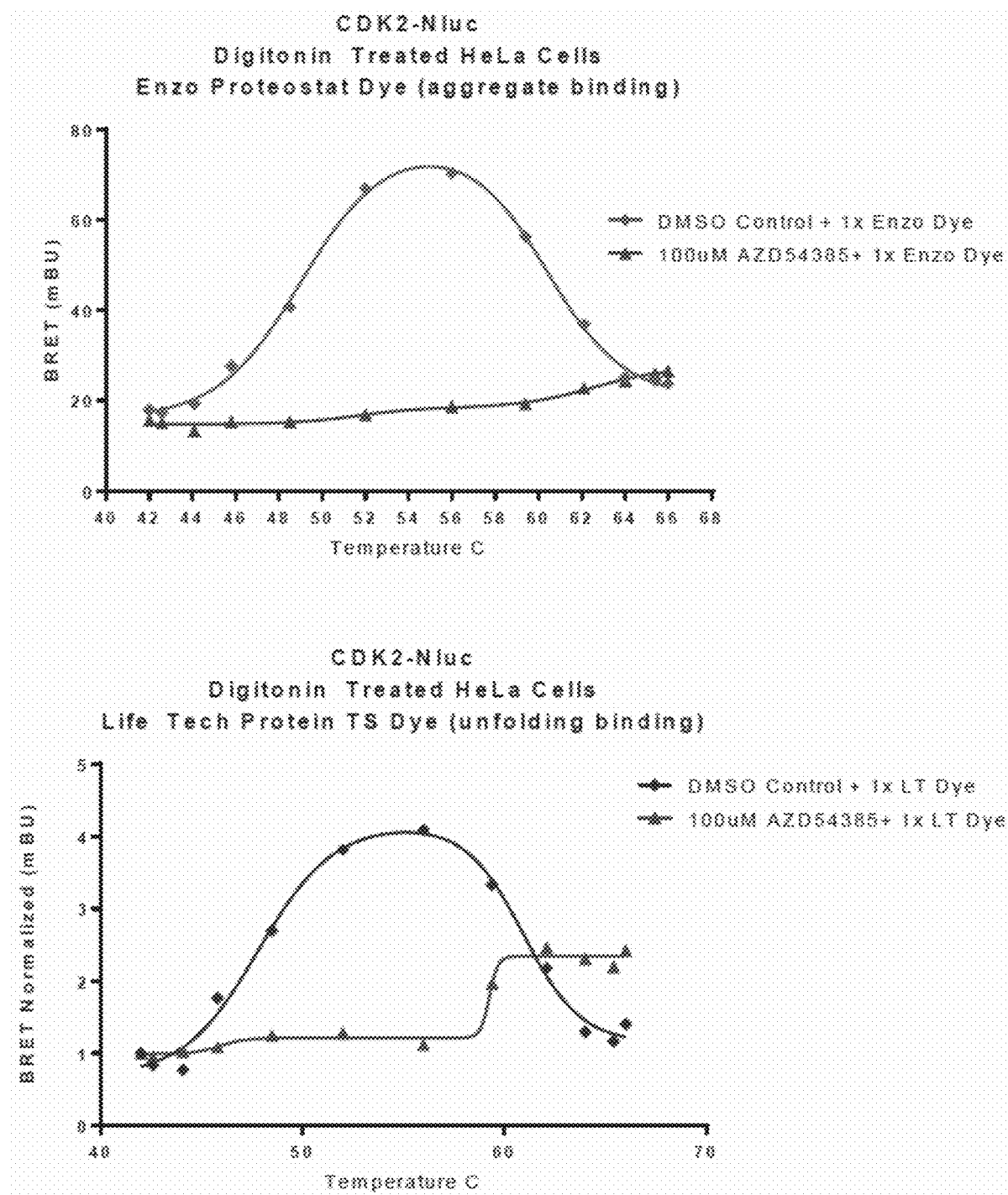
FIGS. 18A-18B show detection of an increase in melting temperature for CDK2-Nluc as determined by BRET after incubation with stabilizing ligand (AZD5438) in digitonin-treated mammalian cells subsequently exposed to a temperature gradient and using two different environmentally-sensitive dyes to report on the folded protein status and serve as BRET acceptor dyes which was either added before or after the heating step. Dye examples included: the dye included in the Life Technologies Thermal Shift Assay Dye Kit and the dye included in the Enzo PROTEOSTAT Thermal Shift Assay Kit.
Figure 18B:
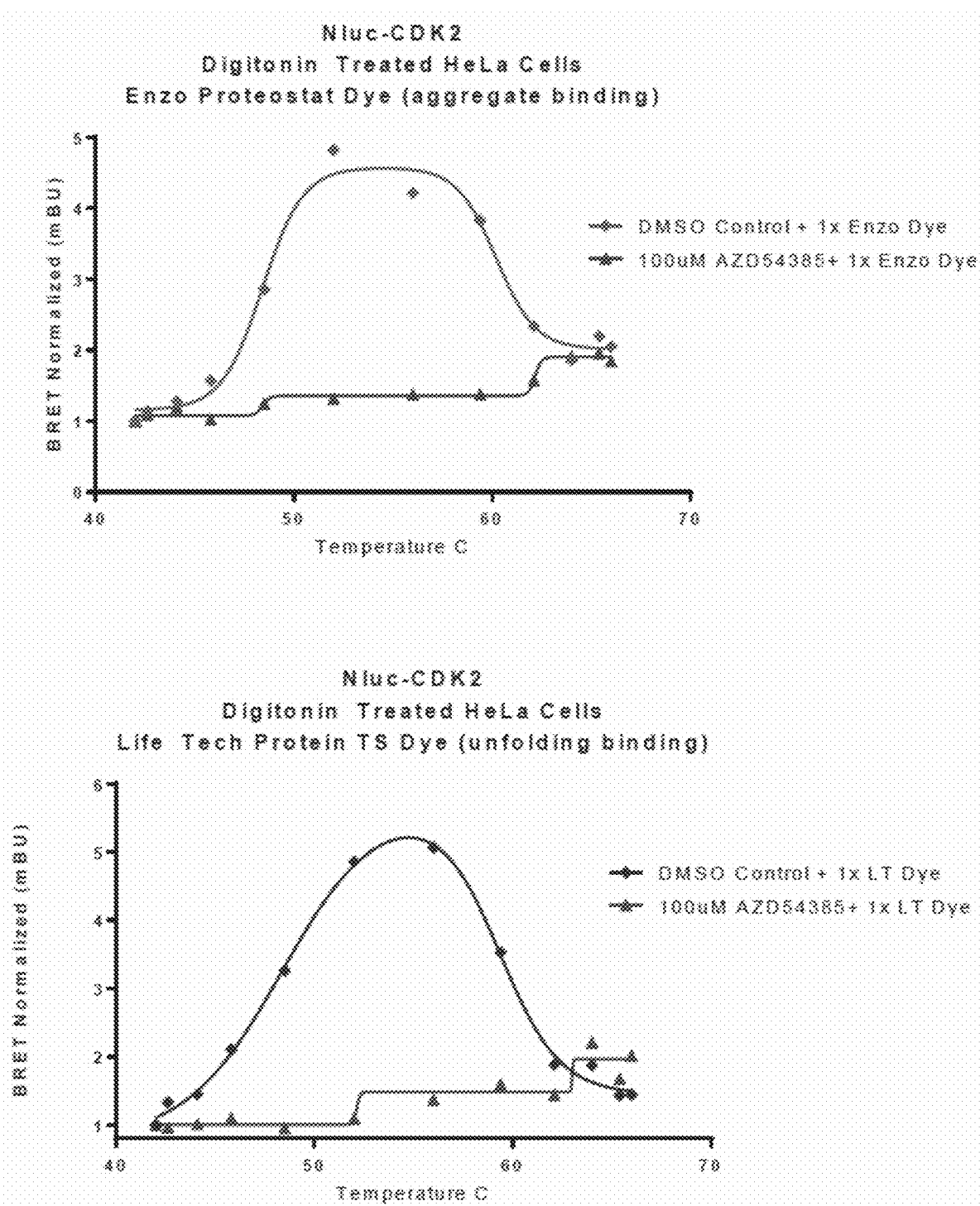

To demonstrate that the acceptor dye can be added either before or after the heating step in the luciferase-based thermal shift assay using BRET analysis, two different environmentally sensitive dyes were used to determine folded protein status and serve as BRET acceptor dyes. The dyes included in the Protein Thermal Shift™ Dye (Life Technologies) and the PROTEOSTAT dye (Enzo), which have differing properties in regards to protein status binding. The PROTEOSTAT dye binds to protein aggregates rather than unfolding proteins, whereas the Protein Thermal Shift™ dye binds to proteins as they unfold, but dissociates as the proteins aggregate. (FIG. 18).

HeLa cells were transfected with CDK2-Nluc DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of 2×10$^4$ cells/well in a 90 uL/well volume and treated with 10 uL/well of a 0.5 mg/ml solution of digitonin (Sigma) in 10% DMSO (Sigma) and 1 uL of 100% DMSO (Sigma) or 1 uL of a 10 mM stock solution of Staurosporine (LC Laboratories) in 100% DMSO. The plates were then incubated for 2 hour in a humidified, 37° C./5% $CO_2$ incubator. The plates were placed into a thermal cycler (MW Research) where the samples were heated either individually at different temperatures spanning a gradient of 42-66° C. across the plate for 3 minutes followed by cooling at 22° C. for 3 minutes. The Protein Thermal Shift™ Dye (Life Technologies) and the PROTEOSTAT dye (Enzo) were added at a final concentration of 1× (supplied as 1000×) in 1 uL/well volume either before or after the heating step. 90 ul/well was transferred to a tissue culture plate (Corning), and Furimazine Live Cell Substrate (Promega) was added to a final concentration of 1× in 20 uL/well volume. To measure BRET, filtered luminescence was measured on a BMG Clariostar luminometer equipped with 450 nm BP filter (donor) and 610 nm LP filter (acceptor), using 0.5 s integration time. MilliBRET units (mBU) were calculated by using the equation: (acceptor/donor)*1000. Data was fitted using the bell shaped curve equation with Graphpad Prism software. (FIG. 18)

Example 16

BRET-Detection Thermal Shift Assay

Experiments were conducted during development of embodiments of the present invention to demonstrate detection of the stabilization of a target protein by the interaction with a target ligand via temperature dependent alteration of BRET signal generated by the energy transfer from a luciferase fused to the target protein to an environmentally sensitive dye that binds to all proteins unfolding in the sample including the target protein.

HeLa cells were transfected with CDK2-Nluc or HDAC1-Nluc at a 1:100 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega) which had been reconstituted in DMSO (Sigma). The cells were seeded into 96-well tall-chimney PCR plate (Fisherbrand) at a density of $2 \times 10^4$ cells/well in an 80 uL/well volume and treated with 10 uL of 10% DMSO or 10 uL of a 1 mM stock solution of AZD5438 (for CDK2-Nluc) or Mocetinostat (for HDAC1-Nluc) in 10% DMSO. The plates were then incubated for ½ hour in a humidified, 37° C./5% $CO_2$ incubator. Immediately prior to heating, 10 uL/well of a 0.5 mg/ml solution of digitonin (Sigma), Furimazine Live Cell Substrate (Promega) to a final concentration of 1× in 20 uL/well volume, and 1 ul of the Protein Thermal Shift™ Dye (Life Technologies) for a final concentration of 0.5× was added. Plates were placed into a thermal cycler (MW Research) where the samples were heated individually at different temperatures spanning a gradient of 42-66° C. across the plate for 3 minutes. Some plates were also then further cooled at 22° C. for 3 minutes. A total volume of 100 uL/well was then transferred to a tissue culture plate (Corning). To measure BRET, filtered luminescence was measured on a BMG Clariostar luminometer equipped with 450 nm BP filter (donor) and 610 nm LP filter (acceptor), using 0.5 s integration time. MilliBRET units (mBU) were calculated by using the equation: (acceptor/donor)*1000. Data was then fitted to obtain apparent melting temperature where the protein is precipitating ($T_{agg}$ values) using the Boltzmann Sigmoidal equation with Graphpad Prism software.

Figure 19:
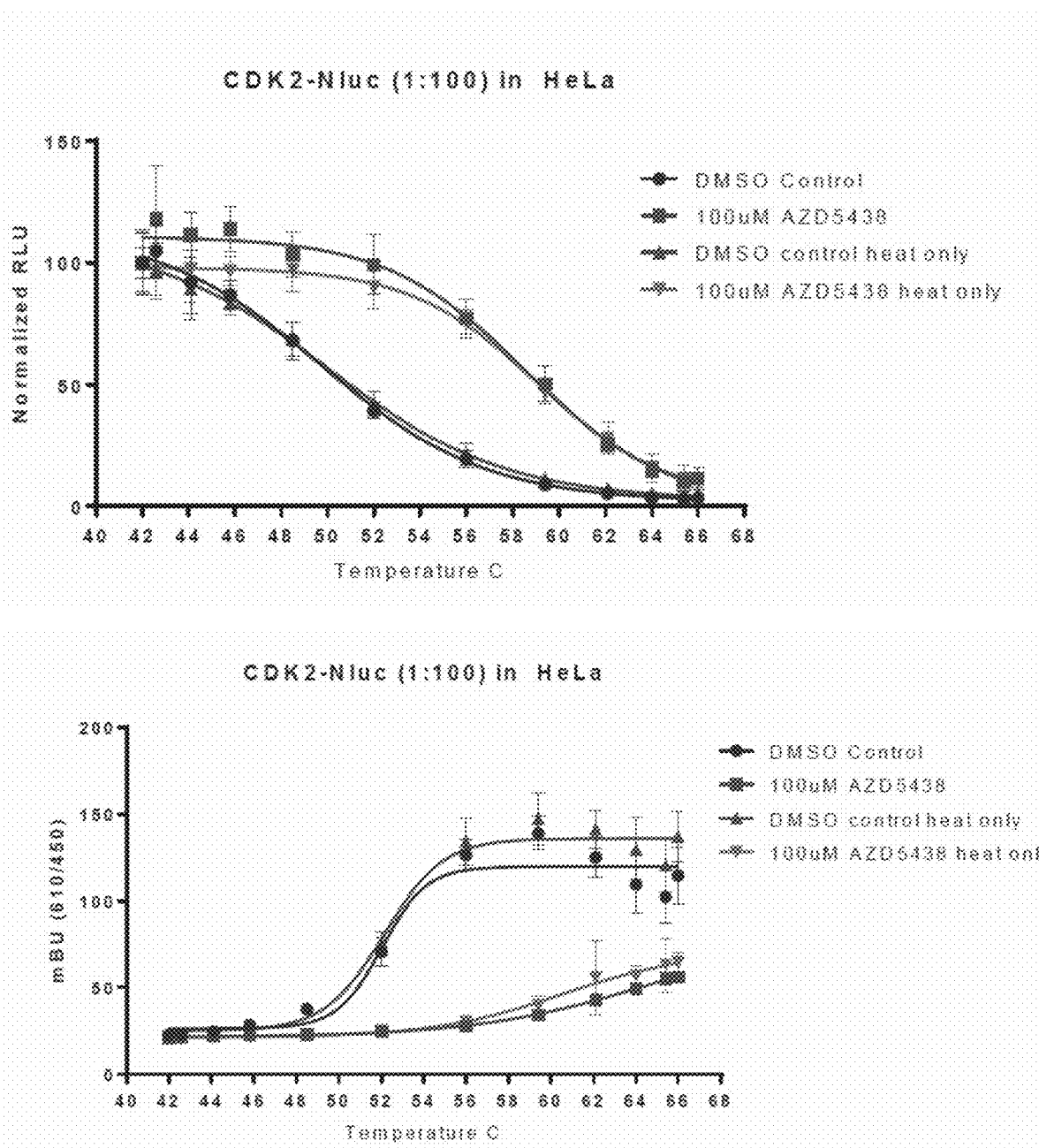
FIG. 19 shows detection of an increase in melting temperature for CDK2-Nluc as determined by NANOLUC activity (RLU) and BRET (mBU) after incubation with stabilizing ligand in mammalian cells subsequently exposed to a temperature gradient and either analyzed immediately or incubated at room temperature for 3 minutes prior to analysis.
Figure 23:
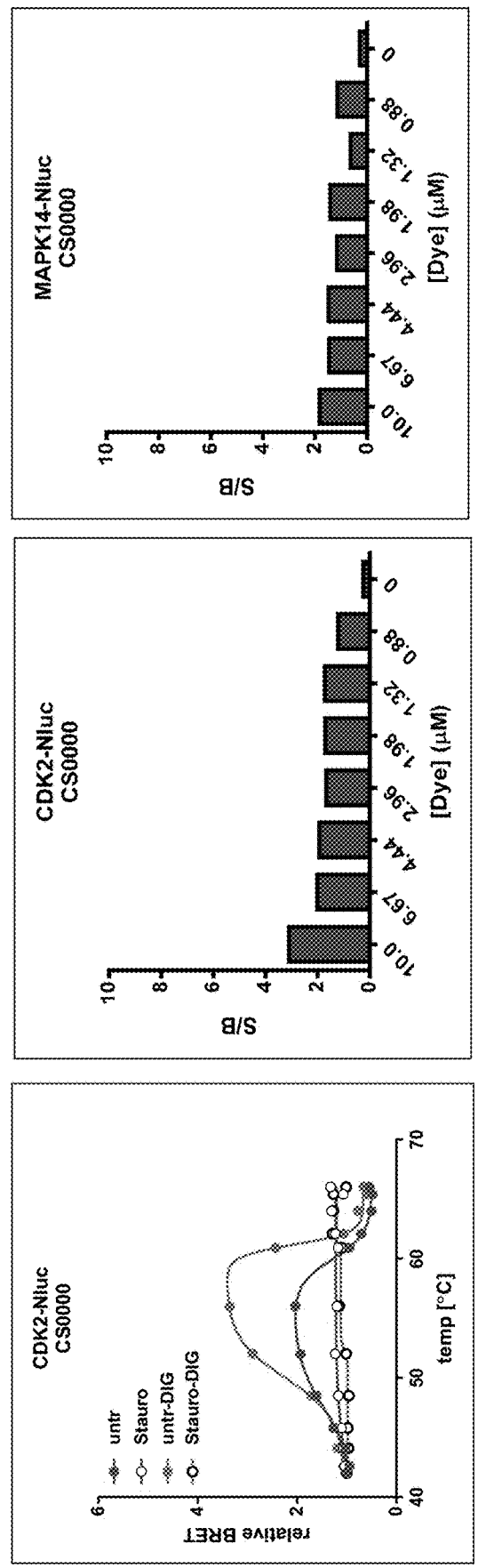

FIGS. 19 and 20A-B demonstrate data obtained when the assay was run with and without the cooling step that follows the 3 minutes heating gradient step using two different targets, CDK2-Nluc (FIG. 19) and HDAC1-Nluc (FIGS. 20A-B). A clear shift in apparent $T_{agg}$ was found whether a cooling step was included in the protocol or not as analyzed by both, direct luciferase readout and BRET.

Example 17

Other Proposed Proximity Based Reporter Methods for Detection of Ligand Binding in a Thermal Shift Assay Based on the successful use of a direct luciferase fusion or BRET to detect ligand-mediated thermal stabilization, other proximity-based reporter chemistries are understood to be useful. FIG. 21 gives schematic examples of other proximity based reporter methods that may be suitable for analysis of target engagement using thermal shift. For example, an epitope tag is attached to the protein of interest and following a thermal denaturation step, addition of a detection antibody labeled with a donor fluorophore (e.g., terbium, europium, etc.) is used in a FRET assay with an denaturation/aggregation-sensitive dye as a FRET acceptor. Ligand-mediated thermal stabilization results in a loss of FRET/TR-FRET signal. Another potential iteration is using a combination of labeled antibodies (e.g. donor-labeled anti-FLAG and acceptor labeled anti-V5) and a tandem epitope (e.g. FLAG-V5) tethered to the target protein are used as a detection system. When the target is stabilized by binding of a ligand, the epitope is presented and both antibodies bind, generating a proximity-based signal (e.g. FRET, TR-FRET). Upon thermal denaturation, the epitopes are unavailable to the antibody pair, resulting in a loss of proximity-based signal. Various detection chemistries can be applied for these prophetic examples (e.g. TR-FRET, proximity ligation, singlet oxygen transfer/alphascreen, etc.).

Example 18

Chemical Synthesis Description

A series of styryl dye derivatives were synthesized and screened in BRET detection thermal shift assay. The dye derivatives CS000, CS0004, CS0007, CS0008, CS0013, CS0010, CS0017, CS0018, CS0020, CS0024, CS0028, CS0038, CS0067, CS0068, CS0075, CS0081, CS0085, CS0086, CS0087, CS0096, and CS0155 and are generally synthesized analogously to CS0101 via a condensation reaction between various aryl aldehydes and pyridinium betaines or N-alkyl pyridinium, which has been described in literature (1$^{st}$ reaction in Scheme 1) (Hassner, A.; Birnbaum, D.; Loew, L. M. J. Org. Chem. 1984, 49, 2546-2551; herein incorporated by reference in its entirety). As depicted in Scheme 1, CS0101 was hydrolyzed under acidic condition to afford CS0036. The subsequent amide coupling and the acidic deprotection afforded CS0100 and CS0045 respectively. CS0048 was obtained via an amide coupling between CS0045 and 3-amino-1-propanesulfonic acid. CS0043 and CS0147 was synthesized analogously to CS0045. CS0073 was obtained via a N-alkylation reaction between CS0043 and neat 1,3 propane sultone (Scheme 2). CS0117 was synthesized via a Heck reaction between the para-bromo aniline 5 and para-vinyl pyridine 6 (Scheme 3).[1] N-alkylation of CS0117 afforded CS0121 (Scheme 3).[1] CS0112, CS0158, CS0071 and CS0072 were synthesized analogously to CS0121.

Scheme 1
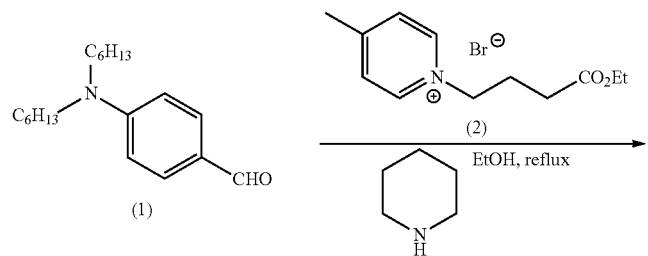
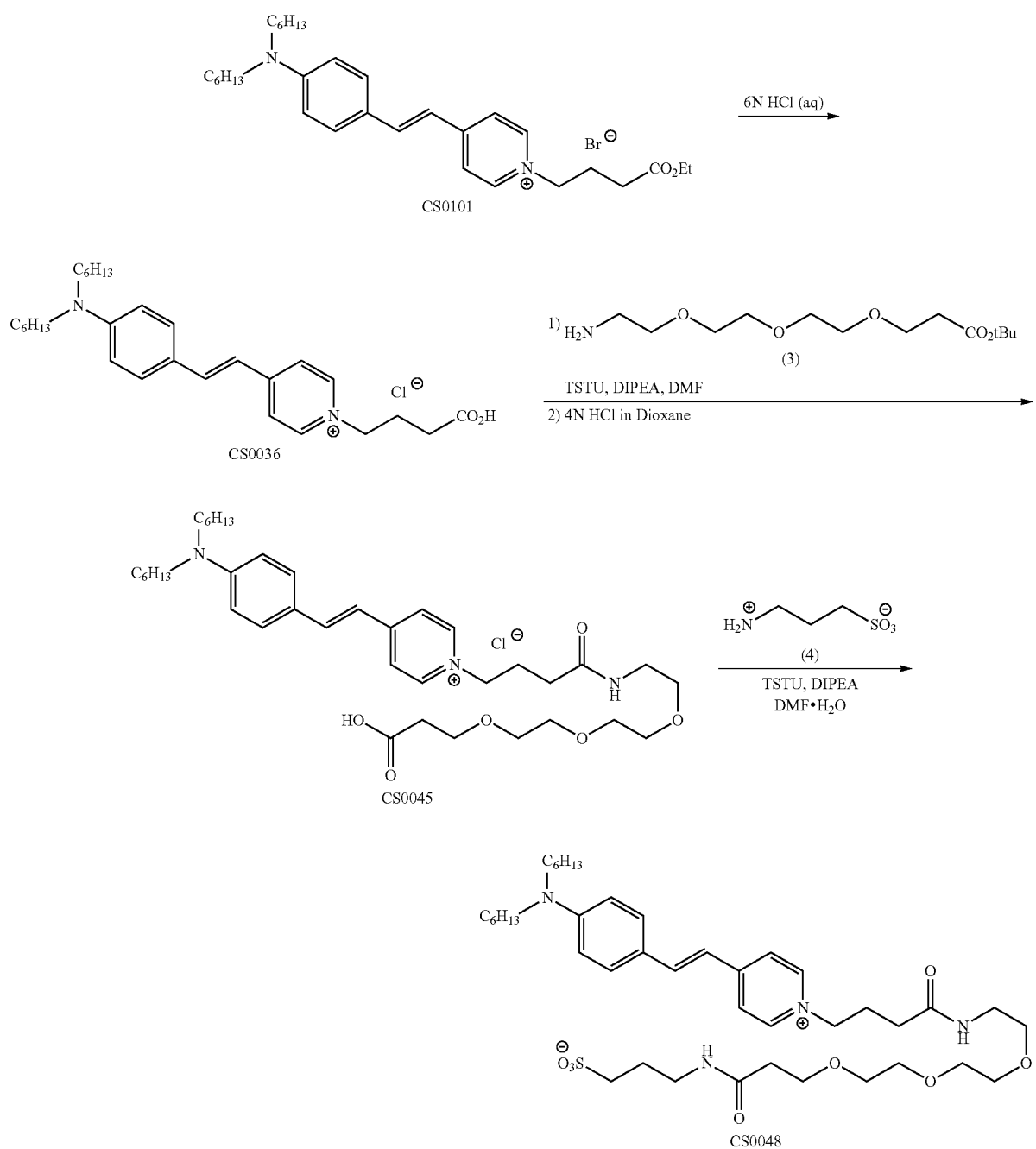

Scheme 2
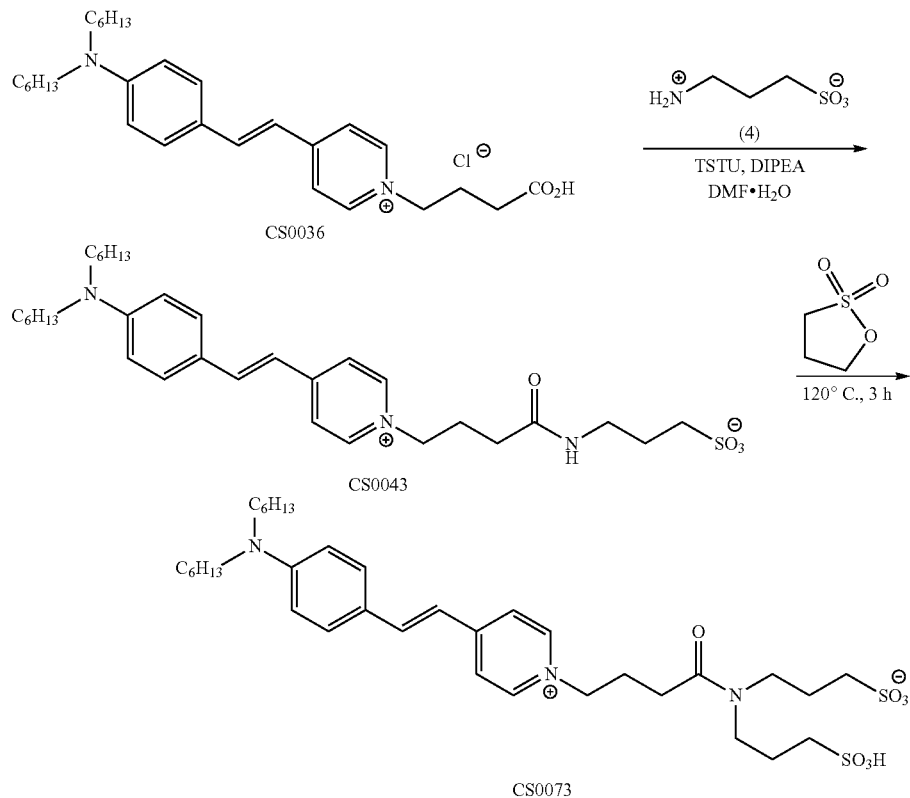
Scheme 3
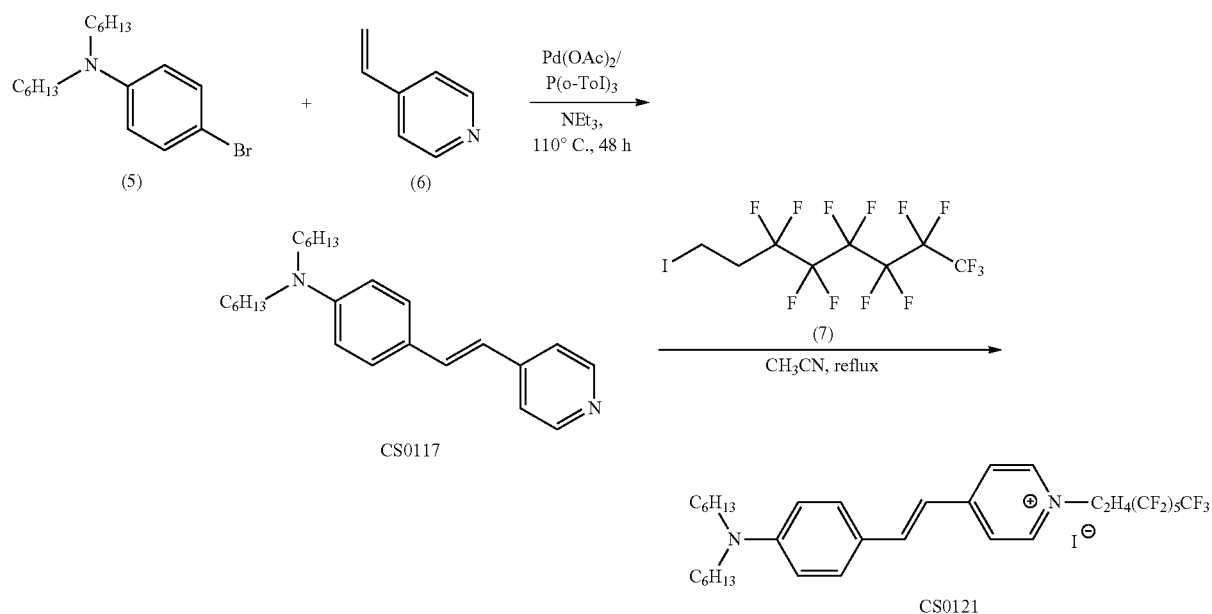
(E)-4-(4-(Dihexylamino)styryl)-1-(4-ethoxy-4-oxobutyl) pyridin-1-ium bromide (CS0101): To a solution of 4-(dihexylamino)benzaldehyde (1, 144 mg, 0.5 mmol, 1.0 equiv) in EtOH (4 mL) at RT, piperidine (4.3 mg, 0.05 mmol. 0.1 equiv) and 1-(4-ethoxy-4-oxobutyl)-4-methylpyridin-1-ium bromide (2, 144 mg, 0.5 mmol, 1.0 equiv) was added in one portion. The mixture was stirred at 90° C. for 15 h and cooled down at RT for 30 min. The desired product precipitated from the solution and was purified by silica gel chromatography ($CH_2Cl_2$/MeOH, 1/9). LRMS: observed for $[M-Br]^+$, 479.7.

(E)-1-(3-Carboxypropyl)-4-(4-(dihexylamino)styryl) pyridin-1-ium chloride (CS0036): To a solution of CS0101 (324 mg, 0.58 mmol, 1.0 equiv) in 1,4-dioxane (4 mL) at RT, 6 N HCl (aq, 4 mL, 24 mmol, 41 equiv) was added. The mixture was stirred at 100° C. for 15 h and concentrated in vacuo to afford the crude. The desired product was purified by silica gel chromatography ($CH_2Cl_2$/MeOH, 1/9). LRMS: observed for $[M-Cl]^+$, 451.7.

(E)-4-(4-(Dihexylamino)styryl)-1-(2,2-dimethyl-4,17-dioxo-3,7,10,13-tetraoxa-16-azaicosan-20-yl)pyridin-1-ium chloride (CS0100): To a solution of CS0036 (70 mg, 0.13 mmol, 1.0 equiv) in DMF (1.5 mL) at RT, TSTU (40 mg, 0.13 mmol, 1.0 equiv) and $NEt_3$ (60 µL, 0.43 mmol, 2.5 equiv) was added. The solution was stirred at RT for 1 h. To the reaction mixture, tert-butyl 3-(2-(2-(2-aminoethoxy)ethoxy)ethoxy)propanoate (3, 43.8 mg, 0.16 mmol, 1.2 equiv) in DMF (1.5 mL) was added. The reaction was stirred at RT for 15 h. LC-MS analysis indicated full conversion of the starting material. The solvent was removed in vacuo to afford the crude and the desired product was purified by silica gel chromatography ($CH_2Cl_2$/MeOH, 1/9). LRMS: observed for $[M-Cl]^+$, 711.1.

(E)-1-(1-Carboxy-13-oxo-3,6,9-trioxa-12-azahexadecan-16-yl)-4-(4-(dihexylamino)styryl)pyridin-1-ium chloride (CS0045): The starting material CS0100 (40 mg, 0.5 mmol, 1.0 equiv) was dissolved in 4N HCl in dioxane (2 mL, 8 mmol, 16 equiv). The mixture was stirred at 100° C. for 15 h and concentrated in vacuo to afford the crude. The desired product was purified by silica gel chromatography ($CH_2Cl_2$/MeOH, 1/9). LRMS: observed for $[M-Cl]^+$, 654.9.

(E)-21-(4-(4-(Dihexylamino)styryl)pyridin-1-ium-1-yl)-5,18-dioxo-8,11,14-trioxa-4,17-diazahenicos-ane-1-sulfonate (CS0048): To a solution of CS0045 (60 mg, 0.09 mmol, 1.0 equiv) in DMF (1.5 mL) at RT, TSTU (33 mg, 0.11 mmol, 1.2 equiv) and $NEt_3$ (51 µL, 0.37 mmol, 4 equiv) was added. The solution was stirred at RT for 1 h. To the reaction mixture, 3-amino-1-propanesulfonic acid (4, 19.1 mg, 0.14 mmol, 1.5 equiv) in $H_2O$ (1 mL) was added. The reaction was stirred at RT for 15 h. LC-MS analysis indicated full conversion of the starting material. The solvent was removed in vacuo to afford the crude and the desired product was purified by silica gel chromatography ($CH_2Cl_2$/MeOH, 1/9). LRMS: observed for $[M+H]^+$, 776.1.

(E)-3-(4-(4-(4-(Dihexylamino)styryl)pyridin-1-ium-1-yl)-N-(3-sulfopropyl)butanamido)propane-1-sulfonate (CS0073): CS0043 was mixed with 1,3 propane sultone (1 mL) and heated at 120° C. for 3 h. The mixture was cooled down to RT and resuspended in hot MeOH (20 mL), filtered over Celite. Concentration in vacuo afforded the crude, which was purified by silica gel chromatography ($CH_2Cl_2$/MeOH, 1/9). LRMS: observed for $[M+H]^+$, 695.1.

(E)-N,N-Dihexyl-4-(2-(pyridin-4-yl)vinyl)aniline (CS0117): To a flask charged with $Pd(OAc)_2$ (11.2 mg, 50 µL, 0.05 equiv) and tri-(o-tolyl) phosphine (45.6 mg, 0.14 mmol, 0.15 equiv), $NEt_3$ (5 mL) was added. The mixture was stirred under $N_2$ for 20 min. To the mixture, para-bromo aniline (5, 340 mg, 1 mmol, 1.0 equiv) and para-vinyl pyridine (6, 115.7 mg, 1.1 mmol, 1.1 equiv) was added. The mixture was heated up to 120° C. and stirred for 48 h under $N_2$. The reaction was cooled down and concentrated to afford the crude. The desired product was purified by silica gel chromatography (Heptane/EtOAc, 6/4). LRMS: observed for $[M+H]^+$, 365.6.

(E)-4-(4-(dihexylamino)styryl)-1-(3,3,4,4,5,5,6,6,7,7,8,8,8-tridecafluorooctyl)pyridin-1-iumiodide (CS0121): To a solution of CS0117 (70 mg, 0.19 mmol, 1.0 equiv) in $CH_3CN$ (3 mL), 1,1,1,2,2,3,3,4,4,5,5,6,6-tridecafluoro-8-iodooctane (7, 108 mg, 0.23 mmol, 1.2 equiv) was added. The reaction was heated to reflux for 15 h. LC-MS indicated full conversion to the desired product. The mixture was concentrated in vacuo and purified by silica gel chromatography ($CH_2Cl_2$/MeOH, 1/9). LRMS: observed for $[M-I]^+$, 711.8.

Example 19

BRET-Detection Thermal Shift Assay

Experiments were conducted during development of embodiments of the present invention to demonstrate detection of the stabilization of a target protein by the interaction with a target ligand via temperature dependent alteration of BRET signal generated by the energy transfer from a luciferase fused to the target protein to an environmentally sensitive dye that binds to all proteins unfolding in the sample including the target protein.

To demonstrate analysis of compound selectivity using the BRET method of thermal shift, a panel of compounds with known selectivity against CDK2 and MAPKI4 was tested. It was found that the assay accurately detected the positive and negative ligands against these targets.

HeLa cells were transfected with CDK2-Nluc or Nluc-MAPKI4 DNA at a 1:10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega), which had been reconstituted in DMSO (Sigma). The cells were seeded into wells of a 96-well, tall-chimney PCR plate (Fisherbrand) at a density of $2 \times 10^4$ cells/well in an 90 uL/well volume and treated with 10 uL of 10% DMSO (Sigma) or 10 uL of a 1 mM stock solution of the test compound Staurosporine (LC Laboratories) in 10% DMSO. The plates were then incubated for ½ hour in a humidified, 37° C./5% $CO_2$ incubator. Immediately prior to heating, 10 uL/well of a 0.5 mg/ml solution of digitonin (Sigma) and dye derivative was added at a final concentration of 10 uM or in a dose response as indicated in B and C of each figure in 1 uL/well volume. Plates were placed into a thermal cycler (MW Research) where the samples were heated individually at different temperatures spanning a gradient of 42-66° C. across the plate for 3 minutes followed by cooling at 22° C. for 3 minutes, and a total volume of 100 uL/well was then transferred to a tissue culture plate (Coming). Furimazine Live Cell Substrate (Promega) was added to a final concentration of 1× in 20 uL/well volume. To measure BRET, filtered luminescence was measured on a BMG Clariostar luminometer equipped with 450 nm BP filter (donor) and 610 nm LP filter (acceptor), using 0.5 s integration 5 time. MilliBRET units (mBU) were calculated by using the equation: (acceptor/donor)*1000.

Data was analyzed up to 62° C., and the data fitted to obtain apparent melting temperature where the protein is precipitating ($T_{agg}$ values) using the Boltzmann Sigmoidal equation with Graphpad Prism software.

FIGS. 23-34 demonstrate: (A) that BRET using dyes synthesized in Example 18 detects ligand binding through a change in relative BRET compared to DMSO controls; (B) the fold change in BRET signal at 56° C. over the background BRET signal at 42° C. for cells transfected with CDK2-Nluc target that were treated with DMSO and varying dye concentrations; and (C) the fold change in BRET signal at 52° C. over the background BRET signal at 42° C. for cells transfected with Nluc-MAPK14 target that were treated with DMSO and varying dye concentrations Example 20

Figure 35:
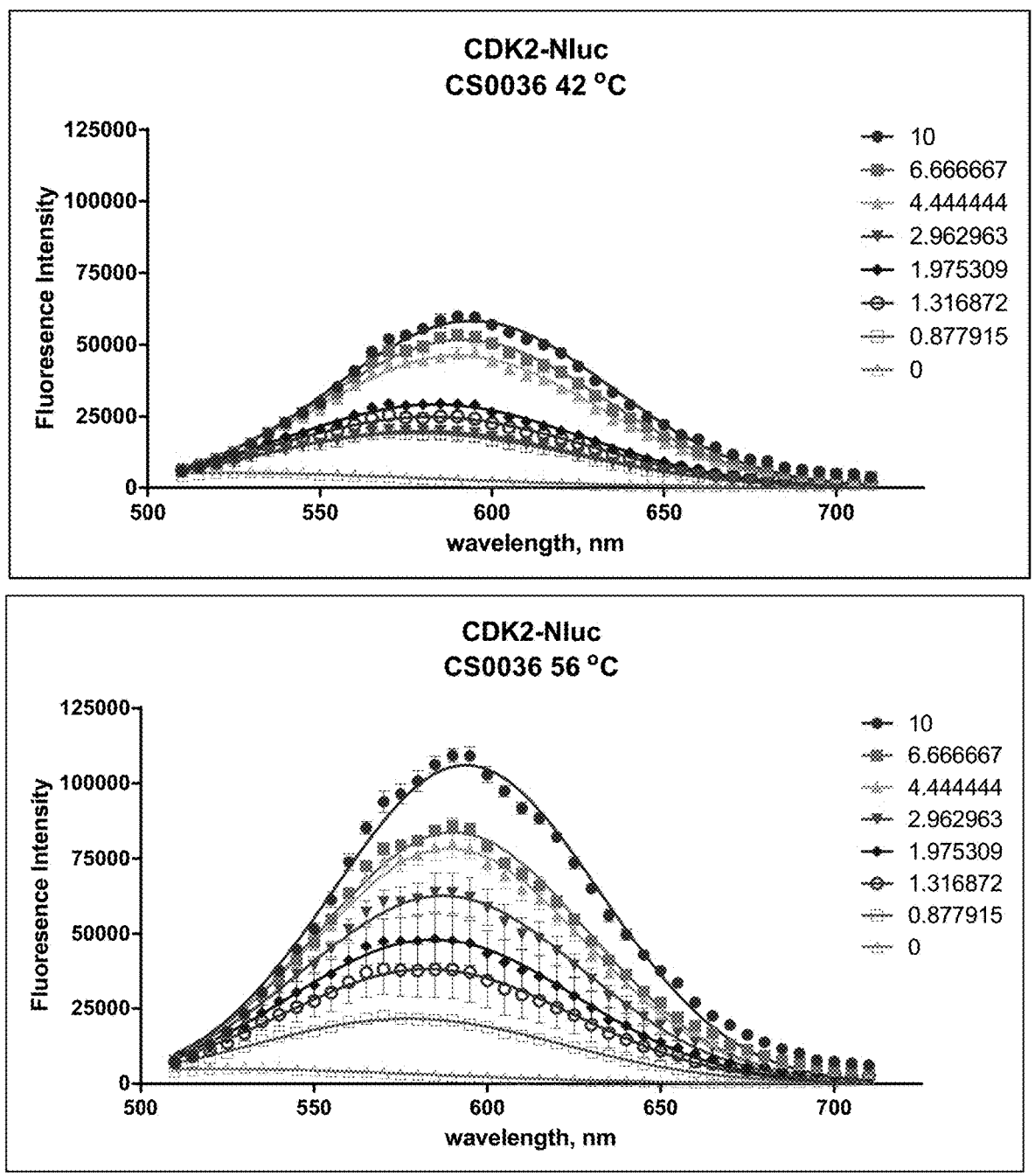
FIG. 35 shows fluorescent mode analysis of CS0036.
Figure 37:
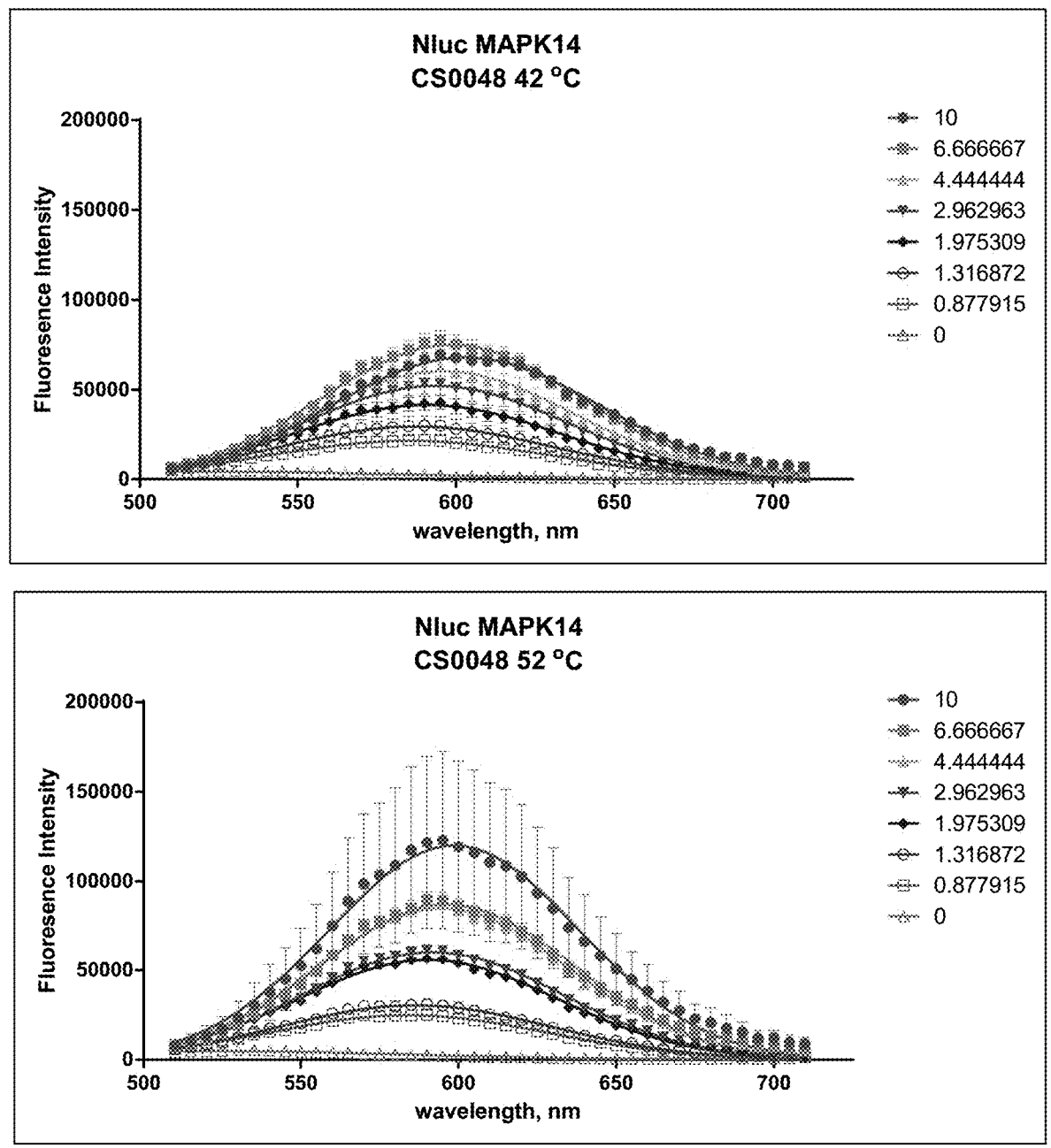
FIG. 37 shows fluorescent mode analysis of CS0048.

The properties of environmentally sensitive dyes for thermal shift assays include having a gain in fluorescence upon binding to proteins that are unfolding due to thermal insult. FIGS. 35-37 demonstrate the fluorescent spectra for some of the synthesized dyes (described in Example 18) when added to cells lysates that had been transfected with Nluc-target protein, and then either heated at 42° C. (baseline), 56° C. (for CDK2-Nluc target), or 52° C. (for Nluc-MAPK14 target). The higher temperature results in a gain in fluorescence thus showing the change in dye binding and fluorescent properties indicating that it is a useful dye for this application.

HeLa cells were transfected with CDK2-Nluc or Nluc-MAPKI4 DNA at a 1: 10 DNA ratio and incubated overnight. The cells were trypsinized using Trypsin-EDTA (0.25%) (Gibco) and re-suspended in Opti-MEM without phenol red (Gibco)+1× Protease Inhibitor Cocktail (Promega), which had been reconstituted in DMSO (Sigma). The cells were seeded into wells of a 96-well, tall-chimney PCR plate (Fisherbrand) at a density of 2×10$^4$ cells/well in an 90 uL/well volume and treated with 10 uL of 10× dye solution and heated at 42° C., 52° C., or 56° C. for 3 minutes followed by cooling at 25° C. for 2 minutes. Samples were transferred to a tissue culture plate and analyzed in fluorescent spectral mode on a Clariostar.

Example 21

Target Genome Editing

Targeted genome editing technologies to introduce reporter tags to a target protein of interest are used to evaluate ligand binding induced thermal stabilization at endogenous levels of protein expression in the relevant cellular context. Targeted genome editing technologies include, but are not limited to, clustered regularly-interspaced short palindromic repeats (CRISPR/Cas system), zinc finger nucleases (ZFN), transcription-activator-like effector-based nucleases (TALENs), and engineered meganucleases re-engineered homing endonucleases. Targeted protein fusions are made, in some embodiments, with a high affinity NLpoly, NLpoly, or NANOLUC luciferase to a protein of interest. These tags are fused to the N- or C-terminal of the protein of interest or internally within the target protein of interest. Assays are performed in both selected clonal cell lines as well as in unselected pools of cells. These assays are performed under live cell or lytic conditions. Assays in which the peptide reporters are used (high affinity NLpoly and NLpoly) require that the complementary peptide (i.e., NLpep) be present for reconstitution of active reporter luciferase and signal. In some embodiments, this is done lytically using a reagent that contains the complementary NLpep or through using mammalian cells that expresses the NLpep complementary to the NLpep used for the genomic editing of the target of interest.

Sequences

```
SEQ ID NO: 1 (wild-type OgLuc)-
mftladfvgdwqqtagynqdqvleqgglsslfqalgvsvtpiqkvvlsge nglkadihviipyeglsgfqmgliemifkvvypvddhhfkiilhygtlvi dgvtpnmidyfgrpypgiavfdgkqitvtgtlwngnkiyderlinpdgsl lfrvtingvtgwrlcenila SEQ ID NO: 2 (NANOLUC)-
mvftledfvgdwrqtagynldqvleqggvsslfqnlgvsvtpiqrivlsg englkidihviipyeglsgdqmgqiekifkvvypvddhhfkvilhygtlv idgvtpnmidyfgrpyegiavfdgkkitvtgtlwngnkiiderlinpdgs llfrvtingvtgwrlcerila SEQ ID NO: 3-
gvtgwrlcerila SEQ ID NO: 4-
mvftladfvgdwqqtagynqdqvleqgglsslfqalgvsvtpiqkvvlsg englkadihviipyeglsgfqmgliemifkvvypvddhhfkiilhygtlv idgvtpnmidyfgrpypgiavfdgkqitvtgtlwngnkiyderlinpdgs llfrvtin SEQ ID NO: 5 (NLpep86)-
vsgwrlfkkis SEQ ID NO: 6 (NLpoly11S)-
mvftledfvgdweqtaaynldqvleqggvssllqnlavsvtpiqrivrsg enalkidihviipyeglsadqmaqieevfkvvypvddhhfkvilpygtlv idgvtpnmlnyfgrpyegiavfdgkkitvtgtlwngnkiiderlitpdgs mlfrvtins SEQ ID NO: 7 (NLpoly156)-
mvftledfvgdwrqtagynldqvleqggvsslfqnlgvsvtpiqrivlsg enalkidihviipyeglsgdqmgqiekifkvvypvddhhfkvilhygtlv idgvtpnmidyfgrpyegiavfdgkkitvtgtlwngnkiiderlinpdgs llfrvtin
```

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

The invention claimed is:

1. A method to detect an interaction between a ligand and a target protein, comprising the steps of:
    (a) incubating (i) a fusion of a target protein and a peptide tag comprising 70% or greater sequence identity with VSGWRLFKKIS (SEQ ID NO: 5) with (ii) a complementary polypeptide comprising 70% or greater sequence identity with SEQ ID NO: 6, wherein the peptide tag and the complementary polypeptide are capable of forming a bioluminescent complex:
        (i) in the presence of the ligand to produce a test sample, and
        (ii) in the absence of the ligand, to produce a control sample;
    (b) treating said test and control samples under conditions that cause the target protein to unfold partially or completely unfold;
    (c) measuring signal from the bioluminescent complex in said test and control samples; and
    (d) comparing the measurement made in step (c) between the test and control samples, wherein alteration of the signal from said bioluminescent complex in the test sample compared to the control sample indicates the presence of the interaction between the ligand and the target protein.

2. The method of claim 1, wherein the fusion and the complementary polypeptide are within a cell, a cell lysate, or a reaction mixture.

3. The method of claim 2, wherein the ligand is added exogenously to the cell, the cell lysate, or the reaction mixture to produce the test sample.

4. The method of claim 1, wherein the conditions that cause the target protein to partially unfold comprise elevated temperature and/or a denaturant.

5. The method of claim 4, elevated temperature comprises one or more temperatures above physiologic temperature.

6. The method of claim 4, wherein elevated temperature comprises one or more temperatures near the approximate melting temperature of the target protein.

7. The method of claim 1, wherein a plurality of test samples are produced using a plurality of test ligands.

8. The method of claim 1, wherein the conditions cause the target protein to partially unfold.

9. The method of claim 1, wherein the peptide tag comprises 100% sequence identity with VSGWRLFKKIS (SEQ ID NO: 5).

10. The method of claim 1, wherein the complementary polypeptide comprises 90% or greater sequence identity with SEQ ID NO: 6.

11. The method of claim 1, wherein the complementary polypeptide comprises 100% sequence identity with SEQ ID NO: 6.

* * * * *